(12) United States Patent
Hu et al.

(10) Patent No.: US 10,639,291 B2
(45) Date of Patent: May 5, 2020

(54) HOMOGENOUS ANTIBODY DRUG CONJUGATES VIA ENZYMATIC METHODS

(71) Applicant: CSPC Dophen Corporation, Sacramento, CA (US)

(72) Inventors: Sean Hu, West Sacramento, CA (US); Lisha Allen, Sacramento, CA (US)

(73) Assignee: CSPC DOPHEN CORPORATION, Sacramento, CA (US)

( * ) Notice: Subject to any disclaimer, the term of this patent is extended or adjusted under 35 U.S.C. 154(b) by 0 days.

(21) Appl. No.: 15/986,665

(22) Filed: May 22, 2018

(65) Prior Publication Data
US 2018/0360793 A1    Dec. 20, 2018

Related U.S. Application Data

(62) Division of application No. 15/317,907, filed as application No. PCT/US2015/035375 on Jun. 11, 2015.

(60) Provisional application No. 62/011,534, filed on Jun. 12, 2014.

(51) Int. Cl.
| | |
|---|---|
| A61K 39/00 | (2006.01) |
| C07K 16/00 | (2006.01) |
| C12P 21/08 | (2006.01) |
| C07K 14/00 | (2006.01) |
| C07K 17/00 | (2006.01) |
| A61K 31/255 | (2006.01) |
| A61K 38/16 | (2006.01) |
| A61K 38/45 | (2006.01) |
| C07K 16/30 | (2006.01) |
| C07K 16/32 | (2006.01) |
| A61K 47/68 | (2017.01) |
| C07K 1/00 | (2006.01) |
| C07K 14/195 | (2006.01) |
| C07K 16/28 | (2006.01) |
| C12N 9/10 | (2006.01) |

(52) U.S. Cl.
CPC ............ *A61K 31/255* (2013.01); *A61K 38/16* (2013.01); *A61K 38/164* (2013.01); *A61K 38/45* (2013.01); *A61K 47/6803* (2017.08); *A61K 47/6855* (2017.08); *C07K 1/00* (2013.01); *C07K 14/195* (2013.01); *C07K 16/00* (2013.01); *C07K 16/2863* (2013.01); *C07K 16/30* (2013.01); *C07K 16/32* (2013.01); *C12N 9/1044* (2013.01); *C12Y 203/02013* (2013.01); *C07K 2317/24* (2013.01); *C07K 2317/40* (2013.01); *C07K 2317/41* (2013.01); *C07K 2317/524* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,156,956 A | 10/1992 | Motoki et al. | |
| 5,252,469 A | 10/1993 | Andou et al. | |
| 5,663,149 A | 9/1997 | Pettit et al. | |
| 5,731,183 A | 3/1998 | Kobayashi et al. | |
| 5,736,356 A | 4/1998 | Sano et al. | |
| 6,660,510 B2 | 12/2003 | Lin et al. | |
| 7,553,650 B2 | 6/2009 | Kashiwagi | |
| 9,427,478 B2 | 8/2016 | Bregeon et al. | |
| 10,357,472 B2 | 7/2019 | Hu | |
| 2005/0238649 A1 | 10/2005 | Doronina et al. | |
| 2010/0143970 A1 | 6/2010 | Yokoyama et al. | |
| 2013/0129753 A1 | 5/2013 | Doroski et al. | |
| 2016/0008485 A1 | 1/2016 | Marquette et al. | |
| 2017/0043033 A1* | 2/2017 | Strop | ................... A61K 31/427 |
| 2017/0106096 A1 | 4/2017 | Hu et al. | |
| 2018/0360794 A1 | 12/2018 | Hu et al. | |

FOREIGN PATENT DOCUMENTS

| | | |
|---|---|---|
| EP | 0555649 A2 | 8/1993 |
| JP | 2003-199569 A | 7/2003 |
| RU | 2400490 C2 | 9/2010 |
| WO | WO-1996/06931 A1 | 3/1996 |
| WO | WO-1996/22366 A1 | 7/1996 |
| WO | WO-1998/52976 A1 | 11/1998 |
| WO | WO-2000/34317 A2 | 6/2000 |
| WO | WO-2008/102007 A1 | 8/2008 |
| WO | WO-2008/102008 A1 | 8/2008 |
| WO | WO-2012/059882 A2 | 5/2012 |
| WO | WO-2013/068946 A2 | 5/2013 |
| WO | WO-2013/092998 A1 | 6/2013 |
| WO | WO-2015/191883 A1 | 12/2015 |

OTHER PUBLICATIONS

Encyclopedia Briannica, "Antibody", available online at https://www.britannica.com/science/antibody, 3 pages (2019) (Year: 2019).*
PhsiologyWeb, "Units per Volume Solution concentration Calculator", available online at https://www.physiologyweb.com/calculators/units_per_volume_solution_concentration_calculator.html, 3 pages (2005) (Year: 2005).*
Bruno et al., Ther. Deliv. 4:1443-1467 (2013) (Year: 2013).*
Altschul, S.F. et al. (Oct. 5, 1990). "Basic Local Alignment Search Tool," *J. Mol. Biol.* 215(3):403-410.

(Continued)

*Primary Examiner* — James H Alstrum-Acevedo
*Assistant Examiner* — Thea D' Ambrosio
(74) *Attorney, Agent, or Firm* — Morrison & Foerster LLP

(57) ABSTRACT

The present application in one aspect provide Fc-containing polypeptide conjugates comprising an Fc-containing polypeptide conjugated to a conjugate moiety, wherein the Fc-containing polypeptide comprises an N-glycosylated Fc region comprising an acceptor glutamine residue flanked by an N-glycosylation site and wherein the conjugate moiety is conjugated to the Fc-containing polypeptide via the acceptor glutamine residue. Also provided are methods of making such Fc-containing polypeptide conjugates by using a wild-type or engineered transglutaminases. Further provided are engineered transglutaminases specifically designed for carrying out such reactions.

16 Claims, 18 Drawing Sheets

Specification includes a Sequence Listing.

(56) References Cited

OTHER PUBLICATIONS

Axupa, J.Y. et al. (Oct. 2, 2012; e-published on Sep. 17, 2012). "Synthesis of Site-Specific Antibody-Drug Conjugates Using Unnatural Amino Acids," *Proc Natl Acad Sci USA* 109(40):16101-16106.

Boger, D.L. et al. (Apr. 25, 1995). "CC-1065 and the Duocarmycins: Unraveling the Keys to a New Class of Naturally Derived DNA Alkylating Agents," *Proc Natl Acad Sci USA* 92(9):3642-3649.

Devereux, J. et al. (Jan. 1984). "A Comprehensive Set of Sequence Analysis Programs for the VAX," *Nucl. Acid. Res.* 12(1 Pt. 1):387-395.

Gomez, N. et al. (Mar. 1, 2010). "Triple Light Chain Antibodies: Factors That Influence its Formation in Cell Culture," *Biotechnology and Bioengineering* 105(4):748-760.

Hamblett, K.J. et al. (Oct. 15, 2004). "Effects of Drug Loading on the Antitumor Activity of a Monoclonal Antibody Drug Conjugate," *Clinical Cancer Research* 10(20):7063-7070.

Innate Pharma. (Oct. 15, 2013). "A New Site Specific Antibody Conjugation Using Bacterial Transglutaminase," ADC Summit, San Francisco, located at: <URL: http://innate-pharma.com/sites/default/files/iph_adc_summit_2013.pdf>; last visited on Jan. 19, 2018, pp. 1-29.

Jeger, S. (2009). "Site-Specific Conjugation of Tumour-Targeting Antibodies Using Transglutaminase," Doctoral Thesis—A Dissertation submitted to ETH Zurich for the degree of Doctor of Sciences, 151 pages.

Jeger, S. et al. (2010). "Site-Specific and Stoichiometric Modification of Antibodies by Bacterial Transglutaminase," *Angew. Chem. Int. Ed.* 49:9995-9997.

Junutula, J.R. et al. (Aug. 2008; e-published on Jul. 20, 2008). "Site-Specific Conjugation of a Cytotoxic Drug to an Antibody Improves the Therapeutic Index," *Nature Biotechnology* 26(8):925-932.

Lhospice, F. et al. (Oct. 2014). Abstract 2514: Towards Homogenous adcs: A New Site-Specific Antibody Conjugation Using Bacterial Transglutaminase (btg-adc) Proceedings of AACR Annual Meeting, Apr. 5-9, 2014; San Diego CA, *Cancer Research* 74(19 Supplement): Abstract No. 2514.

Lin, Y-S. et al. (Jan. 30, 2004). "Cloning and Expression of the Transglutaminase Gene from *Streptoverticillium ladakanum* in *Streptomyces lividans*," *Process Biochemistry* 39(5):591-598.

Lyon, R.P. et al. (2012). "Conjugation of Anticancer Drugs Through Endogenous Monoclonal Antibody Cysteine Residues," Chapter 6 in *Methods in Enzymology*, Elsevier Inc., 502:123-138.

Pettit, R.K. et al. (Nov. 1998). "Specific Activities of Dolastatin 10 and Peptide Derivatives against *Cryptococcus neoformans*," *Antimicrobial Agents Chemotherapy* 42(11):2961-2965.

Remillard, S. et al. (Sep. 19, 1975). "Antimitotic Activity of the Potent Tumor Inhibitor Maytansine," *Science* 189(4207):1002-1005.

Strop, P. et al. (Feb. 21, 2013). "Location Matters: Site of Conjugation Modulates Stability and Pharmacokinetics of Antibody Drug Conjugates," *Chemistry & Biology* 20(2):161-167.

Russell, P.R. (1985). "Transcription of the Triose-Phosphate-Isomerase Gene of *Schizosaccharomyces pombe* Initiates From a Start Point Different From That in *Saccharomyces cerevisiae*," *Gene* 40(1):125-130.

Tanaka, T. et al. (Apr. 11, 2005). "N-Terminal Glycine-Specific Protein Conjugation Catalyzed by Microbial Transglutaminase," *FEBS Letters* 579(10):2092-2096.

Wakankar, A. et al. (Mar.-Apr. 2011). "Analytical Methods for Physicochemical Characterization of Antibody Drug Conjugates," *mAbs* 3(2):161-172.

Wikipedia—Free Encyclopedia. (Date Unknown). "*Streptomyces mobaraensis*," Located at <https://en.wikipedia.org/wiki/Streptomyces_mobaraensis>, last visited on Aug. 9, 2018, three pages.

International Preliminary Report on Patentability dated Dec. 22, 2016, for PCT/US2015/035375 Internationally filed on Jun. 11, 2015, ten pages.

International Search report and Written Opinion dated Oct. 2, 2015, for PCT/US2015/035375 Internationally filed on Jun. 11, 2015, eighteen pages.

U.S. Appl. No. 15/986,668, filed May 22, 2018, by Hu et al. (Copy not submitted herewith pursuant to the waiver of 37 C.F.R. § 1.98(a)(2)(iii) issued by the Office on Sep. 21, 2004.).

Gasser, B. et al. (Feb. 2007; e-pub. Nov. 22, 2006). "Antibody Production with Yeasts and Filamentous Fungi: On the Road to Large Scale?," *Biotechnologies Letters* 29(2):201-212, (Abstract Only).

Pakula, A.A. et al. (1989). "Genetics Analysis of Protein Stability and Function," *Annual Review of Genetics* 23(1):289-310.

Dennler, P. et al. (2013). "Enzymatic Antibody Modification by Bacterial Transglutaminase," Chapter 12 in Methods In Molecular Biology, 1045:205-215.

Jeger, S. et al. (2010). "Site-Specific and Stoichiometric Modification of Antibodies by Bacterial Transglutaminase," Supporting Information, Angew. Chem. Int. Ed., pp. 1-45.

Josten, A. et al. (Jun. 1, 2000). "Use of Microbial Transglutaminase for the Enzymatic Biotinylation of Antibodies," Journal of Immunological Methods 240(1-2):47-54.

Mindt, T.L. et al. (Jan. 1, 2008). "Modification of Different IgG1 Antibodies Via Glutamine and Lysine Using Bacterial and Human Tissue Transglutaminase," Bioconjugate Chemistry 19(1):271-278.

* cited by examiner

```
Protein
TG_SL    1    DSDERVTPPAEPLDRMPDPYRPSYGRAETIVNNYIRKWQQVYSHRDGRKQQMTEEQREWL    60
              DSD+PVTPPAEPLDRMPDPYPPSYGRAET+VNNYIRKWQQVYSHRDGPKQQMTEEQREWL
TG_SM    1    DSDDRVTPPAEPLDRMPDPYRPSYGRAETVVNNYIRKWQQVYSHRDGRKQQMTEEQREWL    60

TG_SL   61    SYGCVGVTWVNSGQYPTNRLAFAFFDEDKYKNELKNGRPRSGETRAEFEGRVAKDSFDEA   120
              SYGCVGVTWVNSGQYPTNRLAFA FDED++KNELKNGRPRSGETRAEFEGRVAK+SFDE
TG_SM   61    SYGCVGVTWVNSGQYPTNRLAFASFDEDRFKNELKNGRPRSGETRAEFEGRVAKESFDEE   120

TG_SL  121    KGFQRARDVASVMNKALENAHDEGAYLDNLKKELANGNDALPNEDARSPFYSALRNTPSF   180
              KGFQRAR+VASVMN+ALENAHDE AYLDNLKKELANGNDALRNEDARSPFYSALRNTPSF
TG_SM  121    KGFQRAREVASVMNRALENAHDESAYLDNLKKELANGNDALRNEDARSPFYSALRNTPSF   180

TG_SL  181    KDPNGGNHDPSKMKAVIYSKHFWSGQDRSGSSDKPKYGDPEAFRPDRGTGLVDMSPDRNI   240
              K+RNGGNHDPS+MKAVIYSKHFWSGQDRS S+DKRKYGDP+AFRP  GTGLVDMSRDRNI
TG_SM  181    KERNGGNHDPSRMKAVIYSKHFWSGQDRSSSADKRKYGDPDAFRPAPGTGLVDMSRDPNI   240

TG_SL  241    PRSPTSPGESFVNFDYGWFGAQTEADADKTVWTHGNHYHAPNGSLGAMHVYESKFRNWSD   300
              PRSPTSPGE FVNFDYGWFGAQTEADADKTVWTHGNHYHAPNGSLGAMHVYESKFRNWS+
TG_SM  241    PRSPTSPGEGFVNFDYGWFGAQTEADADKTVWTHGNHYHAPNGSLGAMHVYESKFRNWSE   300

TG_SL  301    GYSDFDRGAYVVTFVPKSWNTAPDKVTQGWP    331    (SEQ ID NO:16)
              GYSDFDRGAYV+TF+PKSWNTAPDKV QGWP
TG_SM  301    GYSDFDRGAYVITFIPKSWNTAPDKVKQGWP    331    (SEQ ID NO:18)
```

Figure 3.

```
            [SEQ ID NO:17]
             1  2  3  4  5
                   M  P  D  S  D  E  R  V  T  P  P  A  E  P  L  D  R  16
M  P  D  P  Y  R  P  S  Y  G  R  A  E  T  I  V  N  N  Y  I
R  K  W  Q  Q  V  Y  S  H  R  D  G  R  K  Q  Q  M  T  E  E  56
Q  R  E  W  L  S  Y  G  C  V  G  V  T  W  V  N  S  G  Q  Y
P  T  N  R  L  A  F  A  F  F  D  E  D  K  Y  K  N  E  L  K  96
N  G  R  P  R  S  G  E  T  R  A  E  F  E  G  R  V  A  K  D
S  F  D  E  A  K  G  F  Q  R  A  R  D  V  A  S  V  M  N  K  136
A  L  E  N  A  H  D  E  G  A  Y  L  D  N  L  K  K  E  L  A
N  G  N  D  A  L  R  N  E  D  A  R  S  P  F  Y  S  A  L  R  176
N  T  P  S  F  K  D  R  N  G  G  N  H  D  P  S  K  M  K  A
V  I  Y  S  K  H  F  W  S  G  Q  D  R  S  G  S  S  D  K  R  216
K  Y  G  D  P  E  A  F  R  P  D  R  G  T  G  L  V  D  M  S
R  D  R  N  I  P  R  S  P  T  S  P  G  E  S  F  V  N  F  D  256
Y  G  W  F  G  A  Q  T  E  A  D  A  D  K  T  V  W  T  H  G
N  H  Y  H  A  P  N  G  S  L  G  A  M  H  V  Y  E  S  K  F  296
R  N  W  S  D  G  Y  S  D  F  D  R  G  A  Y  V  V  T  F  V
P  K  S  W  N  T  A  P  D  K  V  T  Q  G  W  P  L  E  H  H  336
H  H  H  H  H  H  -
```

Wild type SL mTgase was cloned into pET39+ vector using NdeI and XhoI sites with an extra proline. Three regions near the active site entrance are targeted for deletion or mutation to enlarge the substrate binding pocket based on IgG1 and TG_SM crystal structure docking. Deletions are greyed, unlined or stricken-through. Active mutants are specified bellow.

Mutant 1: Deletion from $P^1$-$E^5$
Mutant 2: Deletion from $P^{245}$-$P^{248}$
Mutant 3: Deletion from $N^{283}$-$L^{286}$
Mutant 4: Deletions of $P^1$-$E^5$ and $N^{283}$-$L^{286}$
Mutant 5: Deletion of all three regions specified by mutants 1,2 and 3
Mutant 6: Deletion of $P^1$-$E^5$ and replace $H^{286}$-$A^{288}$ with G.
Mutant 7: Deletion of $P^1$-$E^5$ and replace $A^{281}$-$H^{290}$ with G.

2A. One_Step mAB and Toxin Conjugation

Figure 6.
A.
Only Heavy Chain of IgG1 Is Conjugated with MDC
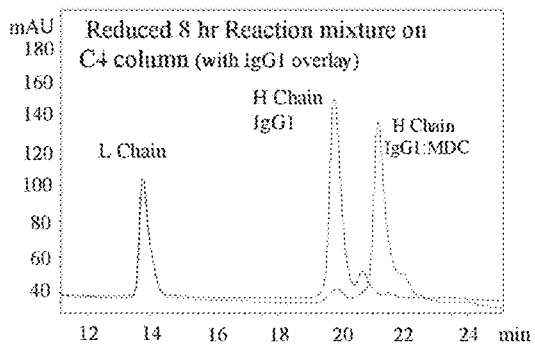
B.
Conjugation Reaction Gives IgG1-MDC 1:1 and 1:2 Forms
At the onset of the reaction, 1:1 conjugate (one H Chain modified) was the only product. After 8 hrs, 1:2 conjugate (2 H Chains modified) reaches 80%.
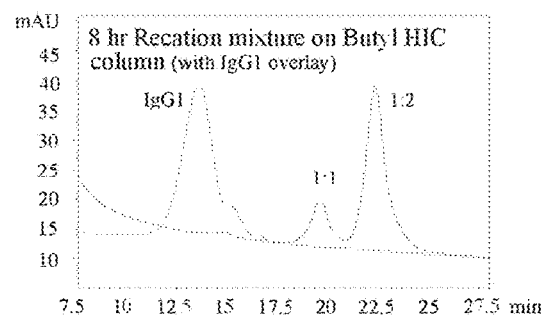
C.
Site-Specific Conjugation of IgG2 and IgG4 with MDC
IgG2-MDC Reaction Mixture on Phenyl Column
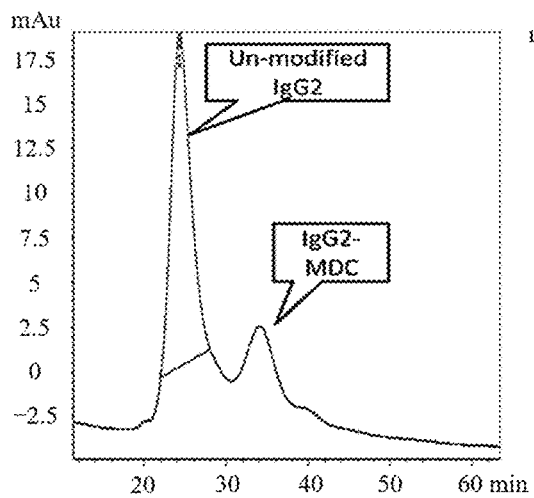
IgG4-MDC Reaction Mixture on C4 Column
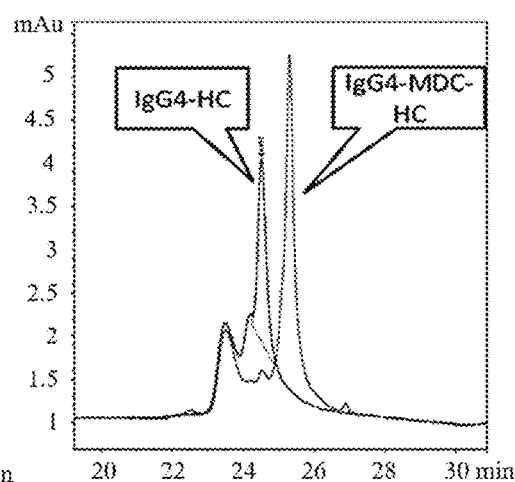

Figure 12.
Non-cleavable linkers with MMAE: PEGx, where x=2, 4, 6, 8, 10, 12, 16, 20, 24
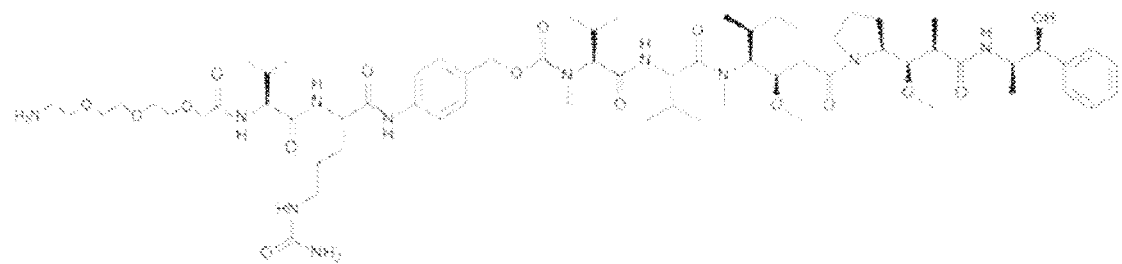
Cleavable linker PEG3c with MMAE Figure 18.
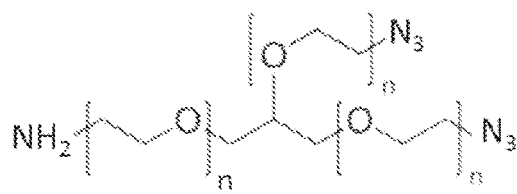
3-arm PEG linkers (1-5k Da, where n=7-38)
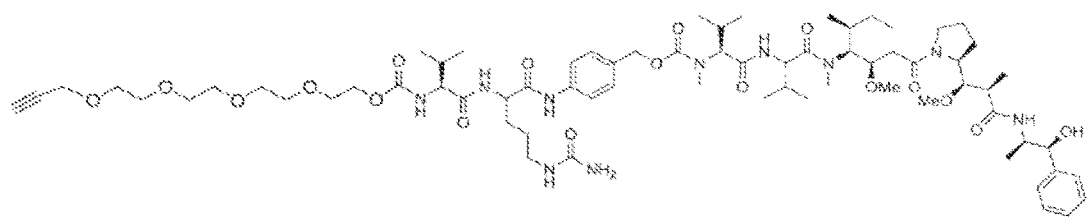
Alkyne-PEG4c-MMAE

```
                    SEQUENCE LISTING

<160> NUMBER OF SEQ ID NOS: 43

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7, 11
<223> OTHER INFORMATION: Xaa = Y or F

<400> SEQUENCE: 1

Lys Pro Arg Glu Glu Gln Xaa Asn Ser Thr Xaa Arg
1               5                  10

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct

<400> SEQUENCE: 2

Lys Pro Arg Glu Glu Gln Tyr Asn Ser Thr Tyr Arg
1               5                  10

<210> SEQ ID NO 3
<211> LENGTH: 110
<212> TYPE: PRT
<213> ORGANISM: Homo sapiens

<400> SEQUENCE: 3

Ala Pro Glu Leu Leu Gly Gly Pro Ser Val Phe Leu Phe Pro Pro Lys
1               5                  10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
            85                  90                  95

Ala Leu Pro Ala Pro Ile Glu Lys Thr Ile Ser Lys Ala Lys
            100                 105                 110

<210> SEQ ID NO 4
<211> LENGTH: 109
<212> TYPE: PRT
<213> ORGANISM: Homo sapiens

<400> SEQUENCE: 4

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105

<210> SEQ ID NO 5
<211> LENGTH: 110
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys
            100                 105                 110

<210> SEQ ID NO 6
<211> LENGTH: 110
<212> TYPE: PRT
<213> ORGANISM: Homo sapiens

<400> SEQUENCE: 6

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30
```

```
Val Val Asp Val Ser Gln Glu Asp Pro Glu Val Gln Phe Asn Trp Tyr
         35                  40                  45
Val Asp Gly Val Glu Val His Asn Ala Lys Thr Lys Pro Arg Glu Glu
 50                  55                  60
Gln Phe Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Gly Leu Pro Ser Ser Ile Glu Lys Thr Ile Ser Lys Ala Lys
                100                 105                 110
```

<210> SEQ ID NO 7
<211> LENGTH: 107
<212> TYPE: PRT
<213> ORGANISM: Mus musculus

<400> SEQUENCE: 7

```
Val Pro Glu Val Ser Ser Val Phe Ile Phe Pro Pro Lys Pro Lys Asp
 1               5                  10                  15
Val Leu Thr Ile Thr Leu Thr Pro Lys Val Thr Cys Val Val Val Asp
                 20                  25                  30
Ile Ser Lys Asp Asp Pro Glu Val Gln Phe Ser Trp Phe Val Asp Asp
         35                  40                  45
Val Glu Val His Thr Ala Gln Thr Gln Pro Arg Glu Glu Gln Phe Asn
 50                  55                  60
Ser Thr Phe Arg Ser Val Ser Glu Leu Pro Ile Met His Gln Asp Trp
 65                  70                  75                  80
Leu Asn Gly Lys Glu Phe Lys Cys Arg Val Asn Ser Ala Ala Phe Pro
                 85                  90                  95
Ala Pro Ile Glu Lys Thr Ile Ser Lys Thr Lys
                100                 105
```

<210> SEQ ID NO 8
<211> LENGTH: 110
<212> TYPE: PRT
<213> ORGANISM: Mus musculus

<400> SEQUENCE: 8

```
Ala Pro Asp Leu Leu Gly Gly Pro Ser Val Phe Ile Phe Pro Pro Lys
 1               5                  10                  15
Ile Lys Asp Val Leu Met Ile Ser Leu Ser Pro Met Val Thr Cys Val
                 20                  25                  30
Val Val Asp Val Ser Glu Asp Asp Pro Asp Val Gln Ile Ser Trp Phe
         35                  40                  45
Val Asn Asn Val Glu Val His Thr Ala Gln Thr Gln Thr His Arg Glu
 50                  55                  60
Asp Tyr Asn Ser Thr Leu Arg Val Val Ser Ala Leu Pro Ile Gln His
 65                  70                  75                  80
Gln Asp Trp Met Ser Gly Lys Glu Phe Lys Cys Lys Val Asn Asn Arg
                 85                  90                  95
Ala Leu Pro Ser Pro Ile Glu Lys Thr Ile Ser Lys Pro Arg
                100                 105                 110
```

<210> SEQ ID NO 9
<211> LENGTH: 110
<212> TYPE: PRT
<213> ORGANISM: Mus musculus

<400> SEQUENCE: 9

Ala Pro Asn Leu Leu Gly Gly Pro Ser Val Phe Ile Phe Pro Pro Lys
1               5                   10                  15

Ile Lys Asp Val Leu Met Ile Ser Leu Ser Pro Ile Val Thr Cys Val
            20                  25                  30

Val Val Asp Val Ser Glu Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Leu Arg Val Val Ser Ala Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ala Pro Ile Glu Arg Thr Ile Ser Lys Pro Lys
            100                 105                 110

<210> SEQ ID NO 10
<211> LENGTH: 110
<212> TYPE: PRT
<213> ORGANISM: Mus musculus

<400> SEQUENCE: 10

Ala Pro Asn Leu Glu Gly Gly Pro Ser Val Phe Ile Phe Pro Pro Asn
1               5                   10                  15

Ile Lys Asp Val Leu Met Ile Ser Leu Thr Pro Lys Val Thr Cys Val
            20                  25                  30

Val Val Asp Val Ser Glu Asp Pro Asp Val Gln Ile Ser Trp Phe
        35                  40                  45

Val Asn Asn Val Glu Val His Thr Ala Gln Thr Gln Thr His Arg Glu
    50                  55                  60

Asp Tyr Asn Ser Thr Ile Arg Val Val Ser Leu Pro Ile Gln His
65                  70                  75                  80

Gln Asp Trp Met Ser Gly Lys Glu Phe Lys Cys Lys Val Asn Asn Lys
                85                  90                  95

Asp Leu Pro Ser Pro Ile Glu Arg Thr Ile Ser Lys Ile Lys
            100                 105                 110

<210> SEQ ID NO 11
<211> LENGTH: 110
<212> TYPE: PRT
<213> ORGANISM: Mus musculus

<400> SEQUENCE: 11

Ala Gly Asn Ile Leu Gly Gly Pro Ser Val Phe Ile Phe Pro Pro Lys
1               5                   10                  15

Pro Lys Asp Ala Leu Met Ile Ser Leu Thr Pro Lys Val Thr Cys Val
            20                  25                  30

Val Val Asp Val Ser Glu Asp Asp Pro Asp Val His Val Ser Trp Phe
        35                  40                  45

Val Asp Asn Lys Glu Val His Thr Ala Trp Thr Gln Pro Arg Glu Ala
    50                  55                  60

Gln Tyr Asn Ser Thr Phe Arg Val Val Ser Ala Leu Pro Ile Gln His
65                  70                  75                  80

Gln Asp Trp Met Arg Gly Lys Glu Phe Lys Cys Lys Val Asn Asn Lys
                85                  90                  95

Ala Leu Pro Ala Pro Ile Glu Arg Thr Ile Ser Lys Pro Lys
            100                 105                 110

<210> SEQ ID NO 12
<211> LENGTH: 107
<212> TYPE: PRT
<213> ORGANISM: Rattus norvegicus

<400> SEQUENCE: 12

Gly Ser Glu Val Ser Ser Val Phe Ile Phe Pro Pro Lys Thr Lys Asp
1               5                   10                  15

Val Leu Thr Ile Thr Leu Thr Pro Lys Val Thr Cys Val Val Val Asp
                20                  25                  30

Ile Ser Gln Asn Asp Pro Glu Val Arg Phe Ser Trp Phe Ile Asp Asp
            35                  40                  45

Val Glu Val His Thr Ala Gln Thr His Ala Pro Glu Lys Gln Ser Asn
        50                  55                  60

Ser Thr Leu Arg Ser Val Ser Glu Leu Pro Ile Val His Arg Asp Trp
65                  70                  75                  80

Leu Asn Gly Lys Thr Phe Lys Cys Lys Val Asn Ser Gly Ala Phe Pro
                85                  90                  95

Ala Pro Ile Glu Lys Ser Ile Ser Lys Pro Glu
            100                 105

<210> SEQ ID NO 13
<211> LENGTH: 107
<212> TYPE: PRT
<213> ORGANISM: Rattus norvegicus

<400> SEQUENCE: 13

Gly Ser Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
                20                  25                  30

Ile Ser Gln Asp Asp Pro Glu Val His Phe Ser Trp Phe Val Asp Asp
            35                  40                  45

Val Glu Val His Thr Ala Gln Thr Arg Pro Pro Glu Glu Gln Phe Asn
        50                  55                  60

Ser Thr Phe Arg Ser Val Ser Glu Leu Pro Ile Leu His Gln Asp Trp
65                  70                  75                  80

Leu Asn Gly Arg Thr Phe Arg Cys Lys Val Thr Ser Ala Ala Phe Pro
                85                  90                  95

Ser Pro Ile Glu Lys Thr Ile Ser Lys Pro Glu
            100                 105

<210> SEQ ID NO 14
<211> LENGTH: 110
<212> TYPE: PRT
<213> ORGANISM: Rattus norvegicus

<400> SEQUENCE: 14

Val Pro Glu Leu Leu Gly Gly Pro Ser Val Phe Ile Phe Pro Pro Lys
1               5                   10                  15

Pro Lys Asp Ile Leu Leu Ile Ser Gln Asn Ala Lys Val Thr Cys Val
                20                  25                  30

```
Val Val Asp Val Ser Glu Glu Pro Asp Val Gln Phe Ser Trp Phe
        35                  40                  45

Val Asn Asn Val Glu Val His Thr Ala Gln Thr Gln Pro Arg Glu Glu
 50                  55                  60

Gln Tyr Asn Ser Thr Phe Arg Val Val Ser Ala Leu Pro Ile Gln His
 65                  70                  75                  80

Gln Asp Trp Met Ser Gly Lys Glu Phe Lys Cys Lys Val Asn Asn Lys
                 85                  90                  95

Ala Leu Pro Ser Pro Ile Glu Lys Thr Ile Ser Lys Pro Lys
                100                 105                 110

<210> SEQ ID NO 15
<211> LENGTH: 109
<212> TYPE: PRT
<213> ORGANISM: Rattus norvegicus

<400> SEQUENCE: 15

Asp Asp Asn Leu Gly Arg Pro Ser Val Phe Ile Phe Pro Pro Lys Pro
 1               5                  10                  15

Lys Asp Ile Leu Met Ile Thr Leu Thr Pro Lys Val Thr Cys Val Val
                 20                  25                  30

Val Asp Val Ser Glu Glu Pro Asp Val Gln Phe Ser Trp Phe Val
        35                  40                  45

Asp Asn Val Arg Val Phe Thr Ala Gln Thr Gln Pro His Glu Glu Gln
 50                  55                  60

Leu Asn Gly Thr Phe Arg Val Val Ser Thr Leu His Ile Gln His Gln
 65                  70                  75                  80

Asp Trp Met Ser Gly Lys Glu Phe Lys Cys Lys Val Asn Asn Lys Asp
                 85                  90                  95

Leu Pro Ser Pro Ile Glu Lys Thr Ile Ser Lys Pro Arg
                100                 105

<210> SEQ ID NO 16
<211> LENGTH: 331
<212> TYPE: PRT
<213> ORGANISM: Strep Ladakanum

<400> SEQUENCE: 16

Asp Ser Asp Glu Arg Val Thr Pro Ala Glu Pro Leu Asp Arg Met
 1               5                  10                  15

Pro Asp Pro Tyr Arg Pro Ser Tyr Gly Arg Ala Glu Thr Ile Val Asn
                 20                  25                  30

Asn Tyr Ile Arg Lys Trp Gln Gln Val Tyr Ser His Arg Asp Gly Arg
                 35                  40                  45

Lys Gln Gln Met Thr Glu Glu Gln Arg Glu Trp Leu Ser Tyr Gly Cys
 50                  55                  60

Val Gly Val Thr Trp Val Asn Ser Gly Gln Tyr Pro Thr Asn Arg Leu
 65                  70                  75                  80

Ala Phe Ala Phe Phe Asp Glu Asp Lys Tyr Lys Asn Glu Leu Lys Asn
                 85                  90                  95

Gly Arg Pro Arg Ser Gly Glu Thr Arg Ala Glu Phe Glu Gly Arg Val
                100                 105                 110

Ala Lys Asp Ser Phe Asp Glu Ala Lys Gly Phe Gln Arg Ala Arg Asp
        115                 120                 125

Val Ala Ser Val Met Asn Lys Ala Leu Glu Asn Ala His Asp Glu Gly
130                 135                 140
```

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
            165                 170                 175

Thr Pro Ser Phe Lys Asp Arg Asn Gly Asn His Asp Pro Ser Lys
        180                 185                 190

Met Lys Ala Val Ile Tyr Ser Lys His Phe Trp Ser Gly Gln Asp Arg
        195                 200                 205

Ser Gly Ser Ser Asp Lys Arg Lys Tyr Gly Asp Pro Glu Ala Phe Arg
        210                 215                 220

Pro Asp Arg Gly Thr Gly Leu Val Asp Met Ser Arg Asp Arg Asn Ile
225                 230                 235                 240

Pro Arg Ser Pro Thr Ser Pro Gly Glu Ser Phe Val Asn Phe Asp Tyr
                245                 250                 255

Gly Trp Phe Gly Ala Gln Thr Glu Ala Asp Ala Asp Lys Thr Val Trp
            260                 265                 270

Thr His Gly Asn His Tyr His Ala Pro Asn Gly Ser Leu Gly Ala Met
        275                 280                 285

His Val Tyr Glu Ser Lys Phe Arg Asn Trp Ser Asp Gly Tyr Ser Asp
290                 295                 300

Phe Asp Arg Gly Ala Tyr Val Val Thr Phe Val Pro Lys Ser Trp Asn
305                 310                 315                 320

Thr Ala Pro Asp Lys Val Thr Gln Gly Trp Pro
                325                 330

<210> SEQ ID NO 17
<211> LENGTH: 342
<212> TYPE: PRT
<213> ORGANISM: Artificial Sequence
<220> FEATURE:
<223> OTHER INFORMATION: Synthetic Construct

<400> SEQUENCE: 17

Pro Asp Ser Asp Glu Arg Val Thr Pro Pro Ala Glu Pro Leu Asp Arg
1               5                   10                  15

Met Pro Asp Pro Tyr Arg Pro Ser Tyr Gly Arg Ala Glu Thr Ile Val
            20                  25                  30

Asn Asn Tyr Ile Arg Lys Trp Gln Gln Val Tyr Ser His Arg Asp Gly
        35                  40                  45

Arg Lys Gln Gln Met Thr Glu Glu Gln Arg Glu Trp Leu Ser Tyr Gly
    50                  55                  60

Cys Val Gly Val Thr Trp Val Asn Ser Gly Gln Tyr Pro Thr Asn Arg
65                  70                  75                  80

Leu Ala Phe Ala Phe Asp Glu Asp Lys Tyr Lys Asn Glu Leu Lys
                85                  90                  95

Asn Gly Arg Pro Arg Ser Gly Glu Thr Arg Ala Glu Phe Glu Gly Arg
            100                 105                 110

Val Ala Lys Asp Ser Phe Asp Glu Ala Lys Gly Phe Gln Arg Ala Arg
        115                 120                 125

Asp Val Ala Ser Val Met Asn Lys Ala Leu Glu Asn Ala His Asp Glu
    130                 135                 140

Gly Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
                165                 170                 175

```
Asn Thr Pro Ser Phe Lys Asp Arg Asn Gly Gly Asn His Asp Pro Ser
            180                 185                 190

Lys Met Lys Ala Val Ile Tyr Ser Lys His Phe Trp Ser Gly Gln Asp
        195                 200                 205

Arg Ser Gly Ser Ser Asp Lys Arg Lys Tyr Gly Asp Pro Glu Ala Phe
    210                 215                 220

Arg Pro Asp Arg Gly Thr Gly Leu Val Asp Met Ser Arg Asp Arg Asn
225                 230                 235                 240

Ile Pro Arg Ser Pro Thr Ser Pro Gly Glu Ser Phe Val Asn Phe Asp
                245                 250                 255

Tyr Gly Trp Phe Gly Ala Gln Thr Glu Ala Asp Ala Asp Lys Thr Val
                260                 265                 270

Trp Thr His Gly Asn His Tyr His Ala Pro Asn Gly Ser Leu Gly Ala
            275                 280                 285

Met His Val Tyr Glu Ser Lys Phe Arg Asn Trp Ser Asp Gly Tyr Ser
        290                 295                 300

Asp Phe Asp Arg Gly Ala Tyr Val Val Thr Phe Val Pro Lys Ser Trp
305                 310                 315                 320

Asn Thr Ala Pro Asp Lys Val Thr Gln Gly Trp Pro Leu Glu His His
                325                 330                 335

His His His His His His
            340

<210> SEQ ID NO 18
<211> LENGTH: 331
<212> TYPE: PRT
<213> ORGANISM: Strep Mobaraensis

<400> SEQUENCE: 18

Asp Ser Asp Asp Arg Val Thr Pro Pro Ala Glu Pro Leu Asp Arg Met
1               5                   10                  15

Pro Asp Pro Tyr Arg Pro Ser Tyr Gly Arg Ala Glu Thr Val Val Asn
            20                  25                  30

Asn Tyr Ile Arg Lys Trp Gln Gln Val Tyr Ser His Arg Asp Gly Arg
        35                  40                  45

Lys Gln Gln Met Thr Glu Glu Gln Arg Glu Trp Leu Ser Tyr Gly Cys
    50                  55                  60

Val Gly Val Thr Trp Val Asn Ser Gly Gln Tyr Pro Thr Asn Arg Leu
65                  70                  75                  80

Ala Phe Ala Ser Phe Asp Glu Asp Arg Phe Lys Asn Glu Leu Lys Asn
                85                  90                  95

Gly Arg Pro Arg Ser Gly Glu Thr Arg Ala Glu Phe Glu Gly Arg Val
            100                 105                 110

Ala Lys Glu Ser Phe Asp Glu Lys Gly Phe Gln Arg Ala Arg Glu
        115                 120                 125

Val Ala Ser Val Met Asn Arg Ala Leu Glu Asn Ala His Asp Glu Ser
    130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Glu Arg Asn Gly Gly Asn His Asp Pro Ser Arg
            180                 185                 190

Met Lys Ala Val Ile Tyr Ser Lys His Phe Trp Ser Gly Gln Asp Arg
        195                 200                 205
```

```
Ser Ser Ser Ala Asp Lys Arg Lys Tyr Gly Asp Pro Asp Ala Phe Arg
        210                 215                 220

Pro Ala Pro Gly Thr Gly Leu Val Asp Met Ser Arg Asp Arg Asn Ile
225                 230                 235                 240

Pro Arg Ser Pro Thr Ser Pro Gly Glu Gly Phe Val Asn Phe Asp Tyr
                245                 250                 255

Gly Trp Phe Gly Ala Gln Thr Glu Ala Asp Ala Asp Lys Thr Val Trp
                260                 265                 270

Thr His Gly Asn His Tyr His Ala Pro Asn Gly Ser Leu Gly Ala Met
                275                 280                 285

His Val Tyr Glu Ser Lys Phe Arg Asn Trp Ser Glu Gly Tyr Ser Asp
                290                 295                 300

Phe Asp Arg Gly Ala Tyr Val Ile Thr Phe Ile Pro Lys Ser Trp Asn
305                 310                 315                 320

Thr Ala Pro Asp Lys Val Lys Gln Gly Trp Pro
                325                 330

<210> SEQ ID NO 19
<211> LENGTH: 331
<212> TYPE: PRT
<213> ORGANISM: Artificial Sequence
<220> FEATURE:
<223> OTHER INFORMATION: Consensus Sequence
<220> FEATURE:
<221> NAME/KEY: VARIANT
<222> LOCATION: 4, 30, 84, 89, 90, 115, 120, 128, 135, 144, 182, 192,
      210, 212, 221, 226, 227, 250, 300, 312, 315, 327
<223> OTHER INFORMATION: Xaa = Any Amino Acid

<400> SEQUENCE: 19

Asp Ser Asp Xaa Arg Val Thr Pro Pro Ala Glu Pro Leu Asp Arg Met
1               5                   10                  15

Pro Asp Pro Tyr Arg Pro Ser Tyr Gly Arg Ala Glu Thr Xaa Val Asn
                20                  25                  30

Asn Tyr Ile Arg Lys Trp Gln Gln Val Tyr Ser His Arg Asp Gly Arg
                35                  40                  45

Lys Gln Gln Met Thr Glu Glu Gln Arg Glu Trp Leu Ser Tyr Gly Cys
50                  55                  60

Val Gly Val Thr Trp Val Asn Ser Gly Gln Tyr Pro Thr Asn Arg Leu
65                  70                  75                  80

Ala Phe Ala Xaa Phe Asp Glu Asp Xaa Xaa Lys Asn Glu Leu Lys Asn
                85                  90                  95

Gly Arg Pro Arg Ser Gly Glu Thr Arg Ala Glu Phe Glu Gly Arg Val
                100                 105                 110

Ala Lys Xaa Ser Phe Asp Glu Xaa Lys Gly Phe Gln Arg Ala Arg Xaa
                115                 120                 125

Val Ala Ser Val Met Asn Xaa Ala Leu Glu Asn Ala His Asp Glu Xaa
                130                 135                 140

Ala Tyr Leu Asp Asn Leu Lys Lys Glu Leu Ala Asn Gly Asn Asp Ala
145                 150                 155                 160

Leu Arg Asn Glu Asp Ala Arg Ser Pro Phe Tyr Ser Ala Leu Arg Asn
                165                 170                 175

Thr Pro Ser Phe Lys Xaa Arg Asn Gly Gly Asn His Asp Pro Ser Xaa
                180                 185                 190

Met Lys Ala Val Ile Tyr Ser Lys His Phe Trp Ser Gly Gln Asp Arg
                195                 200                 205
```

-continued

Ser Xaa Ser Xaa Asp Lys Arg Lys Tyr Gly Asp Pro Xaa Ala Phe Arg
    210             215                 220

Pro Xaa Xaa Gly Thr Gly Leu Val Asp Met Ser Arg Asp Arg Asn Ile
225             230                 235                 240

Pro Arg Ser Pro Thr Ser Pro Gly Glu Xaa Phe Val Asn Phe Asp Tyr
                245                 250                 255

Gly Trp Phe Gly Ala Gln Thr Glu Ala Asp Ala Asp Lys Thr Val Trp
                260                 265                 270

Thr His Gly Asn His Tyr His Ala Pro Asn Gly Ser Leu Gly Ala Met
                275                 280                 285

His Val Tyr Glu Ser Lys Phe Arg Asn Trp Ser Xaa Gly Tyr Ser Asp
    290                 295                 300

Phe Asp Arg Gly Ala Tyr Val Xaa Thr Phe Xaa Pro Lys Ser Trp Asn
305             310                 315                 320

Thr Ala Pro Asp Lys Val Xaa Gln Gly Trp Pro
                325                 330

<210> SEQ ID NO 20
<211> LENGTH: 19
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct

<400> SEQUENCE: 21

Val Glu Ser Gly Gly Gly Leu Gln Pro Gly Gly Ser Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Gln Ala Pro Gly Lys Gly Leu Glu Trp Val Ala Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Asn Thr Ala Tyr Leu Gln Met Asn Ser Leu Arg
1               5                   10

<210> SEQ ID NO 24
<211> LENGTH: 26
<212> TYPE: PRT
<213> ORGANISM: Artificial Sequence
<220> FEATURE:
<223> OTHER INFORMATION: Synthetic Construct

<400> SEQUENCE: 24

Trp Gly Gly Asp Gly Phe Tyr Ala Met Asp Tyr Trp Gly Gln Gly Thr
1               5                   10                  15

Leu Val Thr Val Ser Ser Ala Ser Thr Lys
            20                  25

<210> SEQ ID NO 25
<211> LENGTH: 16
<212> TYPE: PRT
<213> ORGANISM: Artificial Sequence
<220> FEATURE:
<223> OTHER INFORMATION: Synthetic Construct

<400> SEQUENCE: 25

Thr Ser Gly Val His Thr Phe Pro Ala Val Leu Gln Ser Ser Gly Leu
1               5                   10                  15

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Gly Thr Gln Thr Tyr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Glu Glu Gln Tyr Asp Ser Thr Tyr Arg
1               5

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Asn Ala Lys Thr Lys Pro Arg Glu Glu Gln Tyr
1               5                   10

<210> SEQ ID NO 29
<211> LENGTH: 19
<212> TYPE: PRT
<213> ORGANISM: Artificial Sequence
<220> FEATURE:
<223> OTHER INFORMATION: Synthetic Construct

```
<400> SEQUENCE: 29

Glu Val Gln Leu Val Glu Ser Gly Gly Gly Leu Val Gln Pro Gly Gly
1               5                   10                  15

Ser Leu Arg

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Gly Gln Pro Arg Glu Pro Gln Val Tyr Thr Leu Pro Pro Ser Arg
1               5                   10                  15

<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Glu Pro Gln Val Tyr Thr Leu Pro Pro Ser Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Lys Asn Gln Val Ser Leu Thr Cys Leu Val Lys
1               5                   10

<210> SEQ ID NO 33
<211> LENGTH: 22
<212> TYPE: PRT
<213> ORGANISM: Artificial Sequence
<220> FEATURE:
<223> OTHER INFORMATION: Synthetic Construct

<400> SEQUENCE: 33

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 34
<211> LENGTH: 13
<212> TYPE: PRT
<213> ORGANISM: Artificial Sequence
<220> FEATURE:
<223> OTHER INFORMATION: Synthetic Construct

<400> SEQUENCE: 34

Thr Val Asp Lys Ser Arg Trp Gln Gln Gly Asn Val Phe
1               5                   10
```

```
-continued

<210> SEQ ID NO 35
<211> LENGTH: 23
<212> TYPE: PRT
<213> ORGANISM: Artificial Sequence
<220> FEATURE:
<223> OTHER INFORMATION: Synthetic Construct

<400> SEQUENCE: 35

Trp Gln Gln Gly Asn Val Phe Ser Cys Ser Val Met His Glu Ala Leu
1               5                   10                  15

His Asn His Tyr Thr Gln Lys
            20

<210> SEQ ID NO 36
<211> LENGTH: 343
<212> TYPE: PRT
<213> ORGANISM: Artificial Sequence
<220> FEATURE:
<223> OTHER INFORMATION: Synthetic Construct

<400> SEQUENCE: 36

Met Pro Asp Ser Asp Glu Arg Val Thr Pro Ala Glu Pro Leu Asp
1               5                   10                  15

Arg Met Pro Asp Pro Tyr Arg Pro Ser Tyr Gly Arg Ala Glu Thr Ile
            20                  25                  30

Val Asn Asn Tyr Ile Arg Lys Trp Gln Gln Val Tyr Ser His Arg Asp
        35                  40                  45

Gly Arg Lys Gln Gln Met Thr Glu Glu Gln Arg Glu Trp Leu Ser Tyr
    50                  55                  60

Gly Cys Val Gly Val Thr Trp Val Asn Ser Gly Gln Tyr Pro Thr Asn
65                  70                  75                  80

Arg Leu Ala Phe Ala Phe Phe Asp Glu Asp Lys Tyr Lys Asn Glu Leu
                85                  90                  95

Lys Asn Gly Arg Pro Arg Ser Gly Glu Thr Arg Ala Glu Phe Glu Gly
            100                 105                 110

Arg Val Ala Lys Asp Ser Phe Asp Glu Ala Lys Gly Phe Gln Arg Ala
        115                 120                 125

Arg Asp Val Ala Ser Val Met Asn Lys Ala Leu Glu Asn Ala His Asp
    130                 135                 140

Glu Gly Ala Tyr Leu Asp Asn Leu Lys Lys Glu Leu Ala Asn Gly Asn
145                 150                 155                 160

Asp Ala Leu Arg Asn Glu Asp Ala Arg Ser Pro Phe Tyr Ser Ala Leu
                165                 170                 175

Arg Asn Thr Pro Ser Phe Lys Asp Arg Asn Gly Gly Asn His Asp Pro
            180                 185                 190

Ser Lys Met Lys Ala Val Ile Tyr Ser Lys His Phe Trp Ser Gly Gln
        195                 200                 205

Asp Arg Ser Gly Ser Ser Asp Lys Arg Lys Tyr Gly Asp Pro Glu Ala
    210                 215                 220

Phe Arg Pro Asp Arg Gly Thr Gly Leu Val Asp Met Ser Arg Asp Arg
225                 230                 235                 240

Asn Ile Pro Arg Ser Pro Thr Ser Pro Gly Glu Ser Phe Val Asn Phe
                245                 250                 255

Asp Tyr Gly Trp Phe Gly Ala Gln Thr Glu Ala Asp Ala Asp Lys Thr
            260                 265                 270

Val Trp Thr His Gly Asn His Tyr His Ala Pro Asn Gly Ser Leu Gly
        275                 280                 285
```

Ala Met His Val Tyr Glu Ser Lys Phe Arg Asn Trp Ser Asp Gly Tyr
        290                 295                 300

Ser Asp Phe Asp Arg Gly Ala Tyr Val Val Thr Phe Val Pro Lys Ser
305                 310                 315                 320

Trp Asn Thr Ala Pro Asp Lys Val Thr Gln Gly Trp Pro Leu Glu His
                325                 330                 335

His His His His His His
        340

<210> SEQ ID NO 37
<211> LENGTH: 337
<212> TYPE: PRT
<213> ORGANISM: Artificial Sequence
<220> FEATURE:
<223> OTHER INFORMATION: Synthetic Construct

<400> SEQUENCE: 37

Arg Val Thr Pro Pro Ala Glu Pro Leu Asp Arg Met Pro Asp Pro Tyr
1               5                   10                  15

Arg Pro Ser Tyr Gly Arg Ala Glu Thr Ile Val Asn Asn Tyr Ile Arg
            20                  25                  30

Lys Trp Gln Gln Val Tyr Ser His Arg Asp Gly Arg Lys Gln Gln Met
        35                  40                  45

Thr Glu Glu Gln Arg Glu Trp Leu Ser Tyr Gly Cys Val Gly Val Thr
50                  55                  60

Trp Val Asn Ser Gly Gln Tyr Pro Thr Asn Arg Leu Ala Phe Ala Phe
65                  70                  75                  80

Phe Asp Glu Asp Lys Tyr Lys Asn Glu Leu Lys Asn Gly Arg Pro Arg
                85                  90                  95

Ser Gly Glu Thr Arg Ala Glu Phe Glu Gly Arg Val Ala Lys Asp Ser
            100                 105                 110

Phe Asp Glu Ala Lys Gly Phe Gln Arg Ala Arg Asp Val Ala Ser Val
        115                 120                 125

Met Asn Lys Ala Leu Glu Asn Ala His Asp Glu Gly Ala Tyr Leu Asp
130                 135                 140

Asn Leu Lys Lys Glu Leu Ala Asn Gly Asn Asp Ala Leu Arg Asn Glu
145                 150                 155                 160

Asp Ala Arg Ser Pro Phe Tyr Ser Ala Leu Arg Asn Thr Pro Ser Phe
                165                 170                 175

Lys Asp Arg Asn Gly Gly Asn His Asp Pro Ser Lys Met Lys Ala Val
            180                 185                 190

Ile Tyr Ser Lys His Phe Trp Ser Gly Gln Asp Arg Ser Gly Ser Ser
        195                 200                 205

Asp Lys Arg Lys Tyr Gly Asp Pro Glu Ala Phe Arg Pro Asp Arg Gly
210                 215                 220

Thr Gly Leu Val Asp Met Ser Arg Asp Arg Asn Ile Pro Arg Ser Pro
225                 230                 235                 240

Thr Ser Pro Gly Glu Ser Phe Val Asn Phe Asp Tyr Gly Trp Phe Gly
                245                 250                 255

Ala Gln Thr Glu Ala Asp Ala Asp Lys Thr Val Trp Thr His Gly Asn
            260                 265                 270

His Tyr His Ala Pro Asn Gly Ser Leu Gly Ala Met His Val Tyr Glu
        275                 280                 285

Ser Lys Phe Arg Asn Trp Ser Asp Gly Tyr Ser Asp Phe Asp Arg Gly
290                 295                 300

```
Ala Tyr Val Val Thr Phe Val Pro Lys Ser Trp Asn Thr Ala Pro Asp
305                 310                 315                 320

Lys Val Thr Gln Gly Trp Pro Leu Glu His His His His His His
                325                 330                 335

His
```

<210> SEQ ID NO 38
<211> LENGTH: 338
<212> TYPE: PRT
<213> ORGANISM: Artificial Sequence
<220> FEATURE:
<223> OTHER INFORMATION: Synthetic Construct

<400> SEQUENCE: 38

```
Pro Asp Ser Asp Glu Arg Val Thr Pro Pro Ala Glu Pro Leu Asp Arg
1               5                   10                  15

Met Pro Asp Pro Tyr Arg Pro Ser Tyr Gly Arg Ala Glu Thr Ile Val
                20                  25                  30

Asn Asn Tyr Ile Arg Lys Trp Gln Gln Val Tyr Ser His Arg Asp Gly
            35                  40                  45

Arg Lys Gln Gln Met Thr Glu Glu Gln Arg Glu Trp Leu Ser Tyr Gly
50                  55                  60

Cys Val Gly Val Thr Trp Val Asn Ser Gly Gln Tyr Pro Thr Asn Arg
65                  70                  75                  80

Leu Ala Phe Ala Phe Phe Asp Glu Asp Lys Tyr Lys Asn Glu Leu Lys
                85                  90                  95

Asn Gly Arg Pro Arg Ser Gly Glu Thr Arg Ala Glu Phe Glu Gly Arg
            100                 105                 110

Val Ala Lys Asp Ser Phe Asp Glu Ala Lys Gly Phe Gln Arg Ala Arg
        115                 120                 125

Asp Val Ala Ser Val Met Asn Lys Ala Leu Glu Asn Ala His Asp Glu
130                 135                 140

Gly Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
                165                 170                 175

Asn Thr Pro Ser Phe Lys Asp Arg Asn Gly Asn His Asp Pro Ser
            180                 185                 190

Lys Met Lys Ala Val Ile Tyr Ser Lys His Phe Trp Ser Gly Gln Asp
        195                 200                 205

Arg Ser Gly Ser Ser Asp Lys Arg Lys Tyr Gly Asp Pro Glu Ala Phe
210                 215                 220

Arg Pro Asp Arg Gly Thr Gly Leu Val Asp Met Ser Arg Asp Arg Asn
225                 230                 235                 240

Ile Pro Arg Ser Gly Glu Ser Phe Val Asn Phe Asp Tyr Gly Trp Phe
                245                 250                 255

Gly Ala Gln Thr Glu Ala Asp Ala Asp Lys Thr Val Trp Thr His Gly
            260                 265                 270

Asn His Tyr His Ala Pro Asn Gly Ser Leu Gly Ala Met His Val Tyr
        275                 280                 285

Glu Ser Lys Phe Arg Asn Trp Ser Asp Gly Tyr Ser Asp Phe Asp Arg
290                 295                 300

Gly Ala Tyr Val Val Thr Phe Val Pro Lys Ser Trp Asn Thr Ala Pro
305                 310                 315                 320
```

Asp Lys Val Thr Gln Gly Trp Pro Leu Glu His His His His His
              325                 330                 335

His His

<210> SEQ ID NO 39
<211> LENGTH: 338
<212> TYPE: PRT
<213> ORGANISM: Artificial Sequence
<220> FEATURE:
<223> OTHER INFORMATION: Synthetic Construct

<400> SEQUENCE: 39

Pro Asp Ser Asp Glu Arg Val Thr Pro Pro Ala Glu Pro Leu Asp Arg
1               5                   10                  15

Met Pro Asp Pro Tyr Arg Pro Ser Tyr Gly Arg Ala Glu Thr Ile Val
                20                  25                  30

Asn Asn Tyr Ile Arg Lys Trp Gln Gln Val Tyr Ser His Arg Asp Gly
            35                  40                  45

Arg Lys Gln Gln Met Thr Glu Glu Gln Arg Glu Trp Leu Ser Tyr Gly
    50                  55                  60

Cys Val Gly Val Thr Trp Val Asn Ser Gly Gln Tyr Pro Thr Asn Arg
65                  70                  75                  80

Leu Ala Phe Ala Phe Phe Asp Glu Asp Lys Tyr Lys Asn Glu Leu Lys
                85                  90                  95

Asn Gly Arg Pro Arg Ser Gly Glu Thr Arg Ala Glu Phe Glu Gly Arg
            100                 105                 110

Val Ala Lys Asp Ser Phe Asp Glu Ala Lys Gly Phe Gln Arg Ala Arg
    115                 120                 125

Asp Val Ala Ser Val Met Asn Lys Ala Leu Glu Asn Ala His Asp Glu
130                 135                 140

Gly Ala Tyr Leu Asp Asn Leu Lys Lys Glu Leu Ala Asn Gly Asn Asp
145                 150                 155                 160

Ala Leu Arg Asn Glu Asp Ala Arg Ser Pro Phe Tyr Ser Ala Leu Arg
                165                 170                 175

Asn Thr Pro Ser Phe Lys Asp Arg Asn Gly Gly Asn His Asp Pro Ser
            180                 185                 190

Lys Met Lys Ala Val Ile Tyr Ser Lys His Phe Trp Ser Gly Gln Asp
    195                 200                 205

Arg Ser Gly Ser Ser Asp Lys Arg Lys Tyr Gly Asp Pro Glu Ala Phe
210                 215                 220

Arg Pro Asp Arg Gly Thr Gly Leu Val Asp Met Ser Arg Asp Arg Asn
225                 230                 235                 240

Ile Pro Arg Ser Pro Thr Ser Pro Gly Glu Ser Phe Val Asn Phe Asp
                245                 250                 255

Tyr Gly Trp Phe Gly Ala Gln Thr Glu Ala Asp Ala Asp Lys Thr Val
            260                 265                 270

Trp Thr His Gly Asn His Tyr His Ala Pro Gly Ala Met His Val Tyr
    275                 280                 285

Glu Ser Lys Phe Arg Asn Trp Ser Asp Gly Tyr Ser Asp Phe Asp Arg
290                 295                 300

Gly Ala Tyr Val Val Thr Phe Val Pro Lys Ser Trp Asn Thr Ala Pro
305                 310                 315                 320

Asp Lys Val Thr Gln Gly Trp Pro Leu Glu His His His His His His
                325                 330                 335

His His

<210> SEQ ID NO 40
<211> LENGTH: 333
<212> TYPE: PRT
<213> ORGANISM: Artificial Sequence
<220> FEATURE:
<223> OTHER INFORMATION: Synthetic Construct

<400> SEQUENCE: 40

```
Arg Val Thr Pro Pro Ala Glu Pro Leu Asp Arg Met Pro Asp Pro Tyr
1               5                   10                  15

Arg Pro Ser Tyr Gly Arg Ala Glu Thr Ile Val Asn Asn Tyr Ile Arg
            20                  25                  30

Lys Trp Gln Gln Val Tyr Ser His Arg Asp Gly Arg Lys Gln Gln Met
        35                  40                  45

Thr Glu Glu Gln Arg Glu Trp Leu Ser Tyr Gly Cys Val Gly Val Thr
    50                  55                  60

Trp Val Asn Ser Gly Gln Tyr Pro Thr Asn Arg Leu Ala Phe Ala Phe
65                  70                  75                  80

Phe Asp Glu Asp Lys Tyr Lys Asn Glu Leu Lys Asn Gly Arg Pro Arg
                85                  90                  95

Ser Gly Glu Thr Arg Ala Glu Phe Glu Gly Arg Val Ala Lys Asp Ser
            100                 105                 110

Phe Asp Glu Ala Lys Gly Phe Gln Arg Ala Arg Asp Val Ala Ser Val
        115                 120                 125

Met Asn Lys Ala Leu Glu Asn Ala His Asp Glu Gly Ala Tyr Leu Asp
    130                 135                 140

Asn Leu Lys Lys Glu Leu Ala Asn Gly Asn Asp Ala Leu Arg Asn Glu
145                 150                 155                 160

Asp Ala Arg Ser Pro Phe Tyr Ser Ala Leu Arg Asn Thr Pro Ser Phe
                165                 170                 175

Lys Asp Arg Asn Gly Gly Asn His Asp Pro Ser Lys Met Lys Ala Val
            180                 185                 190

Ile Tyr Ser Lys His Phe Trp Ser Gly Gln Asp Arg Ser Gly Ser Ser
        195                 200                 205

Asp Lys Arg Lys Tyr Gly Asp Pro Glu Ala Phe Arg Pro Asp Arg Gly
    210                 215                 220

Thr Gly Leu Val Asp Met Ser Arg Asp Arg Asn Ile Pro Arg Ser Pro
225                 230                 235                 240

Thr Ser Pro Gly Glu Ser Phe Val Asn Phe Asp Tyr Gly Trp Phe Gly
                245                 250                 255

Ala Gln Thr Glu Ala Asp Ala Asp Lys Thr Val Trp Thr His Gly Asn
            260                 265                 270

His Tyr His Ala Pro Gly Ala Met His Val Tyr Glu Ser Lys Phe Arg
        275                 280                 285

Asn Trp Ser Asp Gly Tyr Ser Asp Phe Asp Arg Gly Ala Tyr Val Val
    290                 295                 300

Thr Phe Val Pro Lys Ser Trp Asn Thr Ala Pro Asp Lys Val Thr Gln
305                 310                 315                 320

Gly Trp Pro Leu Glu His His His His His His His
                325                 330
```

<210> SEQ ID NO 41
<211> LENGTH: 329
<212> TYPE: PRT
<213> ORGANISM: Artificial Sequence
<220> FEATURE:
<223> OTHER INFORMATION: Synthetic Construct

<400> SEQUENCE: 41

```
Arg Val Thr Pro Pro Ala Glu Pro Leu Asp Arg Met Pro Asp Pro Tyr
1               5                   10                  15
Arg Pro Ser Tyr Gly Arg Ala Glu Thr Ile Val Asn Asn Tyr Ile Arg
            20                  25                  30
Lys Trp Gln Gln Val Tyr Ser His Arg Asp Gly Arg Lys Gln Gln Met
        35                  40                  45
Thr Glu Glu Gln Arg Glu Trp Leu Ser Tyr Gly Cys Val Gly Val Thr
    50                  55                  60
Trp Val Asn Ser Gly Gln Tyr Pro Thr Asn Arg Leu Ala Phe Ala Phe
65                  70                  75                  80
Phe Asp Glu Asp Lys Tyr Lys Asn Glu Leu Lys Asn Gly Arg Pro Arg
                85                  90                  95
Ser Gly Glu Thr Arg Ala Glu Phe Glu Gly Arg Val Ala Lys Asp Ser
            100                 105                 110
Phe Asp Glu Ala Lys Gly Phe Gln Arg Ala Arg Asp Val Ala Ser Val
        115                 120                 125
Met Asn Lys Ala Leu Glu Asn Ala His Asp Glu Gly Ala Tyr Leu Asp
    130                 135                 140
Asn Leu Lys Lys Glu Leu Ala Asn Gly Asn Asp Ala Leu Arg Asn Glu
145                 150                 155                 160
Asp Ala Arg Ser Pro Phe Tyr Ser Ala Leu Arg Asn Thr Pro Ser Phe
                165                 170                 175
Lys Asp Arg Asn Gly Gly Asn His Asp Pro Ser Lys Met Lys Ala Val
            180                 185                 190
Ile Tyr Ser Lys His Phe Trp Ser Gly Gln Asp Arg Ser Gly Ser Ser
        195                 200                 205
Asp Lys Arg Lys Tyr Gly Asp Pro Glu Ala Phe Arg Pro Asp Arg Gly
    210                 215                 220
Thr Gly Leu Val Asp Met Ser Arg Asp Arg Asn Ile Pro Arg Ser Gly
225                 230                 235                 240
Glu Ser Phe Val Asn Phe Asp Tyr Gly Trp Phe Gly Ala Gln Thr Glu
                245                 250                 255
Ala Asp Ala Asp Lys Thr Val Trp Thr His Gly Asn His Tyr His Ala
            260                 265                 270
Pro Gly Ala Met His Val Tyr Glu Ser Lys Phe Arg Asn Trp Ser Asp
        275                 280                 285
Gly Tyr Ser Asp Phe Asp Arg Gly Ala Tyr Val Val Thr Phe Val Pro
    290                 295                 300
Lys Ser Trp Asn Thr Ala Pro Asp Lys Val Thr Gln Gly Trp Pro Leu
305                 310                 315                 320
Glu His His His His His His His
                325
```

<210> SEQ ID NO 42
<211> LENGTH: 329
<212> TYPE: PRT
<213> ORGANISM: Artificial Sequence
<220> FEATURE:
<223> OTHER INFORMATION: Synthetic Construct

<400> SEQUENCE: 42

```
Arg Val Thr Pro Pro Ala Glu Pro Leu Asp Arg Met Pro Asp Pro Tyr
1               5                   10                  15
Arg Pro Ser Tyr Gly Arg Ala Glu Thr Ile Val Asn Asn Tyr Ile Arg
            20                  25                  30
Lys Trp Gln Gln Val Tyr Ser His Arg Asp Gly Arg Lys Gln Gln Met
        35                  40                  45
Thr Glu Glu Gln Arg Glu Trp Leu Ser Tyr Gly Cys Val Gly Val Thr
    50                  55                  60
Trp Val Asn Ser Gly Gln Tyr Pro Thr Asn Arg Leu Ala Phe Ala Phe
65                  70                  75                  80
Phe Asp Glu Asp Lys Tyr Lys Asn Glu Leu Lys Asn Gly Arg Pro Arg
                85                  90                  95
Ser Gly Glu Thr Arg Ala Glu Phe Glu Gly Arg Val Ala Lys Asp Ser
            100                 105                 110
Phe Asp Glu Ala Lys Gly Phe Gln Arg Ala Arg Asp Val Ala Ser Val
        115                 120                 125
Met Asn Lys Ala Leu Glu Asn Ala His Asp Glu Gly Ala Tyr Leu Asp
    130                 135                 140
Asn Leu Lys Lys Glu Leu Ala Asn Gly Asn Asp Ala Leu Arg Asn Glu
145                 150                 155                 160
Asp Ala Arg Ser Pro Phe Tyr Ser Ala Leu Arg Asn Thr Pro Ser Phe
                165                 170                 175
Lys Asp Arg Asn Gly Gly Asn His Asp Pro Ser Lys Met Lys Ala Val
            180                 185                 190
Ile Tyr Ser Lys His Phe Trp Ser Gly Gln Asp Arg Ser Gly Ser Ser
        195                 200                 205
Asp Lys Arg Lys Tyr Gly Asp Pro Glu Ala Phe Arg Pro Asp Arg Gly
    210                 215                 220
Thr Gly Leu Val Asp Met Ser Arg Asp Arg Asn Ile Pro Arg Ser Pro
225                 230                 235                 240
Thr Ser Pro Gly Glu Ser Phe Val Asn Phe Asp Tyr Gly Trp Phe Gly
                245                 250                 255
Ala Gln Thr Glu Ala Asp Ala Asp Lys Thr Val Trp Thr His Gly Asn
            260                 265                 270
His Tyr Gly Met His Val Tyr Glu Ser Lys Phe Arg Asn Trp Ser Asp
        275                 280                 285
Gly Tyr Ser Asp Phe Asp Arg Gly Ala Tyr Val Val Thr Phe Val Pro
    290                 295                 300
Lys Ser Trp Asn Thr Ala Pro Asp Lys Val Thr Gln Gly Trp Pro Leu
305                 310                 315                 320
Glu His His His His His His His
                325
```

<210> SEQ ID NO 43
<211> LENGTH: 328
<212> TYPE: PRT
<213> ORGANISM: Artificial Sequence
<220> FEATURE:
<223> OTHER INFORMATION: Synthetic Construct

```
<400> SEQUENCE: 43

Arg Val Thr Pro Pro Ala Glu Pro Leu Asp Arg Met Pro Asp Pro Tyr
1               5                   10                  15

Arg Pro Ser Tyr Gly Arg Ala Glu Thr Ile Val Asn Asn Tyr Ile Arg
            20                  25                  30

Lys Trp Gln Gln Val Tyr Ser His Arg Asp Gly Arg Lys Gln Gln Met
            35                  40                  45

Thr Glu Glu Gln Arg Glu Trp Leu Ser Tyr Gly Cys Val Gly Val Thr
    50                  55                  60

Trp Val Asn Ser Gly Gln Tyr Pro Thr Asn Arg Leu Ala Phe Ala Phe
65                  70                  75                  80

Phe Asp Glu Asp Lys Tyr Lys Asn Glu Leu Lys Asn Gly Arg Pro Arg
                85                  90                  95

Ser Gly Glu Thr Arg Ala Glu Phe Glu Gly Arg Val Ala Lys Asp Ser
                100                 105                 110

Phe Asp Glu Ala Lys Gly Phe Gln Arg Ala Arg Asp Val Ala Ser Val
            115                 120                 125

Met Asn Lys Ala Leu Glu Asn Ala His Asp Glu Gly Ala Tyr Leu Asp
    130                 135                 140

Asn Leu Lys Lys Glu Leu Ala Asn Gly Asn Asp Ala Leu Arg Asn Glu
145                 150                 155                 160

Asp Ala Arg Ser Pro Phe Tyr Ser Ala Leu Arg Asn Thr Pro Ser Phe
                165                 170                 175

Lys Asp Arg Asn Gly Gly Asn His Asp Pro Ser Lys Met Lys Ala Val
            180                 185                 190

Ile Tyr Ser Lys His Phe Trp Ser Gly Gln Asp Arg Ser Gly Ser Ser
        195                 200                 205

Asp Lys Arg Lys Tyr Gly Asp Pro Glu Ala Phe Arg Pro Asp Arg Gly
        210                 215                 220

Thr Gly Leu Val Asp Met Ser Arg Asp Arg Asn Ile Pro Arg Ser Pro
225                 230                 235                 240

Thr Ser Pro Gly Glu Ser Phe Val Asn Phe Asp Tyr Gly Trp Phe Gly
                245                 250                 255

Ala Gln Thr Glu Ala Asp Ala Asp Lys Thr Val Trp Thr His Gly Asn
            260                 265                 270

His Tyr His Gly Val Tyr Glu Ser Lys Phe Arg Asn Trp Ser Asp Gly
        275                 280                 285

Tyr Ser Asp Phe Asp Arg Gly Ala Tyr Val Val Thr Phe Val Pro Lys
        290                 295                 300

Ser Trp Asn Thr Ala Pro Asp Lys Val Thr Gln Gly Trp Pro Leu Glu
305                 310                 315                 320

His His His His His His His
                325
```

HOMOGENOUS ANTIBODY DRUG CONJUGATES VIA ENZYMATIC METHODS

CROSS-REFERENCE TO RELATED APPLICATIONS

This application is divisional of U.S. patent application Ser. No. 15/317,907, filed on Dec. 9, 2016, which is a National Phase application under 35 U.S.C. § 371 of International Application No. PCT/US2015/035375, filed on Jun. 11, 2015, which claims the priority benefit of U.S. Provisional Application No. 62/011,534, filed on Jun. 12, 2014, the disclosures of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 720692000110SEQLISTING.txt, date recorded: May 22, 2018, size: 51 KB).

BACKGROUND

Antibody-based therapeutics have played an important role in targeted therapy for various disorders, such as cancers and immunological diseases. In recent years, antibody drug conjugates (ADC) have been explored extensively for effective delivery of drugs to target sites. For example, chemical modification has been widely used for conjugating drugs to antibodies either through lysine side chain amines or through cysteine sulfhydryl groups. However, these conjugation methods frequently led to a heterogeneous mixture of conjugates having different molar ratios of drug to antibody, non-specific conjugation sites, as well as different efficiency, safety, and pharmacokinetics. See Tanaka et al, FEBS Letters 579:2092-2096 (2005). Reactive cysteine residues engineered at specific sites of antibodies for specific drug conjugation with defined stoichiometry has also been made. See Junutula et al., Nature Biotechnology, 26: 925-932 (2008). However, expression and conjugation of such cysteine engineered antibodies and antibody-drug conjugates require lengthy and complicated reaction procedures. See, e.g., Gomez et al., Biotechnology and Bioengineering, 105(4): 748-760 (2009). Antibody aggregates may also be generated during the process of making the cysteine engineered antibodies and the antibody-drug conjugates. Unnatural amino acid residues have also been incorporated into antibodies as chemical handles for site-specific conjugation. See Axupa et al., PNAS, 109: 16101-16106 (2012). To implement this methodology, an orthogonal pair of amber suppressor tRNA and aminoacyl-tRNA synthetase has to be integrated into an expression host first. Then, the mutant antibody can be expressed in this special host with medium supplement of the unnatural amino acid. This process is not only time consuming, but also very low in antibody expression yield.

Recently, enzymatic approaches to making ADCs using a transglutaminase have been explored. Transglutaminases (TGase) transfers a moiety having an amine donor group to an acceptor glutamine residue through transglutamination. Full-length IgG antibodies of human isotype contain a conserved glutamine residue at position 295 of the heavy chain (Q295). Because this glutamine residue is in close proximity to an N-glycosylation site (N297), it was generally believed that Q295 on the full length antibody is inaccessible to TGase when the antibody is N-glycosylated. To allow TGase acting on full length antibodies, the Fc region of the antibody was deglycosylated or mutated to remove the N-glycosylation site prior to the TGase-mediated conjugation. See WO2013/092998. Alternatively, glutamine-containing sequence "tags" have been inserted into the antibodies' light or heavy chains to provide acceptor glutamine sites. See WO2012059882. Hence, all current site-specific ADC technologies rely on engineered antibody mutants, which may result in potential immunogenicity and in vivo instability. There is a strong need for an efficient site-specific antibody conjugation tool where intact antibody can be used directly.

All publications, patents, and patent applications cited herein are hereby incorporated by reference herein in their entirety.

SUMMARY OF THE INVENTION

The present invention in one aspect provides an Fc-containing polypeptide conjugate comprising an Fc-containing polypeptide site-specifically conjugated to a conjugate moiety, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue.

In some embodiments, the acceptor glutamine residue is flanked by an N-glycosylation site at +2 position relative to the glutamine residue. In some embodiments, the N-glycosylated Fc region comprises the amino acids 290 to 300 of an immunoglobulin heavy chain, wherein the numbering is according to the Kabat index. In some embodiments, the N-glycosylated Fc region is the Fc region of a naturally occurring immunoglobulin heavy chain.

In some embodiments according to any one of the embodiments above, the immunoglobulin is selected from the group consisting of IgG1, IgG2, IgG3, and IgG4. In some embodiments, the Fc-containing polypeptide is an immunoglobulin heavy chain. In some embodiments, the Fc-containing polypeptide is a full length antibody. In some embodiments, the antibody is a human or humanized antibody. In some embodiments, both heavy chains of the antibody are conjugated to the conjugate moiety. In some embodiments, the acceptor glutamine residue is at position 295 and the N-glycosylation site is at position 297, wherein the numbering is according to the Kabat index.

In some embodiments according to any of the embodiments above, the conjugate moiety comprises an active moiety selected from the group consisting of: a moiety that improves the pharmacokinetic property of the Fc-containing polypeptide, a therapeutic moiety, and a diagnostic moiety. In some embodiments, the active moiety is a toxin.

In some embodiments according to any of the embodiments above, the Fc-containing polypeptide and the conjugate moiety are conjugated via a linker, such as a cleavage linker or a non-cleavable linker.

In some embodiments, there is provided a composition comprising any one of the Fc-containing polypeptide conjugate described above, wherein at least about 50% (for example at least about any of 60%, 70%, 80%, 90%, or 95%) of the Fc-containing polypeptide conjugates in the composition is glycosylated in the Fc region. In some embodiments, at least about 50% (for example at least about any of 60%, 70%, 80%, 90%, or 95%) of the Fc-containing polypeptide conjugates has the Fc-containing polypeptide to conjugate moiety molar ratio of 1:1 or 1:2.

In one aspect, there is provided an antibody drug conjugate comprising an antibody conjugated to a conjugation moiety via an endogenous acceptor glutamine residue on the antibody, wherein the antibody drug conjugate is glycosylated in the Fc region. In some embodiments, the antibody drug conjugate is N-glycosylated in the Fc region. In some embodiments, the antibody is a human antibody. In some embodiments, the antibody is a humanized antibody.

In some embodiments according to any one of the antibody drug conjugates described above, both heavy chains of the antibody are conjugated to the conjugate moiety.

In some embodiments according to any one of the antibody drug conjugates described above, the conjugate moiety comprises an active moiety selected from the group consisting of: a moiety that improves the pharmacokinetic property of the antibody, a therapeutic moiety, and a diagnostic moiety. In some embodiments, the active moiety is a toxin.

In some embodiments according to any one of the antibody drug conjugates described above, the antibody and the conjugate moiety are conjugated via a linker. In some embodiments, the linker is a cleavable linker. In some embodiments, the linker is a non-cleavable linker.

In some embodiments, there is provided a composition comprising any one of the antibody drug conjugates described above, wherein at least about 50% (for example, at least about any of 60%, 70%, 80%, 90%, or 95%) of antibody drug conjugates in the composition is glycosylated in the Fc region. In some embodiments, at least 80% of the antibody drug conjugates in the composition has the antibody to conjugate moiety molar ratio of 1:1 or 1:2.

In another aspect, there is provided a method of making an Fc-containing polypeptide conjugate comprising an Fc-containing polypeptide specifically conjugated to a conjugate moiety comprising: reacting the Fc-containing polypeptide with the conjugate moiety in the presence of a transglutaminase under a condition that is sufficient to generate the Fc-containing polypeptide conjugate, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue.

In some embodiments, there is provided a method of making an Fc-containing polypeptide conjugate comprising an Fc-containing polypeptide specifically conjugated to a conjugate moiety comprising a small molecule handle and an active moiety comprising: a) reacting the Fc-containing polypeptide with the small molecule handle in the presence of a transglutaminase under a condition that is sufficient to generate an intermediate conjugate comprising an Fc-containing polypeptide specifically conjugated to the small molecule handle, and b) coupling the intermediate conjugate with an active moiety thereby obtaining the Fc-containing polypeptide conjugate, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue. In some embodiments, the transglutaminase is a wildtype transglutaminase having the amino acid sequence of SEQ ID NO:16. In some embodiments, the transglutaminase is an engineered transglutaminase, such as an engineered transglutaminase comprising an amino acid sequence having at least about 80% (for example, at least about 85%, 90%, 95%, or 99%) identity to SEQ ID NO:16. In some embodiments, the molar ratio of the transglutaminase and the Fc-containing polypeptide is about 10:1 to about 1:100. In some embodiments, the transglutaminase is immobilized on a solid support. In other embodiments, the Fc-containing polypeptide is immobilized on a solid support.

In some embodiments according to any one of the methods described above, the acceptor glutamine residue is flanked by an N-glycosylation site at +2 position relative to the glutamine residue. In some embodiments, the N-glycosylated Fc region comprises the amino acids 290 to 300 of an immunoglobulin heavy chain, wherein the numbering is according to the Kabat index. In some embodiments, the N-glycosylated Fc region is the Fc region of a wildtype immunoglobulin heavy chain. In some embodiments, the immunoglobulin is selected from the group consisting of IgG1, IgG2, IgG3, and IgG4. In some embodiments, the Fc-containing polypeptide is an immunoglobulin heavy chain, such as a full length antibody, for example a human antibody or a humanized antibody. In some embodiments, both heavy chains of the antibody are conjugated to the conjugate moiety. In some embodiments, the acceptor glutamine residue is at position 295 and the N-glycosylation site is at position 297, wherein the numbering is according to the Kabat numbering.

In some embodiments according to any one of the methods described above, the conjugate moiety comprises an active moiety selected from the group consisting of: a moiety that improves the pharmacokinetic property of the Fc-containing polypeptide, a therapeutic moiety, and a diagnostic moiety. In some embodiments, the active moiety is a toxin.

In another aspect, there is provided a method of making an antibody drug conjugate comprising contacting an antibody composition with the conjugate moiety in the presence of a transglutaminase under a condition sufficient to generate the antibody drug conjugate, wherein at least about 50% (for example, at least about any of 60%, 70%, 80%, 90%, or 95%) of the antibody in the composition is glycosylated in the Fc-region, and wherein the conjugate moiety is conjugated to the endogenous acceptor glutamine residue on the antibody.

In another aspect, there is provided a method of making an antibody drug conjugate comprising antibody specifically conjugated to a conjugate moiety comprising a small molecule handle and an active moiety comprising a) contacting an antibody composition with the small molecule handle in the presence of a transglutaminase under a condition sufficient to generate an intermediate conjugate comprising an antibody specifically conjugated to the small molecule handle, and b) contacting the intermediate conjugate with an active moiety thereby obtaining the antibody drug conjugate, wherein at least about 50% (for example, at least about any of 60%, 70%, 80%, 90%, or 95%) of the antibody in the composition is glycosylated in the Fc-region, and wherein the conjugate moiety is conjugated to the endogenous acceptor glutamine residue on the antibody.

In some embodiments according to any one of the methods of making an antibody drug conjugate described above, the transglutaminase is a wildtype transglutaminase. In some embodiments, the wildtype transglutaminase has the amino acid sequence of SEQ ID NO:16.

In some embodiments according to any one of the methods of making an antibody drug conjugate described above, the transglutaminase is an engineered transglutaminase. In some embodiments, the engineered transglutaminase comprises an amino acid sequence having at least about 80% (for example, at least about 85%, 90%, 95%, or 99%) identity to SEQ ID NO:16.

In some embodiments according to any one of the methods of making an antibody drug conjugate described above, the transglutaminase has a purity of at least about 90% (for example, at least about any of 95%, 98%, or 99%).

In some embodiments according to any one of the methods of making an antibody drug conjugate described above, the molar ratio of the transglutaminase and the antibody composition is about 10:1 to about 1:10.

In some embodiments according to any one of the methods of making an antibody drug conjugate described above, the transglutaminase is immobilized on a solid support.

In some embodiments according to any one of the methods of making an antibody drug conjugate described above, the antibody is immobilized on a solid support.

In some embodiments according to any one of the methods of making an antibody drug conjugate described above, the antibody is a human or humanized antibody.

In some embodiments according to any one of the methods of making an antibody drug conjugate described above, the conjugate moiety comprises an active moiety selected from the group consisting of: a moiety that improves the pharmacokinetic property of the antibody composition, a therapeutic moiety, and a diagnostic moiety. In some embodiments, the active moiety is a toxin.

In another aspect, there are provided engineered transglutaminases. In some embodiments, there is provided an engineered transglutaminase capable of conjugating an Fc-containing polypeptide (such as an antibody) to a conjugate moiety, wherein the Fc-containing polypeptide (such as the antibody) comprises an N-glycosylated Fc region, wherein the N-glycosylated Fc region comprises an acceptor glutamine residue flanked by an N-glycosylation site, wherein upon reaction the conjugate moiety is conjugated to the Fc-containing polypeptide (such as the antibody) via the acceptor glutamine residue, and wherein the conjugation is at least about 10% (for example, at least about any of 20%, 30%, 40%, 50% or more) more active than a wildtype transglutaminase under the same reaction conditions. In some embodiments, there is provided an engineered transglutaminase comprising an amino acid sequence having at least about 80% (for example, at least about 85%, 90%, 95%, or 99%) identity to SEQ ID NO:16, wherein the transglutaminase comprises a deletion selected from the group consisting of: D1-E4; P244-P247; and N282-L285.

Further provided are methods of making Fc-containing polypeptide conjugates (such as antibody drug conjugates) by using the engineered transglutaminases described herein.

In some embodiments, there is provided a method of making an antibody drug conjugate comprising an antibody specifically conjugated to a conjugate moiety comprising: contacting an antibody composition with the conjugate moiety in the presence of any one of the engineered transglutaminases described above under a condition sufficient to generate the antibody drug conjugate, wherein the conjugate moiety is conjugated to the endogenous acceptor glutamine residue on the antibody.

In some embodiments, there is provided a method of making an antibody drug conjugate comprising an antibody specifically conjugated to a conjugate moiety comprising a small molecule handle and an active moiety comprising: a) contacting an antibody composition with the small molecule handle in the presence of any one of the engineered transglutaminases described above under a condition sufficient to generate an intermediate conjugate comprising an antibody specifically conjugated to the small molecule handle, and b) contacting the intermediate conjugate with an active moiety thereby obtaining the antibody drug conjugate, wherein the conjugate moiety is conjugated to the endogenous acceptor glutamine residue on the antibody.

It is to be understood that one, some, or all of the properties of the various embodiments described herein may be combined to form other embodiments of the present invention. These and other aspects of the invention will become apparent to one of skill in the art.

BRIEF DESCRIPTION OF THE FIGURES

FIG. 1 provides sequence alignments of the CH2 domain sequences of various types of human, mouse, and rat IgGs. The endogenous glutamine (Q295) for TGase-mediated reaction and the N-glycosylation site (N297) are boxed.

FIG. 2 provides the alignment of amino acid sequence of TGases from *Strep Ladakanum* (TG_SL, SEQ ID NO:16) and *Strep Mobaraensis* (TG_SM, SEQ ID NO:18). The consensus sequence is SEQ ID NO:19.

FIG. 3 provides sequences of deletion mutants based on TGases from *Strep Ladakanum*. The sequence of a recombinant wildtype TG_SL is shown (SEQ ID NO:17).

FIG. 6 provides HPLC chromatograms for IgG1, 2 and 4 conjugated with MDC. FIG. 6, panel A shows conjugation of only the heavy chain of IgG1 with MDC. FIG. 6, panel B shows conjugation of IgG1 with MDC in a molar ratio of 1:1 and 1:2. FIG. 6, panel C shows site specific conjugation of IgG2 (left) and IgG4 (right) with MDC.

FIG. 12 provides monomethyl auristatin E (MMAE) derivatives containing a non-cleavable linker with variable number of polyethylene glycol (PEG) units (top panel), referred herein as PEGx-MMAE, wherein x is 2, 4, 6, 8, 10, 12, 16, 20 or 24; and an MMAE derivative containing a cleavable linker (bottom panel), referred herein as PEG3c-MMAE.

FIG. 18 provides a group of 3-arm PEG linkers (top panel; 1 to 5 k Da) each with one amine group and two azide groups, and Alkyne-PEG4c-MMAE (bottom panel) used in DAR4 ADC preparation.

DETAILED DESCRIPTION

Figure 4:
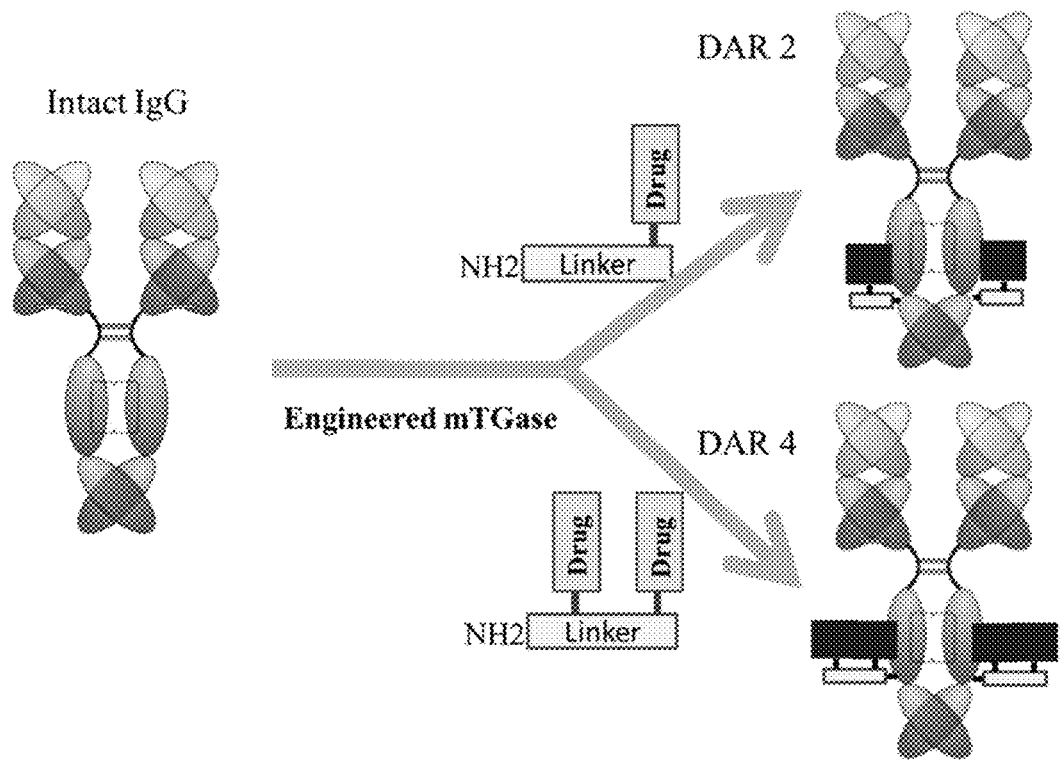
FIG. 4 provides a diagram showing a one-step antibody-drug conjugation method.

The present application for the first time provides methods of attaching a conjugate moiety (such as a drug) to an intact, unmodified (e.g., glycosylation configuration left unaltered) antibody in a site-specific and stoichiometric fashion. This is accomplished either by utilizing a wildtype TGase under a specific reaction condition and/or through an engineered TGase that is specifically designed to carry out site-specific conjugation at an endogenous glutamine residue in the Fc region. The methods of the present application allow for the production of a homogeneous site-specific and stoichiometric antibody drug conjugate which would offer superior PK profile, broad therapeutic index, and optimal potency. The methods allow conjugation of a drug to an intact antibody without introducing mutations and/or deglycosylating the antibody, thus minimize immunogenicity introduced by such extra steps of manipulations. The glycans on the intact antibody, when present, protect the antibody from degradation, leading to more stable antibody-drug conjugates. As no manipulation of the antibody was necessary prior to the transglutamination reactions, the TGase-based antibody conjugation methods described herein are significantly more efficient than those reported previously.

Thus, the present application in one aspect provides Fc-containing polypeptide conjugates (such as antibody drug conjugate) comprising an Fc-containing polypeptide (such as antibody) conjugated to a conjugate moiety, wherein the Fc-containing polypeptide (such as antibody) comprises an N-glycosylated Fc region comprising an acceptor glutamine residue flanked by an N-glycosylation site, and wherein the conjugate moiety is conjugated to the Fc-containing polypeptide (such as antibody) via the acceptor glutamine residue.

In another aspect, there are provided methods of making Fc-containing polypeptide conjugates (such as antibody drug conjugates) by using a wildtype or engineered transglutaminase.

Further provided are engineered transglutaminases specifically designed for carrying out such reactions.

Definitions

"Transglutaminase," used interchangeably herein with "TGase," refers to an enzyme capable of carrying out tranglutamination reactions. The term "transglutamination" as used herein refers to a reaction where the γ-glutaminyl of an acceptor glutamine residue from a protein/peptide is transferred to an amine group, such as a primary amine or the ε-amino group of lysine.

The term "acceptor glutamine residue," when referring to an amino acid residue of a polypeptide or protein, refers to a glutamine residue that, under suitable conditions, is recognized by a TGase and can be crosslinked to a conjugate moiety comprising a donor amine group by a TGase through a reaction between the glutamine and a donor amine group (such as lysine or a structurally related primary amine such as amino pentyl group).

An "endogenous acceptor glutamine residue on an antibody" used herein refers to an acceptor glutamine residue in a naturally occurring antibody Fc region. Such endogenous acceptor glutamine residue is typically Q295 by the Kabat numbering and flanked by an N-glycosylation site at Asn297 position.

"Fc-containing polypeptide" used herein refers to a polypeptide (e.g., an antibody or an Fc fusion protein) comprising the Fc region of an immunoglobulin heavy chain. The term "polypeptide" used herein includes both single polypeptide chain and multiunit polypeptides. For example, Fc-containing polypeptide can be a full length antibody (such as an intact antibody), or it can be a single chain of the full length antibody.

"Fc region" as used herein refers to the polypeptide comprising the constant region of an antibody heavy chain excluding the first constant region immunoglobulin domain. For IgG, the Fc region may comprise immunoglobulin domains CH2 and CH3 and the hinge between CH1 and CH2.

"Full length antibody" as used herein refers to a molecule that constitutes the natural biological form of an antibody, including variable and constant regions. For example, in most mammals, including humans and mice, the full length antibody of the IgG isotype is a tetramer and consists of two identical pairs of two immunoglobulin chains, each pair having one light and one heavy chain, each light chain comprising immunoglobulin domains VL and CL, and each heavy chain comprising immunoglobulin domains VH, CH1, CH2, and CH3. In some mammals, for example in camels and llamas, IgG antibodies may consist of only two heavy chains, each heavy chain comprising a variable domain attached to the Fc region.

By "amino acid modification" herein is meant an amino acid substitution, insertion, and/or deletion in a polypeptide sequence. By "amino acid substitution" or "substitution" herein is meant the replacement of an amino acid at a given position in a protein sequence with another amino acid. A "variant" of a polypeptide refers to a polypeptide having an amino acid sequence that is substantially identical to a reference polypeptide, typically a native or "parent" polypeptide. The polypeptide variant may possess one or more amino acid substitutions, deletions, and/or insertions at certain positions within the native amino acid sequence.

"Conservative" amino acid substitutions are those in which an amino acid residue is replaced with an amino acid residue having a side chain with similar physicochemical properties. Families of amino acid residues having similar side chains are known in the art, and include amino acids with basic side chains (e.g., lysine, arginine, histidine), acidic side chains (e.g., aspartic acid, glutamic acid), uncharged polar side chains (e.g., glycine, asparagine, acceptor glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

The term "protecting group" refers to a group that temporarily protects or blocks, i.e., intended to prevent from reacting, a functional group, e.g., an amino group, a hydroxyl group, or a carboxyl group, during the transformation of a first molecule to a second molecule.

The phrase "moiety that improves the pharmacokinetic properties" refers to a moiety that changes the pharmacokinetic properties of the molecule that the moiety is attached to in such a way that a better therapeutic or diagnostic effect can be obtained. The moiety can for example increase the water solubility, increase the circulation time, or reduce immunogenicity.

The phrase "linker" refers to a structural element of a compound that links one structural element of said compound to one or more other structural elements of said same compound.

As used herein, "treating" or "treatment" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the recurrence of the disease, delaying or slowing the progression of the disease, ameliorating the disease state, providing a remission (partial or total) of the disease, decreasing the dose of one or more other medications required to treat the disease, delaying the progression of the disease, and/or increasing quality of life.

The term "individual" refers to a mammal and includes, but is not limited to, human, bovine, horse, feline, canine, rodent, or primate. In some embodiments, the individual is human.

It is understood that aspects and embodiments of the invention described herein include "consisting of" and "consisting essentially of" aspects and embodiments.

Reference to "about" a value or parameter herein includes (and describes) variations that are directed to that value or parameter per se. For example, description referring to "about X" includes description of "X." The term "about X-Y" used herein has the same meaning as "about X to about Y."

As used herein and in the appended claims, the singular forms "a," "or," and "the" include plural referents unless the context clearly dictates otherwise.

Fc-Containing Polypeptide Conjugates

The present application in one aspect provides an Fc-containing polypeptide conjugate (such as an antibody drug conjugate) comprising an Fc-containing polypeptide (such as an antibody) site-specifically conjugated to a conjugate moiety. The Fc-containing polypeptide (such as antibody) comprises an N-glycosylated Fc region. The N-glycosylated Fc region comprises an acceptor glutamine residue flanked by an N-glycosylation site, and the conjugate moiety is conjugated to the Fc-containing polypeptide (such as antibody) via the acceptor glutamine residue.

The Fc region of an immunoglobulin in some embodiments comprises part or all of the hinge region. In some embodiments the Fc-containing polypeptide comprises the Fc region of a naturally occurring immunoglobulin. In some embodiments, the Fc-containing polypeptide comprising an Fc region of IgG1, IgG2, IgG3, IgG4 subtypes, or from IgA, IgE, IgD, or IgM. In some embodiments, the Fc region is from human IgG, and the Fc region is from an amino acid residue at position Glu216 or Ala231 to the carboxyl-terminus thereof according to the Kabat numbering system.

In some embodiments, the Fc-containing polypeptide is an Fc-containing fusion polypeptide wherein one or more functional polypeptides are fused to the Fc region. Such functional polypeptides include, but are not limited to, the target-binding region of a receptor, an adhesion molecule, a ligand, an enzyme, a cytokine, and a chemokine.

The Fc regions described herein can be N-glycosylated. For example, in some embodiments, the polysaccharide chain attached at the N-glycosylation site is at least about any of 1, 10, 20, 30, 40, 50, 60, 70, 80, 90, or 100 units.

The N-glycosylation site flanks the acceptor glutamine residue to which the conjugate moiety is attached. The inventor has for the first time demonstrated that, through methods described further herein, it is possible to attach a conjugate moiety to an acceptor glutamine residue flanked by an N-glycosylation site in the Fc-region. In some embodiments, the N-glycosylation site and the acceptor glutamine residue are 5 or less amino acid residues apart. In some embodiments, the N-glycosylation site and the acceptor glutamine are 5, 4, 3, 2, or 1 amino acids apart. In some embodiments, the N-glycosylation site and the acceptor glutamine are next to each other. In some embodiments, the acceptor glutamine residue is flanked by an N-glycosylation site at +2 position relative to the glutamine residue. In some embodiments, the acceptor glutamine residue is flanked by an N-glycosylation site at +1, +2, +3, +4, or +5 position relative to the glutamine residue. In some embodiments, the acceptor glutamine residue is flanked by an N-glycosylation site at −1, −2, −3, −4, or −5 position relative to the glutamine residue.

Thus, in some embodiments, there is provided an Fc-containing polypeptide conjugate comprising an Fc-containing polypeptide site-specifically conjugated to a conjugate moiety, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue.

In some embodiments, there is provided an Fc-containing polypeptide conjugate comprising an Fc-containing polypeptide site-specifically conjugated to a conjugate moiety, wherein the Fc-containing polypeptide comprises an N-glycosylated Fc region, wherein the N-glycosylated Fc region comprises an acceptor glutamine residue that is 5 or less amino acids apart (including for example 4, 3, 2, or 1 amino acids part) from the N-glycosylation site, and wherein the conjugate moiety is conjugated to the Fc-containing polypeptide via the acceptor glutamine residue.

In some embodiments, there is provided an Fc-containing polypeptide conjugate comprising an Fc-containing polypeptide site-specifically conjugated to a conjugate moiety, wherein the Fc-containing polypeptide comprises an N-glycosylated Fc region, wherein the acceptor glutamine residue is flanked by an N-glycosylation site at +2 position relative to the glutamine residue, and wherein the conjugate moiety is conjugated to the Fc-containing polypeptide via the acceptor glutamine residue.

In some embodiments, there is provided an Fc-containing polypeptide conjugate comprising an Fc-containing polypeptide site-specifically conjugated to a conjugate moiety, wherein the Fc-containing polypeptide comprises an N-glycosylated Fc region, wherein the N-glycosylated Fc region comprises amino acid sequence of SEQ ID NO:1

(KPREEQX$_1$NSTX$_2$R, wherein X$_1$ is Y or F and X$_2$ is Y or F), and wherein the conjugate moiety is conjugated to the Fc-containing polypeptide via the acceptor glutamine residue at position 6 of SEQ ID NO:1, and wherein the N-glycosylation is at position 8 of SEQ ID NO:1. In some embodiments, there is provided an Fc-containing polypeptide conjugate comprising an Fc-containing polypeptide specifically conjugated to a conjugate moiety, wherein the Fc-containing polypeptide comprises an N-glycosylated Fc region, wherein the N-glycosylated Fc region comprises amino acid sequence of SEQ ID NO:2 (KPREEQYNSTYR), and wherein the conjugate moiety is conjugated to the Fc-containing polypeptide via the acceptor glutamine residue at position 6 of SEQ ID NO:2, and wherein the N-glycosylation is at position 8 of SEQ ID NO:2.

Figure 1:
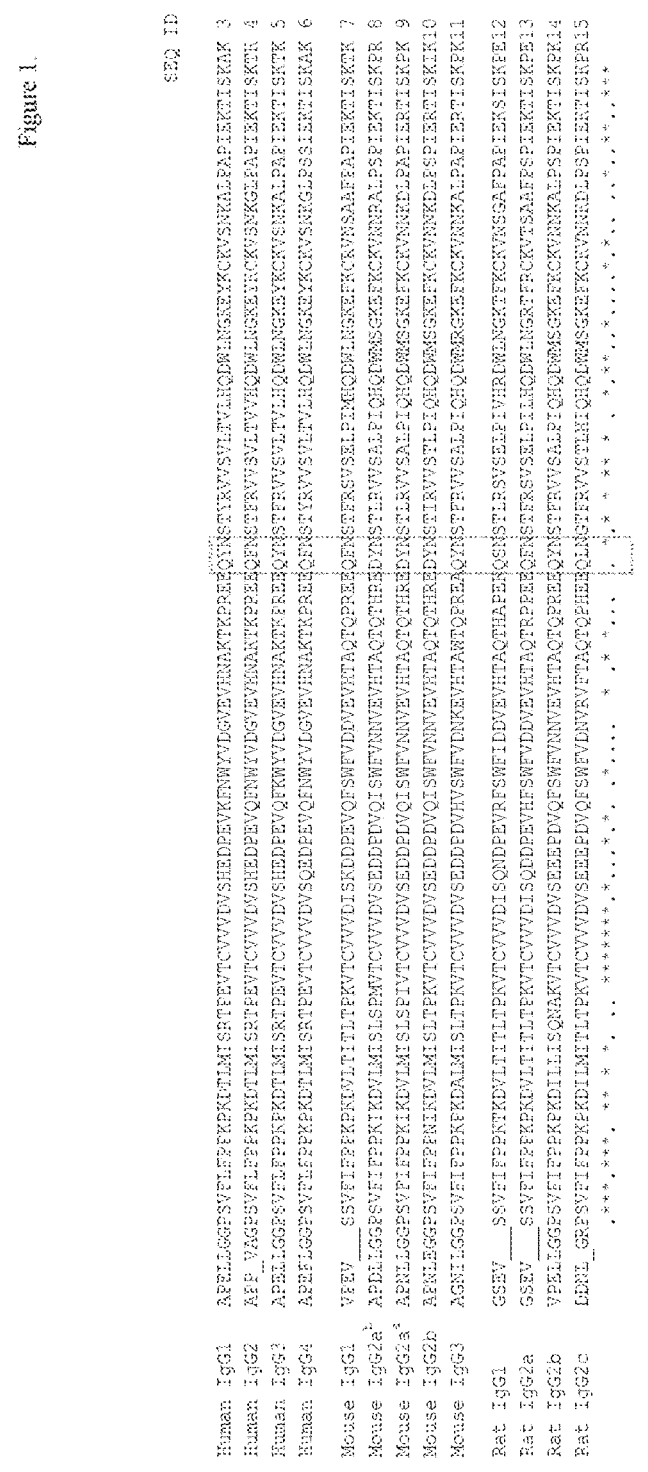

In some embodiments, there is provided an Fc-containing polypeptide conjugate comprising an Fc-containing polypeptide site-specifically conjugated to a conjugate moiety, wherein the Fc-containing polypeptide comprises an N-glycosylated Fc region, wherein the N-glycosylated Fc region comprises amino acid sequence of SEQ ID NO:3 (CH2 sequence of human IgG1, see FIG. 1), and wherein the conjugate moiety is conjugated to the Fc-containing polypeptide via the acceptor glutamine residue at position 65 of SEQ ID NO:3, and wherein the N-glycosylation is at position 67 of SEQ ID NO:3 (see residues in the box shown in FIG. 1).

In some embodiments, there is provided an Fc-containing polypeptide conjugate comprising an Fc-containing polypeptide specifically conjugated to a conjugate moiety, wherein the Fc-containing polypeptide comprises an N-glycosylated Fc region, wherein the N-glycosylated Fc region comprises amino acid sequence of SEQ ID NO:4 (CH2 sequence of human IgG2, see FIG. 1), and wherein the conjugate moiety is conjugated to the Fc-containing polypeptide via the acceptor glutamine residue at position 64 of SEQ ID NO:4, and wherein the N-glycosylation is at position 66 of SEQ ID NO:4 (see residues in the box shown in FIG. 1).

In some embodiments, there is provided an Fc-containing polypeptide conjugate comprising an Fc-containing polypeptide specifically conjugated to a conjugate moiety, wherein the Fc-containing polypeptide comprises an N-glycosylated Fc region, wherein the N-glycosylated Fc region comprises amino acid sequence of SEQ ID NO:5 (CH2 sequence of human IgG3, see FIG. 1), and wherein the conjugate moiety is conjugated to the Fc-containing polypeptide via the acceptor glutamine residue at position 65 of SEQ ID NO:5, and wherein the N-glycosylation is at position 67 of SEQ ID NO:5 (see residues in the box shown in FIG. 1).

In some embodiments, there is provided an Fc-containing polypeptide conjugate comprising an Fc-containing polypeptide specifically conjugated to a conjugate moiety, wherein the Fc-containing polypeptide comprises an N-glycosylated Fc region, wherein the N-glycosylated Fc region comprises amino acid sequence of SEQ ID NO:6 (CH2 sequence of human IgG4, see FIG. 1), and wherein the conjugate moiety is conjugated to the Fc-containing polypeptide via the acceptor glutamine residue at position 65 of SEQ ID NO:6, and wherein the N-glycosylation is at position 67 of SEQ ID NO:6 (see residues in the box shown in FIG. 1).

In some embodiments, there is provided an antibody drug conjugate comprising an antibody specifically conjugated to a conjugate moiety, wherein the antibody comprises an N-glycosylated Fc region, wherein the N-glycosylated Fc region comprises an acceptor glutamine residue flanked by an N-glycosylation site, and wherein the conjugate moiety is conjugated to the antibody via the acceptor glutamine residue. In some embodiments, the antibody is a human antibody. In some embodiments, the antibody is a humanized antibody. In some embodiments, the antibody is a chimeric antibody. In some embodiments, the antibody is a bispecific or multispecific antibody. In some embodiments, the antibody is trastuzumab.

In some embodiments, there is provided a full length antibody conjugated to a conjugate moiety, wherein the full length antibody comprises an N-glycosylated Fc region, and wherein the conjugate moiety is conjugated to the full length antibody via the acceptor glutamine residue at position 295 of a heavy chains of the antibody, wherein the numbering is according to the EU index as in Kabat. In some embodiments, there is provided an antibody conjugated to a conjugate moiety, wherein the antibody comprises an N-glycosylated Fc region, wherein the conjugate moiety is conjugated to the antibody via the acceptor glutamine residue at position 295 of a heavy chains of the antibody, and wherein the N-glycosylation is at position 297 of the heavy chain, wherein the numbering is according to the EU index as in Kabat.

In some embodiments, there is provided an antibody drug conjugate comprising an antibody conjugated to a conjugation moiety via an endogenous acceptor glutamine residue on the antibody, wherein the antibody drug conjugate is glycosylated (for example N-glycosylated) in the Fc region. In some embodiments, the antibody is a human antibody. In some embodiments, the antibody is a humanized antibody. In some embodiments, the antibody is a chimeric antibody. In some embodiments, the antibody is a bispecific or multispecific antibody. In some embodiments, the antibody is trastuzumab.

In some embodiments, there is provided an antibody drug conjugate comprising trastuzumab that is N-glycosylated in the Fc region, wherein the trastuzumab is conjugated to a conjugation moiety via an endogenous acceptor glutamine residue flanked by the N-glycosylation site. In some embodiments, there is provided an antibody drug conjugate comprising trastuzumab that is N-glycosylated at position 297, wherein the trastuzumab is conjugated to a conjugation moiety via an endogenous acceptor glutamine residue at position 295, wherein the numbering is according to the EU index as in Kabat.

In some embodiments, there is provided a composition comprising the Fc-containing fusion polypeptide described herein, wherein at least some (but not necessarily all) of the Fc-containing fusion polypeptides in the composition is glycosylated (for example N-glycosylated) in the Fc region. For example, in some embodiments, there is provided a composition comprising an antibody drug conjugate, wherein the antibody drug conjugate comprises an antibody conjugated to a conjugation moiety via an endogenous acceptor glutamine residue on the antibody, and wherein at least some of (for example at least about any of 50%, 60%, 70%, 80%, 90%, or 95%) the antibody drug conjugates in the composition is glycosylated (for example N-glycosylated) in the Fc region. In some embodiments, the antibody is a human antibody. In some embodiments, the antibody is a humanized antibody. In some embodiments, the antibody is a chimeric antibody. In some embodiments, the antibody is a bispecific or multispecific antibody. In some embodiments, the antibody is trastuzumab.

The conjugation methods described herein allow for the production of Fc-containing polypeptide conjugates (such as antibody drug conjugate) that are conjugated to a conjugate moiety in a specific and stoichiometrically controlled fashion. As used herein, the term "specifically conjugated" refers to the specific conjugation or crosslinking of the conjugate moiety at a specific site of the Fc-containing polypeptide (such as antibody), namely, the acceptor glutamine residue at the Fc region that is flanked by an N-glycosylation site. Site specificity can be confirmed by various techniques, including, but not limited to, peptide mapping and protein sequencing. In some embodiments, the molar ratio of the conjugate moiety to the Fc-containing polypeptide (such as antibody) on the Fc-containing polypeptide conjugate (such as antibody drug conjugate) is about 1:1. In some embodiments, the molar ratio of the conjugate moiety to the Fc-containing polypeptide (such as antibody) on the Fc-containing polypeptide conjugate (such as antibody drug conjugate) is about 2:1. In some embodiments, at least about 80% (such as at least about any of 85%, 90%, 95% or more) of the Fc-containing polypeptide conjugate (such as antibody drug conjugate) in the composition has the Fc-containing polypeptide (such as antibody) to conjugate moiety molar ratio of about 1:1. In some embodiments, at least about 80% (such as at least about any of 85%, 90%, 95% or more) of the Fc-containing polypeptide conjugate (such as antibody drug conjugate) in the composition has the Fc-containing polypeptide (such as antibody) to conjugate moiety molar ratio of about 1:2. In some embodiments, at least about 80% (such as at least about any of 85%, 90%, 95% or more) of the Fc-containing polypeptide conjugate (such as antibody drug conjugate) in the composition has the Fc-containing polypeptide (such as antibody) to conjugate moiety molar ratio of about 1:1 or about 1:2.

The conjugate moiety described herein can be any moiety that can be conjugated to the acceptor glutamine residue, either directly or via a small molecule handle as further described herein. The conjugation between the conjugation moiety and the acceptor glutamine residue is carried out by conjugating the amine donor group of the conjugation moiety or the small molecule handle to the acceptor glutamine residue. Thus, any conjugate moiety containing an amine donor group can be directly conjugated to the Fc-containing polypeptide. Any conjugate moiety not containing an amine donor group can be indirectly conjugated to the Fc-containing polypeptide via a small molecule handle which contains an amine donor group.

The term "amine donor group" as used herein refers to a reactive group containing one or more reactive amines (e.g., primary amines). For example, the conjugate moiety can comprise an amine donor group (e.g., primary amine —NH2), an optional linker, and an active moiety (e.g., a small molecule). The conjugate moiety can also be a polypeptide or a biocompatible polymer containing a reactive Lys (e.g., an endogenous Lys). The amine donor group in some embodiments is a primary amine (—NH2) that provides a substrate for transglutaminase to allow conjugation of the agent moiety to the Fc-containing polypeptide via the acceptor glutamine. Accordingly, the linkage between the donor glutamine and the amine donor group can be of the formula —$CH_2$—$CH_2$—CO—NH—.

In some embodiments, the Fc-containing polypeptide and the conjugate moiety are linked through a linker. In some embodiments, the linker is a non-cleavable linker. Suitable non-cleavable linkers include, but are not limited to, $NH_2$—R—X, $NH_2NH$—R—X, and $NH_2$—O—R—X, wherein R is alkyl or polyethylene glycol group (also referred to as PEG), wherein X is the active moiety. A polyethylene glycol group or PEG group may have a formula of —$(CH_2CH_2O)_n$—, wherein n is an integer of at least 1. In some embodiments, n is any of 2, 4, 6, 8, 10, 12, 16, 20, or 24.

In some embodiments, the Fc-containing polypeptide and the conjugate moiety are linked through a cleavable linker. Suitable cleavable linkers include, but are not limited to, Lys-Phe-X, Lys-Val-Cit-PABC-X, $NH_2$—$(CH_2CH_2O)_n$-Val-Cit-PABC-X, and $NH_2$—$(CH_2CH_2O)_n$-(Val-Cit-PABC-X)$_2$, wherein X is the active moiety, and n is an integer of at least 1 (such as any of 2, 4, 6, 8, 10, 12, 16, 20, or 24). PABC refers to p-aminobenzyloxycarbonyl. Cit refers to citrulline.

Other exemplary amine donor group-linkers include, but are not limited to, Ac-Lys-Gly, aminocaproic acid, Ac-Lys-beta-Ala, amino-PEG2 (Polyethylene Glycol)-C2, amino-PEG3-C2, amino-PEG6-C2, Ac-Lys-Val (valine)-Cit (citrulline)-PABC (p-aminobenzyloxycarbonyl), aminocaproyl-Val-Cit-PABC, putrescine, and Ac-Lys-putrescine.

In some embodiments, the conjugate moiety is linked to the acceptor glutamine residue via a —NH—$(C)_n$— linker, wherein the $(C)_n$ is a substituted or unsubstituted alkyl or heteroalkyl chain, wherein n is an integer from about 1 to about 60. In some embodiments, the carbon of the chain is substituted with an alkoxyl, hydroxyl, alkylcarbonyloxy, alkyl-S—, thiol, alkyl-C(O)S—, amine, alkylamine, amide, or alkylamide. In some embodiments, n is about 2 to about 20.

In some embodiments, the linker is branched. In some embodiments, the linker is linear. In some embodiments, the linker has more than one (such as 2, 3, 4, 5, 6, 7, 8, 9, 10, 11, 12, 13, 14, 15, 16, 17, 18, 19, 20, or more) attachment sites for the attachment of active moieties. These active moieties can be the same or different from each other. For example, the conjugate moiety may comprise a polyacetal or polyacetal derivative-based polymer linked to a plurality of active moieties (such as drug molecules).

In some embodiments, the conjugate moiety is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac(acetyl)-LysGly-MMAD (monomethyl auristatin D), Amino-PEG3 (polyethylene glycol)-C2-MMAD, Amino-PEG6 C2-MMAD, Amino-PEG3-C2-amino-nonanoyl-MMAD, Aminocaproyl-Val(valine)-Cit(citrulline)-PABC(p-aminobenzyloxycarbonyl)-MMAD, Ac-Lys-Val-Cit-PABC-MMAD, Aminocaproyl-MMAD, Ac-Lys-beta-Ala-MMAD, amino-PEG2-C2-MMAE (monomethyl auristatin E), Aminocaproyl-MMAE, amino-PEG3-C2-MMAE, Aminocaproyl-MMAF (monomethyl auristatin F), Aminocaproyl-Val-Cit-PABC-MMAE, Aminocaproyl-Val-Cit-PABC-MMAF, putrescinyl-geldanamycin, and Ac-Lys-putrescinyl-geldanamycin. MMAE refers to monomethyl auristatin E or derivatives thereof.

In some embodiments, the conjugate moiety is a compound comprising a diamine. In some embodiments, the compound is selected from the group consisting of putrescine (butane-1,4-diamine), ethylenediamine, cadaverine (pentane-1,5-diamine), spermidine, spermine, hydrazine, 1,3-diaminopropane, hexamethylenediamine, phenylenediamine, xylylenediamine, diphenylethylenediamine, 1,8-diaminonapthalene, and stereoisomers, isosteres, analogs or derivatives thereof.

Figure 8:
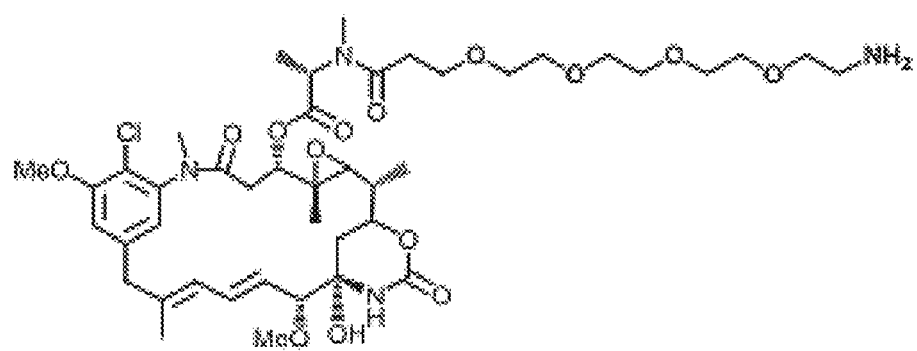
FIG. 8 provides a maytansine derivative containing an extended, non-cleavable linear PEG linker with a primary amine group of molecular weight 896.42 Da, referred herein as MAY-PEG4.
Figure 9:
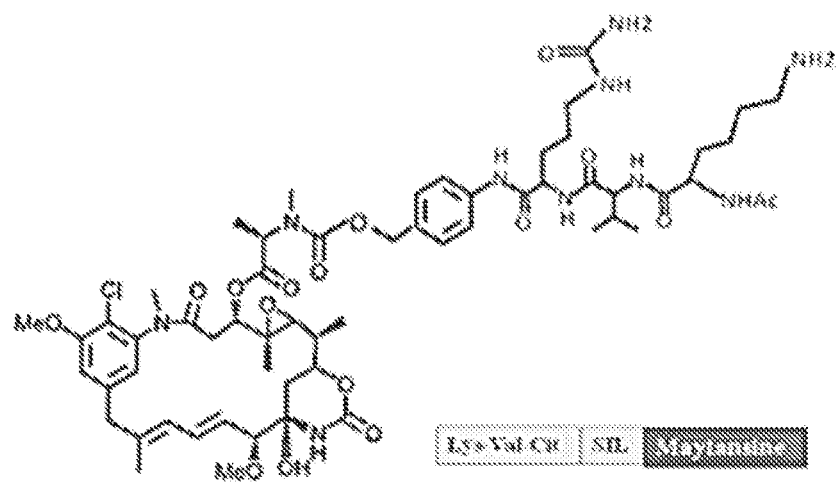
FIG. 9 provides a maytansine derivative containing a cleavable linker with a self-immolative spacer and terminal lysine of molecular weight 1224.58 Da, referred herein as MAY-PVCL.

In some embodiments, the conjugate moiety is a maytansine derivative, such as MAY-PEG4 shown in FIG. 8 or MAY-PVCL shown in FIG. 9.

In some embodiments, the conjugate moiety is an MMAE derivative comprising a non-cleavable linker (such as an amino-$(CH_2CH_2O)_n$— linker, for example, PEGx-MMAE as shown in FIG. 12). In some embodiments, the conjugate moiety is an MMAE derivative comprising a cleavable linker (such as PEG3c-MMAE shown in FIG. 12).

In some embodiments, there is provided an antibody drug conjugate comprising trastuzumab that is N-glycosylated in the Fc region, wherein the trastuzumab is conjugated to a conjugation moiety comprising at least one MMAE (such as 1, 2, or more) through an acceptor glutamine residue flanked by the N-glycosylation site. In some embodiments, the conjugation moiety is PEGx-MMAE as shown in FIG. 12, wherein x is an integer selected from 2, 4, 6, 8, 10, 12, 16, 20, and 24. In some embodiments, the conjugation moiety is PEG3c-MMAE as shown in FIG. 12. In some embodiments, the conjugation moiety comprises two MMAE and a 3-arm PEG linker.

In some embodiments, there is provided a composition comprising any of the antibody drug conjugated described above comprising trastuzumab. In some embodiments, the average molar ratio between the active moiety (such as drug, e.g. MMAE) in the conjugation moiety to the trastuzumab in the composition is about any of 1:1, 2:1, or 4:1. In some embodiments, at least about 80% (such as at least about any of 85%, 90%, 95% or more) of the antibody drug conjugate comprising trastuzumab in the composition has a molar ratio between the active moiety (such as drug, e.g. MMAE) in the conjugation moiety to the trastuzumab of about 2:1. In some embodiments, at least about 80% (such as at least about any of 85%, 90%, 95% or more) of the antibody drug conjugate comprising trastuzumab in the composition has a molar ratio between the active moiety (such as drug, e.g. MMAE) in the conjugation moiety to the trastuzumab of about 4:1.

In some embodiments, the Fc-containing polypeptide conjugate is present in an individual (e.g., a mammal) at about 50% or more after at least about 1 day upon administration in vivo. In some embodiments, the Fc-containing polypeptide conjugate) is present in an individual (e.g., a mammal) at about any of 20%, 25%, 30%, 35%, 40%, 45%, 50%, 55%, 60%, 65%, 70%, 75%, 80%, 85%, 90%, or 95% or more after at least about any of 2 hours, 2-6 hours, 6-12 hours, 12-18 hours, 18-24 hours, 1 day, 2 days, 3 days, 4 days, 5 days, 6 days, 1 week, or 2 weeks upon administration in vivo.

Active Moieties

The conjugate moieties described herein in some embodiments comprise an active moiety. In some embodiments, the conjugate moiety comprises an active moiety that is a peptide or polypeptide. In some embodiments, the conjugate moiety comprises an active moiety that is a biocompatible polymer.

In some embodiments, the conjugate moiety comprises an active moiety that is a cytotoxic agent, an immunosuppressive agent, or an imaging agent (e.g., a fluorophore). In some embodiments, the cytotoxic agent is a chemotherapeutic agent. In some embodiments, the active a moiety is any one of: a moiety that improves the pharmacokinetic property of the Fc-containing polypeptide, a therapeutic moiety, and a diagnostic moiety. In some embodiments, the active moiety is a small molecule.

In some embodiments, the conjugation moiety comprises an active moiety that is a cytotoxic agent. Examples of a cytotoxic agent include, but are not limited to, an anthracycline, an auristatin, a dolastatin, CC-1065, a duocarmycin, an enediyne, a geldanamycin, a maytansine, a puromycin, a taxane, a vinca alkaloid, SN-38, tubulysin, hemiasterlin, and stereoisomers, isosteres, analogs or derivatives thereof. In some embodiments, the conjugation moiety comprises monodansylcadaverine (MDC). In some embodiments, the conjugation moiety comprises TAM1. In some embodiments, the conjugation moiety comprises monomethyl auristatin E (MMAE).

The anthracyclines are derived from bacteria *Streptomyces* and have been used to treat a wide range of cancers, such as leukemias, lymphomas, breast, uterine, ovarian, and lung cancers. Exemplary anthracyclines include, but are not limited to, daunorubicin, doxorubicin (i.e., adriamycin), epirubicin, idarubicin, valrubicin, and mitoxantrone.

Dolastatins and their peptidic analogs and derivatives, auristatins, are highly potent antimitotic agents that have been shown to have anticancer and antifungal activity. See, e.g., U.S. Pat. No. 5,663,149 and Pettit et al., Antimicrob. Agents Chemother. 42:2961-2965 (1998). Exemplary dolastatins and auristatins include, but are not limited to, auristatin E, auristatin EB (AEB), auristatin EFP (AEFP), MMAD, MMAF, MMAE, and 5-benzoylvaleric acid-AE ester (AEVB).

Duocarmycin and CC-1065 are DNA alkylating agents with cytotoxic potency. See Boger and Johnson, PNAS 92:3642-3649 (1995). Exemplary dolastatins and auristatins include, but are not limited to, (+)-docarmycin A and (+)-duocarmycin SA, and (+)-CC-1065.

Enediynes are a class of anti-tumor bacterial products characterized by either nine- and ten-membered rings or the presence of a cyclic system of conjugated triple-double-triple bonds. Exemplary enediynes include, but are not limited to, calicheamicin, esperamicin, and dynemicin.

Geldanamycins are benzoquinone ansamycin antibiotic that bind to Hsp90 (Heat Shock Protein 90) and have been used antitumor drugs. Exemplary geldanamycins include, but are not limited to, 17-AAG (17-N-Allylamino-17-Demethoxygeldanamycin) and 17-DMAG (17-Dimethylaminoethylamino-17-demethoxygeldanamycin).

Maytansines or their derivatives maytansinoids inhibit cell proliferation by inhibiting the microtubules formation during mitosis through inhibition of polymerization of tubulin. See Remillard et al., Science 189:1002-1005 (1975). Exemplary maytansines and maytansinoids include, but are not limited to, mertansine (DM1) and its derivatives as well as ansamitocin.

Taxanes are diterpenes that act as anti-tubulin agents or mitotic inhibitors. Exemplary taxanes include, but are not limited to, paclitaxel (e.g., TAXOL®) and docetaxel (TAXOTERE®).

Vinca alkyloids are also anti-tubulin agents. Exemplary vinca alkyloids include, but are not limited to, vincristine, vinblastine, vindesine, and vinorelbine.

In some embodiments, the conjugate moiety comprises an active moiety that is an immunosuppressive agent. Examples of an immunosuppressive agent include, but are not limited to, gancyclovier, etanercept, tacrolimus, sirolimus, voclosporin, cyclosporine, rapamycin, cyclophosphamide, azathioprine, mycophenolgate mofetil, methotrextrate, and glucocorticoid and its analogs.

In some embodiments, the conjugate moiety comprises an active moiety that is an imaging agent (e.g., a fluorophore), such as fluorescein, rhodamine, lanthanide phosphors, and their derivatives thereof. Examples of fluorophores include, but are not limited to, fluorescein isothiocyanate (FITC) (e.g., 5-FITC), fluorescein amidite (FAM) (e.g., 5-FAM), eosin, carboxyfluorescein, erythrosine, Alexa Fluor® (e.g., Alexa 350, 405, 430, 488, 500, 514, 532, 546, 555, 568, 594, 610, 633, 647, 660, 680, 700, or 750), carboxytetramethylrhodamine (TAMRA) (e.g., 5,-TAMRA), tetramethylrhodamine (TMR), and sulforhodamine (SR) (e.g., SR101).

In some embodiments, the conjugate moiety comprises an active moiety that is a polypeptide. In some embodiments, the polypeptide is an antibody, such as a humanized, human, chimeric, or murine monoclonal antibody.

In some embodiments, the conjugate moiety comprises an active moiety that is a toxin polypeptide (or a toxin protein). Examples of a toxin polypeptide include, but are not limited to, diphtheria A chain, nonbinding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, inhibitor cystine knot (ICK) peptides (e.g., ceratotoxins), and conotoxin (e.g., KIIIA or SmIIIa).

In some embodiments, the conjugate moiety comprises a label such as a radioisotope. Examples of a radioisotope or other labels include, but are not limited to, 3H, 14C, 15N, 35S, 18F, 32P, 33P, 64Cu, 68Ga, 89Zr, 90Y, 99Tc, 123I, 124I, 125I, 131I, 111In, 131In, 153Sm, 186Re, 188Re, 211At, 212Bi, and 153Pb.

In some embodiments, the conjugate moiety comprises an active moiety that is selected from the group consisting of Alexa 488 cadaverine, 5-FITC cadaverine, Alexa 647 cadaverine, Alexa 350 cadaverine, 5-TAMRA cadaverine, 5-FAM cadaverine, SR101 cadaverine, 5,6-TAMRA cadaverine, 5-FAM lysine, Ac-Lys-Gly-MMAD, amino-PEG3-C2-MMAD, amino-PEG6-C2-MMAD, amino-PEG3-C2-amino-nonanoyl-MMAD], aminocaproyl-Val-Cit-PABC-MMAD, Ac-Lys-beta-Ala-MMAD, Aminocaproyl-MMAD, Ac-Lys-Val-Cit-PABC-MMAD, Aminocaproyl-MMAE, amino-PEG3-C2-MMAE, amino-PEG2-C2-MMAE, Aminocaproyl-MMAF, Aminocaproyl-Val-Cit-PABC-MMAE, Aminocaproyl-Val-Cit-PABC-MMAF, amino-PEG2-C2-MMAF, amino-PEG3-C2-MMAF, putrescinyl-geldanamycin, and Ac-Lys-putrescinyl-geldanamycin. In some embodiments, the amine donor agent is aminocaproyl-Val-Cit-PABC-MMAE, aminocaproyl-Val-Cit-PABC-MMAF, Ac-Lys-putrescinyl-geldanamycin, Ac-Lys-beta-Ala-MMAD, Ac-Lys-Val-Cit-PABC-MMAD, aminocaproyl-Val-Cit-PABC-MMAD, and amino-PEG6-C2-MMAD.

In some embodiments, the conjugate moiety comprises an active moiety that is a biocompatible polymer. The Fc-containing polypeptide can be conjugated to the biocompatible polymer to improve the biological characteristics of the Fc-containing polypeptide, e.g., to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

Methods of Making Fc-Containing Polypeptide Conjugates

In another aspect, the present application provides methods of making the Fc-containing polypeptide conjugates (such as antibody drug conjugates) using wildtype or engineered transglutaminase.

The inventor has created engineered TGases that are designed to specifically conjugate a conjugate moiety to an acceptor glutamine residue on the Fc region of an Fc-containing polypeptide (such as antibody) that is flanked by an N-glycosylation site. Contrary to previous belief that a glutamine residue on the Fc region flanked by an N-glycosylation site would be inaccessible to the action of TGase, the inventor has further surprisingly found that, by utilizing a specific reaction condition (for example a specific concentration of the enzyme), wildtype TGases are also able to conjugate a conjugate moiety to an acceptor glutamine residue on the Fc region that is flanked by an N-glycosylation site in a site-specific and stoichiometric manner.

The methods described herein in some embodiments involve a single conjugation step. Such method is particularly suitable, for example, when a conjugation yield of between 20-98% is sufficient to generate a substantial amount of the Fc-containing polypeptide conjugate. The one-step method is also useful when the size of linker needs be minimized, when there is plenty of supply of the Fc-containing polypeptide, when the drug solubility is moderate (for example about 100 mg/L), and when time saving is a bigger concern than getting a high yield.

In some embodiments, the method involves two steps. First, a small molecule handle is conjugated to the Fc-containing polypeptide via a TGase to create an intermediate conjugate. Subsequently, an active moiety is coupled to the intermediate conjugate via the small molecule handle, either covalently or noncovalently. The small molecule handle can be specifically designed to tailor the coupling of the active moiety, thus allows the conjugation of any kind of active moiety to the Fc-containing polypeptide. The two-step method is particularly useful when the supply of the Fc-containing polypeptide and/or active moiety is limited, and when the active moiety (such as toxin) has low water solubility and/or induces aggregation of the polypeptide. By using a small molecule handle, the first enzymatic coupling step can allow the achievement of high yield in conjugation. The second chemoselective coupling step then only requires a reactant ratio of active moiety: Fc-containing polypeptide between 1.2 to 1.5. This may lead to a higher overall conjugation yield than a one-step process.

Thus, in some embodiments, there is provided a method of making an Fc-containing polypeptide conjugate comprising an Fc-containing polypeptide specifically conjugated to a conjugate moiety comprising: contacting the Fc-containing polypeptide with the conjugate moiety in the presence of a transglutaminase under a condition that is sufficient to generate the Fc-containing polypeptide conjugate, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue. In some embodiments, there is provided a method of making an Fc-containing polypeptide conjugate comprising an Fc-containing polypeptide specifically conjugated to a conjugate moiety comprising: contacting a composition comprising Fc-containing polypeptides with the conjugate moiety in the presence of a transglutaminase under a condition that is sufficient to generate the Fc-containing polypeptide conjugate, wherein at least some (e.g., at least about 50%, 60%, 70%, 80%, 90%, or more) the Fc-containing polypeptides comprise an N-glycosylated Fc region, wherein the Fc region comprises an acceptor glutamine residue flanked by an N-glycosylation site, and wherein the conjugate moiety is conjugated to the Fc-containing polypeptide via the acceptor glutamine residue.

In some embodiments, there is provided a method of making an antibody drug conjugate comprising an antibody specifically conjugated to a conjugate moiety comprising: contacting the antibody with the conjugate moiety in the presence of a transglutaminase under a condition that is sufficient to generate the antibody drug conjugate, wherein the antibody is glycosylated (e.g., N-glycosylated) in the Fc-region, and wherein the conjugate moiety is conjugated to the endogenous acceptor glutamine residue on the antibody. In some embodiments, there is provided a method of making an antibody drug conjugate comprising an antibody specifically conjugated to a conjugate moiety comprising: contacting an antibody composition with the conjugate moiety in the presence of a transglutaminase under a condition sufficient to generate the antibody drug conjugate, wherein at least about some (e.g., at least about 50%, 60%, 70%, 80%, 90%, or more) of the antibody in the composition is glycosylated in the Fc-region, and wherein the conjugate moiety is conjugated to the endogenous acceptor glutamine residue on the antibody.

In some embodiments, there is provided a method of making an Fc-containing polypeptide conjugate comprising an Fc-containing polypeptide specifically conjugated to a conjugate moiety comprising a small molecule handle and an active moiety comprising: a) contacting the Fc-containing polypeptide with the small molecule handle in the presence of a transglutaminase under a condition that is sufficient to generate an intermediate conjugate comprising an Fc-containing polypeptide specifically conjugated to the small molecule handle, and b) contacting the intermediate conjugate with an active moiety thereby obtaining the Fc-containing polypeptide conjugate, wherein the Fc-containing polypeptide comprises an N-glycosylated Fc region, wherein the N-glycosylated Fc region comprises an acceptor glutamine residue flanked by an N-glycosylation site, and wherein the conjugate moiety is conjugated to the Fc-containing polypeptide via the acceptor glutamine residue. In some embodiments, there is provided a method of making an Fc-containing polypeptide conjugate comprising an Fc-containing polypeptide specifically conjugated to a conjugate moiety comprising a small molecule handle and an active moiety comprising: a) contacting a composition comprising Fc-containing polypeptides with the small molecule handle in the presence of a transglutaminase under a condition that is sufficient to generate an intermediate conjugate comprising an Fc-containing polypeptide specifically conjugated to the small molecule handle, and b) contacting the intermediate conjugate with an active moiety thereby obtaining the Fc-containing polypeptide conjugate, wherein at least some (e.g., 50%, 60%, 70%, 80%, 90%, or more) the Fc-containing polypeptides comprise an N-glycosylated Fc region, wherein the Fc region comprises an acceptor glutamine residue flanked by an N-glycosylation site, and wherein the conjugate moiety is conjugated to the Fc-containing polypeptide via the acceptor glutamine residue.

In some embodiments, there is provided a method of making an antibody drug conjugate comprising an antibody specifically conjugated to a conjugate moiety comprising a small molecule handle and an active moiety comprising: a) contacting the antibody with the small molecule handle in the presence of a transglutaminase under a condition that is sufficient to generate an intermediate conjugate comprising an antibody specifically conjugated to the small molecule handle, and b) contacting the intermediate conjugate with an active moiety thereby obtaining the antibody drug conjugate, wherein the antibody is glycosylated (e.g., N-glycosylated) in the Fc-region, and wherein the conjugate moiety is conjugated to the endogenous acceptor glutamine residue on the antibody. In some embodiments, there is provided a method of making an antibody drug conjugate comprising antibody specifically conjugated to a conjugate moiety comprising a small molecule handle and an active moiety comprising: a) contacting an antibody composition with the small molecule handle in the presence of a transglutaminase under a condition sufficient to generate an intermediate conjugate comprising an antibody specifically conjugated to the small molecule handle, and b) contacting the intermediate conjugate with an active moiety thereby obtaining the antibody drug conjugate, wherein at least some (e.g., at least about any of 50%, 60%, 70%, 80%, 90%, or more) of the antibody in the composition is glycosylated (e.g., N-glycosylated) in the Fc-region, and wherein the conjugate moiety is conjugated to the endogenous acceptor glutamine residue on the antibody.

The small molecule handle described herein generally has the structure of —$NH_2$—R, wherein R is a moiety that allows the attachment of the activate moiety. The introduction of the small molecule handle in the methods described herein significantly increases the flexibility of the methods. Specifically, the structure of the small molecule handle can be tailored to the attachment of the desired active moiety. For example, in some embodiments, R is a ligand which specifically binds to a binding partner. This allows attachment of any molecule (such as protein) that contains the binding partner. Suitable ligand/binding partner pairs include, but are not limited to, antibody/antigen, antigen/antibody, avidin/biotin, biotin/avidin, streptavidin/biotin, biotin/streptavidin, glutathione/GST, GST/glutathione, maltose binding protein/amylose, amylose/maltose binding protein, cellulose binding protein and cellulose, cellulose/cellulose binding protein, etc.

Other suitable small molecule handles described herein include, but are not limited to, $NH_2$—$CH_2$—CH(OH)—$CH_2$—$NH_2$, $NH_2$—R—$(OR')_2$, $NH_2$—R=O, $NH_2$—R—SH, $NH_2$-R-Azide. These small molecule handles allow the attachment of the conjugate moiety through suitable linkers such as $NH_2$—O—R—X, Maleimide-R—X, and Cyclooctyne-R—$(R'$—$X)_2$, wherein X is the active moiety, and R and R' are independently linker groups, such as linker groups comprising alkyl or polyethylene glycol groups. In some embodiments, the small molecule handle is a 3-arm PEG linker with an amino group and two azide groups (such as the 3-arm PEG linker depicted in FIG. 18, top panel), wherein each of the azide groups may be conjugated to an active moiety.

The TGase-catalyzed reaction can be carried out from several hours to a day (e.g. overnight). The conjugate moiety or the small molecule handle are allowed to react with Fc-containing polypeptide (e.g., 1 mg/mL) at ligand concentrations between 400 and 600 µmol/L, providing a 60 to 90-fold excess of the substrates over the Fc-containing polypeptide, or optionally at lower excess of substrates, e.g. 1- to 20-fold, or 10-20 fold. The reactions can be performed in potassium-free phosphate buffered saline (PBS; pH 8) at 37° C. After 4 h to several days, steady-state conditions are achieved. Excess ligand and enzyme are then removed using centrifugation-dialysis (VIVASPIN® MWCO 50 kDa, Vivascience, Winkel, Switzerland) or diafiltration (PELLICON® MWMCO 50 kDa, Millipore). Reactions may be monitored by HPLC.

The resulting Fc-containing polypeptide conjugates can be analyzed using any suitable method. For example, the stoichiometry of the conjugated polypeptide can be characterized by liquid chromatography mass spectrometry (LC/MS) using a top-down approach in order to assess the number of conjugate moiety or small molecule handle conjugated to antibodies, and in particular the homogeneity of the composition. Conjugates can be reduced before LC/MS analysis and light chains and heavy chains are measured separately.

In one embodiment, the product is analyzed for drug loading (e.g. number of active moiety in the conjugate per Fc-containing polypeptide). Such methods can be used to determine the mean number of conjugates or active moieties (such as drug) per Fc-containing polypeptide as well as the distribution of number of conjugates or active moieties (such as drug) per antibody in a composition, i.e. the percentage of total antibody with any given level of drug loading or DAR. The portion of antibodies having a number (n) of conjugated acceptor glutamines (e.g. n=1, 2, 3, 4, 5, 6, etc.) can be determined. One technique adapted to such determination and more generally drug loading is hydrophobic interaction chromatography (HIC), HIC can be carried out as described for example in Hamblen et al. (2004) Cancer Res. 10: 7063-7070; Wakankar et al. (2011) mAbs 3(2): 161-172; and Lyon et al (2012) Methods in Enzymology, Vol. 502: 123-138, the disclosure of which are incorporated herein by reference.

The molar ratio between the transglutaminase and the Fc-containing polypeptide in the conjugation reaction can be controlled to allow efficient transglutamination reaction. For example, in some embodiments, the molar ratio of the transglutaminase and the Fc-containing polypeptide (such as antibody or antibody composition) is about 10:1 to about 1:100, including any of about 10:1 to about 9:1, about 9:1 to about 8:1, about 8:1 to about 7:1, about 7:1 to about 6:1, about 6:1 to about 5:1, about 5:1 to about 4:1, about 4:1 to about 3:1, about 3:1 to about 2:1, about 2:1 to about 1:1, about 1:1 to about 1:2, about 1:2 to about 1:3, about 1:3 to about 1:4, about 1:4 to about 1:5, about 1:5 to about 1:6, about 1:6 to about 1:7, about 1:7 to about 1:8, about 1:8 to about 1:9, about 1:9 to about 1:10, about 1:10 to about 1:20, about 1:20 to about 1:30, about 1:30 to about 1:40, about 1:40 to about 1:50, about 1:50 to about 1:60, about 1:60 to about 1:70, about 1:70 to about 1:80, about 1:80 to about 1:90, or about 1:90 to about 1:100.

The amount of the transglutaminase in the reaction mixture can be controlled to allow efficient transglutaminase reaction. For example, in some embodiments, the concentration of the tranglutaminase in the reaction mixture is about any of about 0.01 mg/ml to about 5 mg/ml, including for example any of about 0.01 mg/ml to about 0.02 mg/ml, about 0.02 mg/ml to about 0.03 mg/ml, about 0.03 mg/ml to about 0.04 mg/ml, about 0.04 mg/ml to about 0.05 mg/ml, about 0.05 mg/ml to about 0.06 mg/ml, about 0.06 mg/ml to about 0.07 mg/ml, about 0.07 mg/ml to about 0.08 mg/ml, about 0.08 mg·ml to about 0.09 mg/ml, about 0.09 mg/ml to about 0.1 mg/ml, about 0.1 mg/ml to about 0.2 mg/ml, about 0.2 mg/ml to about 0.3 mg/ml, about 0.3 mg/ml to about 0.4 mg/ml, about 0.4 mg/ml to about 0.5 mg/ml, about 0.5 mg/ml to about 0.6 mg/ml, about 0.6 mg/ml to about 0.7 mg/ml, about 0.7 mg/ml to about 0.8 mg/ml, about 0.8 mg/ml to about 0.9 mg/ml, about 0.9 mg/ml to about 1 mg/ml, about 1 mg/ml to about 2 mg/ml, about 2 mg/ml to about 3 mg/ml, about 3 mg/ml to about 4 mg/ml, about 4 mg/ml to about 5 mg/ml. In some embodiments, the concentration of the transglutaminase in the reaction mixture is about 0.05 mg/ml to about 1 mg/ml, such as about 0.2 mg/ml to about 1 mg/ml.

In some embodiments, the transglutaminase reaction is carried out on a solid support. For example, the Fc-containing polypeptide (such as antibody) may be attached to a solid support. The remaining components of the conjugation reaction are then brought into contact with the Fc-containing polypeptide on the solid support and subsequently removed. Alternatively, the transglutaminase may be attached to a solid support. The remaining components of the conjugation reaction are then brought into contact with the transglutaminase on the solid support and subsequently separated from the transglutaminase on the solid support.

Solid support that are useful for the methods described herein include, for example, plates, tubes, bottles, flasks, magnetic beads, magnetic sheets, porous matrices, or any solid surfaces and the like. Agents or molecules that may be used to link the TGase or Fc-containing polypeptide to the solid support include, but are not limited to, lectins, avidin/biotin, inorganic or organic linking molecules. The physical separation can be effected, for example, by filtration, isolation, magnetic field, centrifugation, washing, etc.

In some embodiments, the solid support is a bead, a membrane, a cartridge, a filter, a microtiter plate, a test tube, solid powder, a cast or extrusion molded module, a mesh, a fiber, a magnetic particle composite, or any other solid materials. The solid support may be coated with a substance such as polyethylene, polypropylene, poly(4-methulbutene), polystyrene, polyacrylate, polyethylene terephthalate, rayon, nylon, poly(vinyl butyrate), polyvinylidene difluoride (PCDF), silicones, polyformaldehyde, cellulose, cellulose acetate, nitrocellulose, and the like. In some embodiments, the solid support may be coated with a ligand or impregnated with the ligand.

In some embodiments, the supporting material is a magnetic bead. In some embodiments, the magnetic beads have an average size of about 1-200 microns, such as any of about 1-2 microns, 2-10 microns, 10-30 microns, 30-50 microns, 50-100 microns, and 10-200 microns. In some embodiments, the magnetic beads are monodisperse. In some embodiments, the magnetic beads are coated, for example with protein A.

Other solid support that can be used in the methods described herein include, but are not limited to, gelatin, glass, sepharose macrobeads, dextran microcarriers such as CYTODES® (Pharmacia, Uppsala, Sweden). Also contemplated are polysaccharide such as agrose, alginate, carrageenan, chitin, cellulose, dextran or starch, polyacrylamide, polystyrene, polyacrolein, polyvinyl alcohol, polymethylacrylate, perfluorocarbon, inorganic compounds such as silica, glass, kieselquhr, alumina, iron oxide or other metal oxides, or copolymers consisting of any combination of two or more naturally occurring polymers, synthetic polymers or inorganic compounds.

The amount of the transglutaminase in the reaction mixture (i.e., amount per ml of resin when resin is used as solid support) can be controlled to allow efficient transglutaminase reaction. For example, in some embodiments, the concentration of the tranglutaminase in the reaction mixture (amount per ml of resin) is about any of about 0.01 mg/ml to about 1 mg/ml, including for example any of about 0.01 mg/ml to about 0.02 mg/ml, about 0.02 mg/ml to about 0.03 mg/ml, about 0.03 mg/ml to about 0.04 mg/ml, about 0.04 mg/ml to about 0.05 mg/ml, about 0.05 mg/ml to about 0.06 mg/ml, about 0.06 mg/ml to about 0.07 mg/ml, about 0.07 mg/ml to about 0.08 mg/ml, about 0.08 mg·ml to about 0.09 mg/ml, about 0.09 mg/ml to about 0.1 mg/ml, about 0.1 mg/ml to about 0.2 mg/ml, about 0.2 mg/ml to about 0.3 mg/ml, about 0.3 mg/ml to about 0.4 mg/ml, about 0.4 mg/ml to about 0.5 mg/ml, about 0.5 mg/ml to about 0.6 mg/ml, about 0.6 mg/ml to about 0.7 mg/ml, about 0.7 mg/ml to about 0.8 mg/ml, about 0.8 mg/ml to about 0.9 mg/ml, about 0.9 mg/ml to about 1 mg/ml.

In some embodiments, the concentration ratio between the conjugate moiety and the Fc-containing polypeptide (such as antibody) is from about 2:1 to about 800:1, including but not limited to about any of: 2:1, 3:1, 4:1, 5:1, 6:1, 7:1, 8:1, 9:1, 10:1, 15:1, 20:1, 25:1, 30:1, 35:1, 40:1, 45:1, 50:1, 60:1, 70:1, 80:1, 90:1, 100:1, 200:1, 300:1, 400:1, 500:1, 600:1, 700:1, and 800:1.

In some embodiments, the conjugation efficiency of the Fc-containing polypeptide (such as antibody) and the conjugation moiety is at least about 30%. As used herein, the term "conjugation efficiency" or "crosslinking efficiency" is the ratio between the experimentally measured amount of engineered polypeptide conjugate divided by the maximum expected engineered polypeptide conjugate amount. Conjugation efficiency or crosslinking efficiency can be measured by various techniques well known to persons skilled in the art, such as hydrophobic interaction chromatography. Conjugation efficiency can also be measured at different temperature, such as room temperature or 37° C. In some embodiments, the conjugation efficiency of the Fc-containing polypeptide and the conjugation moiety is at least about any of 30%-35%, 35%-40%, 45%-50%, 50%-55%, 56%-60%, 61%-65%, 66%-70%, 71%-75%, 76%-80%, 81%-85%, 86%-90%, 91%-95%, or 96%-99%. In some embodiments, the conjugation efficiency of the Fc-containing polypeptide and the conjugation moiety is at least about any of 32%, 34%, 36%, 38%, 40%, 42%, 44%, 46%, 48%, 50%, 55%, 60%, 65%, 70%, 75%, 80%, 85%, 90%, 95%, or 99%.

TGases

TGases catalyze covalent protein crosslinking by forming proteinase resistant isopeptide bonds between a lysine donor residue of one protein and an acceptor glutamine residue of another protein, and is accompanied by the release of ammonia. The catalytic mechanism of transglutaminases has been proposed as follows. After the glutamine-containing first substrate (acceptor or Q-substrate) binds to the enzyme, it forms a gamma-glutamylthioester with the cysteine residue in the active center of TGase, known as the acylenzyme intermediate, accompanied by the release of ammonia. The second substrate (donor or K-substrate) then binds to the acylenzyme intermediate and attacks the thioester bond. The product (two proteins crosslinked by an Nepsilon (gamma-glutamyl)lysine isopeptide bridge) is formed and released. This re-establishes the active-center Cys residue of the enzyme in its original form and allows it to participate in another cycle of catalysis. The formation of the covalent acylenzyme intermediate is thought to be the rate-limiting step in these reactions. The catalytic triad of many transglutaminases is papain-like, containing Cys-His-Asp (where His is histidine and Asp is aspartic acid) and, crucially, a tryptophan (Trp) residue located 36 residues away from the active-center Cys. In contrast, bacterial TGases isolated from Streptoverticillium sp (vide supra) has an atypical catalytic triad and shows no sequence homology with the papain-like catalytic triad of other TGases.

Several types of transglutaminases have been reported in various living organisms including microbials. Examples are TGase from guinea pig liver (GTGase), fish liver (FTGase) and microorganisms (mTGase) and any recombinant TGase (rTGase). Other TGases than the ones listed here can also be used according to the invention. Examples of useful TGases include microbial transglutaminases, such as e.g. from *Streptomyces mobaraense, Streptomyces cinnamoneum* and *Streptomyces griseocarneum* disclosed in U.S. Pat. No. 5,156,956, and *Streptomyces lavendulae* disclosed in U.S. Pat. No. 5,252,469, and *Streptomyces ladakanum* disclosed in JP2003199569. Other useful microbial transglutaminases have been isolated from *Bacillus subtilis* (disclosed in U.S. Pat. No. 5,731,183) and from various Myxomycetes. Other examples of useful microbial transglutaminases are those disclosed in WO 96/06931 (e.g. transglutaminase from *Bacilus lydicus*) and WO 96/22366. Useful non-microbial transglutaminases include guinea-pig liver transglutaminase, and transglutaminases from various marine sources like the flat fish Pagrus major (disclosed in EP-0555649), and the Japanese oyster *Crassostrea gigas* (disclosed in U.S. Pat. No. 5,736,356). An exemplary TGase is bacterial transglutaminase (BTG) (see, e.g. EC 2.3.2.13, protein-glutamine-gamma-glutamyltransferase). In another exemplary embodiment, the TGase is from *S. mobaraense*. In another embodiment, the TGase is a mutant (e.g., engineered) TGase having at least 80% sequence homology with native TGase. An example is recombinant bacterial transglutaminase derived from *Streptomyces mobaraensis* (available from Zedira, Darmstadt, Germany).

*Streptomyces ladakanum* ATCC 27441 or NRRL3191 mTgase is expressed as Pre-Pro-mTgase (GenBank access number AY241675). There are 410 amino acid residues in pre-pro-mTGase, 331 in mature enzyme plus 30 of pre and 49 of pro. Pro peptide is a strong inhibitor of mature enzyme. Primers designed according to AY241675 were used to clone the pro-mTgase and mature mTgase from ATCC 27441DNA into pET29b(+) vector's Nde I and Xho I sites. Active mTgase can be obtained either from enterokinase light chain (EKL) digestion of Pro-mTgase or refolding of mature mTgase. mTgase from Strep Ladakanum (TG_SL) is very similar to mTgase from *Strep. mobaraensis* (TG_SM, sold by Ajinomoto as ACTIVA®) with a few amino acid differences (alignment shown in FIG. 2).

The transglutaminase used in methods described herein can be obtained or made from a variety of sources. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and allow enzyme activity. In some embodiments, the transglutaminase is a microbial transglutaminase derived from a microbial genome, such as transglutaminase from *Streptoverticillium* or Streptomices (e.g., *Streptomyces mobaraensis* or *Streptoverticillium mobarensis*). In some embodiments, the transglutaminase is a mammalian protein (e.g., human transglutaminase), a bacterial protein, a plant protein, a fungi protein (e.g., Oomycetes and Actinomicetes transglutaminases), or a prokaryotic protein. In some embodiments, the transglutaminase is from *Micrococcus, Clostridium, Turolpsis, Rhizopus, Monascus,* or *Bacillus*.

Suitable TGase include, but is not limited to, bacterial transglutaminase (BTG) such as the enzyme having EC reference EC 2.3.2.13 (protein-glutamin-γ-glutamyltransferase). In some embodiments, the TGase is from *Strep Ladakanum* (TG_SL, SEQ ID NO:16, see FIG. 2). In some embodiments, the TGase is from *Strep Mobaraensis* (TG-SM, SEQ ID NO:18, see FIG. 2). In some embodiments, the TGase is a recombinant TGase based on the TGase from *Strep Ladakanum* (TG_SL, SEQ ID NO:17, see FIG. 3).

In some embodiments, the transglutaminase used in the methods described herein is a recombinant protein produced using recombinant techniques.

In some embodiments, the transglutaminase is wildtype, for example the TGase having the sequence of SEQ ID NO:16. In some embodiments, the transglutaminase is a recombinant wildtype TGase comprising the wildtype TGase having the sequence of SEQ ID NO:16, wherein the recombinant wildtype TGase further comprises an additional proline at the N-terminus and optionally a purification tag (such as a polyhistidine tag). In some embodiments, the transglutaminase is a recombinant wildtype TGase having a sequence of SEQ ID NO:17 as shown in FIG. 3. Contrary to the general understanding in the art that wildtype transglutaminase is unable to catalyze transglutamination reaction to an acceptor glutamine flanked by an N-glycosylation site, it was surprisingly found that such reaction can be carried out with substantial efficacy and specificity under certain conditions as described here.

In some embodiments, the transglutaminase is engineered. In some embodiments, the transglutaminase is an engineered transglutaminase specifically designed to carry out transglutamination reactions to an acceptor glutamine proximal to an N-glycosylation site. Such engineered tranglutaminases are further described below in detail.

In some embodiments, the transglutaminase is a purified protein. For example, in some embodiments, the transglutaminase is least about 50% pure. As used herein, "pure" or "purified" protein refers to a protein (e.g., transglutaminase) free from other protein contaminants. In some embodiments, the purified transglutaminase is at least about any of 55%-60%, 60%-65%, 65%-70%, 70%-75%, 75%-80%, 80%-85%, 85%-90%, 90%-95%, 95%-98%, or 99% pure. In some embodiments, the purified transglutaminase is at least about any of 50%, 55%, 60%, 65%, 70%, 75%, 80%, 85%, 90%, 95%, 96%, 97%, 98%, 99%, or 100% pure.

Engineered Transglutaminase

The present application in another aspect provides engineered transglutaminase specifically designed to carry out transglutamination reactions to an acceptor glutamine proximal to an N-glycosylation site. We remodeled the substrate binding pocket of TGase to increase the accessibility of the glutamine residue on Fc region (Q295 specifically) to TGase's catalytic residue Cys64 (FIG. 3), and obtained engineered TGases that specifically carry out transglutamination reactions at Q295.

In some embodiments, the engineered TGase is based on the wildtype TGase from *Strep ladalanum* (SEQ ID NO:16 or SEQ ID NO:17). In some embodiments, the engineered TGase is based on the wildtype TGase from *Strep Mobaraensis* (SEQ ID NO:18). The sequence of a TGase isolated from *Strep ladakanum* has an amino acid sequence which is identical to the sequence from *Strep mobaraensis* except for a total of 22 amino acid differences between the two sequences (Yi-Sin Lin et al., Process Biochemistry 39(5), 591-598 (2004).

In some embodiments, the engineered transglutaminase specifically carries out the transglutamination reaction at the acceptor glutamine site at the N-glycosylated Fc region. The term "specifically" used in this context describes a preference of the TGase for reacting with one or more specific glutamine residues at the N-glycosylated Fc region as compared to other specific glutamine residues on the Fc-containing polypeptide (such as antibody).

Thus, for example, in some embodiments, there is provided an engineered transglutaminase capable of conjugating an Fc-containing polypeptide (such as antibody) to a conjugate moiety, wherein the Fc-containing polypeptide (such as antibody) comprises an N-glycosylated Fc region, wherein the N-glycosylated Fc region comprises an acceptor glutamine residue flanked by an N-glycosylation site, wherein upon reaction the conjugate moiety is conjugated to the Fc-containing polypeptide (such as antibody) via the acceptor glutamine residue, and wherein the conjugation is at least about 10% more active than a wildtype transglutaminase under the same reaction conditions. In some embodiments, the engineered TGase has at least about 80% identity to SEQ ID NO:16 and further comprises at least one mutation (such as substitution, deletion, or insertion).

In some embodiments, there is provided an engineered transglutaminase comprising an amino acid sequence having at least about 80% (including for example at least about any of 85%, 90%, 95%, or 95%) identity to SEQ ID NO:16, wherein the transglutaminase comprises a deletion selected from the group consisting of: D1-E4; P244-P247; and H279-H289. In some embodiments, there is provided an engineered transglutaminase comprising an amino acid sequence that is 100% identical to SEQ ID NO:16 except for one or more deletions selected from the group consisting of: D1-E4; P244-P247; and H279-H289.

In some embodiments, there is provided an engineered transglutaminase comprising an amino acid sequence having at least about 80% (including for example at least about any of 85%, 90%, 95%, or 95%) identity to SEQ ID NO:17, wherein the transglutaminase comprises a deletion selected from the group consisting of: P1-E5; P245-P248; and H280-H290. In some embodiments, there is provided an engineered transglutaminase comprising an amino acid sequence that is 100% identical to SEQ ID NO:17 except for one or more deletions selected from the group consisting of: P1-E5; P245-P248; and H280-H290.

In some embodiments, there is provided an engineered transglutaminase comprising an amino acid sequence having at least about 80% (including for example at least about any of 85%, 90%, 95%, or 95%) identity to SEQ ID NO:16, wherein the transglutaminase comprises a mutation selected from the group consisting of: deletion of D1-E4; deletion of P244-P247; deletion of N282-L285; substitution of H279-A287 with a G; and substitution of A280-H289 with a G. In some embodiments, there is provided an engineered transglutaminase comprising an amino acid sequence that is 100% identical to SEQ ID NO:16 except for one or more deletions selected from the group consisting of: a mutation selected from the group consisting of: deletion of D1-E4; deletion of P244-P247; deletion of N282-L285; substitution of H279-A287 with a G; and substitution of A280-H289 with a G.

In some embodiments, there is provided an engineered transglutaminase comprising an amino acid sequence having at least about 80% (including for example at least about any of 85%, 90%, 95%, or 95%) identity to SEQ ID NO:17, wherein the transglutaminase comprises a mutation selected from the group consisting of: deletion of P1-E5; deletion of P245-P248; deletion of N283-L286; substitution of H280-A288 with a G; and substitution of A281-H290 with a G. In some embodiments, there is provided an engineered transglutaminase comprising an amino acid sequence that is 100% identical to SEQ ID NO:17 except for one or more deletions selected from the group consisting of: a mutation selected from the group consisting of: deletion of P1-E5; deletion of P245-P248; deletion of N283-L286; substitution of H280-A288 with a G; and substitution of A281-H290 with a G.

In some embodiments, there is provided an engineered transglutaminase comprising an amino acid sequence that is 100% identical to SEQ ID NO:16 except for a deletion of D1-E4. In some embodiments, there is provided an engineered transglutaminase comprising an amino acid sequence that is 100% identical to SEQ ID NO:16 except for a deletion of P244-P247. In some embodiments, there is provided an engineered transglutaminase comprising an amino acid sequence that is 100% identical to SEQ ID NO:16 except for a deletion of H279-H289. In some embodiments, there is provided an engineered transglutaminase comprising an amino acid sequence that is 100% identical to SEQ ID NO:16 except for a deletion of N282-L285. In some embodiments, there is provided an engineered transglutaminase comprising an amino acid sequence that is 100% identical to SEQ ID NO:16 except for a deletion of D1-E4 and a deletion of N282-L285. In some embodiments, there is provided an engineered transglutaminase comprising an amino acid sequence that is 100% identical to SEQ ID NO:16 except for a deletion of D1-E4, a deletion of P244-P247, and a deletion of N282-L285. In some embodiments, there is provided an engineered transglutaminase comprising an amino acid sequence that is 100% identical to SEQ ID NO:16 except for a deletion of D1-E4 and a substitution of H280-A288 with a G. In some embodiments, there is provided an engineered transglutaminase comprising an amino acid sequence that is 100% identical to SEQ ID NO:16 except for a deletion of D1-E4 and a substitution of A280-H289 with a G.

In some embodiments, there is provided an engineered transglutaminase comprising an amino acid sequence that is 100% identical to SEQ ID NO:17 except for a deletion of P1-E5. In some embodiments, there is provided an engineered transglutaminase comprising an amino acid sequence that is 100% identical to SEQ ID NO:17 except for a deletion of P245-P248. In some embodiments, there is provided an engineered transglutaminase comprising an amino acid sequence that is 100% identical to SEQ ID NO:17 except for a deletion of H280-H290. In some embodiments, there is provided an engineered transglutaminase comprising an amino acid sequence that is 100% identical to SEQ ID NO:17 except for a deletion of N283-N286. In some embodiments, there is provided an engineered transglutaminase comprising an amino acid sequence that is 100% identical to SEQ ID NO:17 except for a deletion of P1-E5 and a deletion of N283-N286. In some embodiments, there is provided an engineered transglutaminase comprising an amino acid sequence that is 100% identical to SEQ ID NO:17 except for a deletion of P1-E5, a deletion of P245-P248, and a deletion of N283-N286. In some embodiments, there is provided an engineered transglutaminase comprising an amino acid sequence that is 100% identical to SEQ ID NO:17 except for a deletion of P1-E5 and a substitution of H280-A288 with a G. In some embodiments, there is provided an engineered transglutaminase comprising an amino acid sequence that is 100% identical to SEQ ID NO:17 except for a deletion of P1-E5 and a substitution of A281-H290 with a G.

The terms "sequence identity" or "identify" as used interchangeably herein refers the degree of sequence relatedness between peptides, as determined by the number of matches between strings of two or more amino acid residues. Sequence identity can be measured, for example, by the percent of identical matches between the smaller of two or more sequences with gap alignments (if any) addressed by a particular mathematical model or computer program (i.e., "algorithms"). Some methods to determine identity are designed to give the largest match between the sequences tested. Methods to determine identity are described in publicly available computer programs. Exemplary computer program methods to determine identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In some embodiments, the engineered transglutaminase has a higher transglutaminase activity than that of the TGase encoded by SEQ ID NO:16 or SEQ ID NO:18. In some embodiments, the specificity activity of the engineered transglutaminase is at least about 1.25×, 1.5×, 2.0×, 2.5×, 3.0×, 3.5×, 4.0×, 4.5×, 5.0×, 5.5×, 6.0×, 6.5×, 7.0×, 7.5×, 8.0×, 8.5×, 9.0×, 9.5×, or 10.5× higher than that of the wildtype TGase (such as the TGase encoded by SEQ ID NO:16 or SEQ ID NO:17).

The engineered TGases described herein can be analyzed for TGase activity by using assays known in the art. For example, U.S. Pat. No. 5,156,956 describes the measurement of the activity of a given peptide is carried out by performing a reaction using benzyloxycarbonyl-L-glutaminyl glycine and hydroxylamine as substrates in the absence of $Ca^{2+}$, forming an iron complex with the resulting hydroxamic acid in the presence of trichloroacetic acid, measuring absorption at 525 nm and determining the amount of hydroxamic acid by a calibration curve to calculate the activity. For the purpose of this specification, a peptide, which exhibits transglutaminase activity in said assay, is deemed to have transglutaminase activity. In particular, the peptides of the present invention exhibit an activity which is more than 30%, such as more than 50%, such as more than 70%, such as more than 90% of that of a TGase from *S. ladakanum* having an amino acid sequence of SEQ ID No. 16.

Also provided herein are nucleic acids (such as isolated nucleic acids) encoding any one of the engineered TGases described herein. As used herein the term "nucleic acid" is intended to indicate any nucleic acid molecule of cDNA, genomic DNA, synthetic DNA or RNA origin. The nucleic acid may be single- or double-stranded, and which may be based on a complete or partial naturally occurring nucleotide sequence encoding a protein of interest. The nucleic acid may optionally contain other nucleic acid segments.

Also provided herein are recombinant vectors (such as amplification vectors and/or expression vectors) comprising nucleic acids encoding the engineered TGases described herein. In some embodiments, there is provided a host cell comprising the recombinant vector.

The recombinant vector comprising the nucleic acid encoding the engineered TGase may be any vector which may conveniently be subjected to recombinant DNA procedures, and the choice of vector may depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The vector is in some embodiments an expression vector in which the DNA sequence encoding the engineered TGase is operably linked to additional segments required for transcription of the DNA. The term, "operably linked" indicates that the segments are arranged so that they function in concert for their intended purposes, e.g. transcription initiates in a promoter and proceeds through the DNA sequence coding for the protein. The promoter may be any DNA sequence which shows transcriptional activity in the host cell of choice and may be derived from genes encoding proteins either homologous or heterologous to the host cell. The DNA sequence encoding the engineered TGase may also, if necessary, be operably connected to a suitable terminator.

In some embodiments, the recombinant vector further comprises DNA sequence(s) enabling the vector to replicate in the host cell in question, and/or a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 125-130 (1985)), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

The host cell into which the vector comprising a nucleic acid encoding the engineered TGase is introduced may be any cell which is capable of producing the engineered TGase and includes bacteria, yeast, fungi and higher eukaryotic cells. The transformed or transfected host cell described above is then cultured in a suitable nutrient medium under conditions permitting the expression of the present peptide, after which the resulting protein is recovered from the culture. In some embodiments, the host cell is a prokaryotic cell. In some embodiments, the host cell is *S. ladakanum*. In some embodiments, the host cell is *S. mobaraensis*. In some embodiments, the host cell is *E. coli*.

Further provided herein are methods of preparing the engineered TGases described herein. The engineered TGases described herein may be prepared in different ways. For example, in some embodiments, the engineered TGase is prepared by culturing a host cell comprising a vector comprising a nucleic acid encoding the engineered TGase and isolating the engineered TGase from the cells.

To direct a protein of the present invention into the secretory pathway of the host cells, a secretory signal sequence (also known as a leader sequence, prepro sequence or pre sequence) may be provided in the recombinant vector. The secretory signal sequence is joined to the DNA sequence encoding the protein in the correct reading frame. Secretory signal sequences are commonly positioned 5' to the DNA sequence encoding the protein. The secretory signal sequence may be that normally associated with the protein or may be from a gene encoding another secreted protein. Alternatively, the protein may be expressed in the inclusion body, and subsequently obtained through denaturation/renaturation.

The medium used to culture the cells may be any conventional medium suitable for growing the host cells, such as minimal or complex media containing appropriate supplements. The protein produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gel filtration chromatography, affinity chromatography, or the like, dependent on the type of protein in question.

In some embodiments, there are provided methods of purifying TGase, such as any one of the TGase described herein. In some embodiments, the method comprises (a) providing a host cell that expresses TGase; (b) culturing said host cell (such as a prokaryotic cell) wherein TGase is expressed as an inclusion body; (c) disrupting said host cell to produce a cell lysate having a soluble fraction and an insoluble fraction; and (d) separating said soluble fraction from said insoluble fraction, wherein said insoluble fraction comprises the TGase. In some embodiments, the method further comprises contacting the insoluble fraction comprising TGase in a denaturing agent (such as urea). In some embodiments, the method further comprises containing the denaturing TGase to a renaturation buffer (such as a buffer comprising DTT). In some embodiments, the method further comprises purifying the TGase by chromatography (such as by affinity chromatography or ion exchange chromatography). In some embodiments, the TGase is tagged (such as his-tagged) to facilitate purification.

In some embodiments, there is provided a method of purifying TGase, comprising (a) culturing a host cell (such as a prokaryotic cell) comprising a vector comprising a nucleic acid encoding a pro-enzyme of TGase, and (b) obtaining mature TGase by cleavage of the pro-sequence of the pro-enzyme (for example by endokinase light chain).

The mutant TGases described herein can be used for making Fc-containing polypeptide conjugates (such as antibody drug conjugates). For example, in some embodiments, there is provided a method of making an antibody drug conjugate comprising an antibody specifically conjugated to a conjugate moiety, comprising: contacting the antibody with the conjugate moiety in the presence of a mutant transglutaminase (such as any of the mutant transglutaminase described herein) under a condition that is sufficient to generate the antibody drug conjugate, wherein the conjugate moiety is conjugated to an acceptor glutamine residue on the antibody. In some embodiments, there is provided a method of making an antibody drug conjugate comprising an antibody specifically conjugated to a conjugate moiety comprising: contacting the antibody with the conjugate moiety in the presence of a mutant transglutaminase (such as any of the mutant transglutaminase described herein) under a condition that is sufficient to generate the antibody drug conjugate, wherein the antibody is glycosylated (e.g., N-glycosylated) in the Fc-region, and wherein the conjugate moiety is conjugated to the endogenous acceptor glutamine residue on the antibody. In some embodiments, there is provided a method of making an antibody drug conjugate comprising an antibody specifically conjugated to a conjugate moiety comprising: contacting a composition comprising the antibody with the conjugate moiety in the presence of a mutant transglutaminase (such as any of the mutant transglutaminase described herein) under a condition that is sufficient to generate the Fc-containing polypeptide conjugate, wherein at least some (e.g., 50%, 60%, 70%, 80%, 90%, or more) the antibody in the composition is glycosylated (e.g., N-glycosylated) in the Fc-region, and wherein the conjugate moiety is conjugated to the endogenous acceptor glutamine residue on the antibody.

In some embodiments, there is provided a method of making an antibody drug conjugate comprising an antibody specifically conjugated to a conjugate moiety comprising a small molecule handle and an active moiety comprising: a) contacting the antibody with the small molecule handle in the presence of a transglutaminase (such as any of the mutant transglutaminase described herein) under a condition that is sufficient to generate an intermediate conjugate comprising an antibody specifically conjugated to the small molecule handle, and b) contacting the intermediate conjugate with an active moiety thereby obtaining the antibody drug conjugate, wherein the conjugate moiety is conjugated to an acceptor glutamine residue on the antibody. In some embodiments, there is provided a method of making an antibody drug conjugate comprising an antibody specifically conjugated to a conjugate moiety comprising a small molecule handle and an active moiety comprising: a) contacting the antibody with the small molecule handle in the presence of a transglutaminase (such as any of the mutant transglutaminase described herein) under a condition that is sufficient to generate an intermediate conjugate comprising an antibody specifically conjugated to the small molecule handle, and b) contacting the intermediate conjugate with an active moiety thereby obtaining the antibody drug conjugate, wherein the antibody is glycosylated (e.g., N-glycosylated) in the Fc-region, and wherein the conjugate moiety is conjugated to the endogenous acceptor glutamine residue on the antibody. In some embodiments, there is provided a method of making an antibody drug conjugate comprising antibody specifically conjugated to a conjugate moiety comprising a small molecule handle and an active moiety comprising: a) contacting a composition comprising antibody with the small molecule handle in the presence of a transglutaminase (such as any of the mutant transglutaminase described herein) under a condition that is sufficient to generate an intermediate conjugate comprising an antibody specifically conjugated to the small molecule handle, and b) contacting the intermediate conjugate with an active moiety thereby obtaining the antibody drug conjugate, wherein at least some (e.g., 50%, 60%, 70%, 80%, 90%, or more) the antibody in the composition is glycosylated (e.g., N-glycosylated) in the Fc-region, and wherein the conjugate moiety is conjugated to the endogenous acceptor glutamine residue on the antibody.

Pharmaceutical Compositions, Unit Doses, and Kits

Also provided are pharmaceutical compositions comprising the Fc-containing polypeptide conjugates (such as antibody drug conjugates) described herein. In some embodiments, the pharmaceutical composition further comprises a pharmaceutically acceptable carrier. In some embodiments, at least about 50% (such as at least about any of 60%, 70%, 80%, 90%, 95%, or 99%) of the Fc-containing polypeptide conjugates (such as antibody drug conjugates) in the pharmaceutical composition has one conjugate moiety attached to the Fc-containing polypeptide (such as antibody). In some embodiments, at least about 50% (such as at least about any of 60%, 70%, 80%, 90%, 95%, or 99%) of the Fc-containing polypeptide conjugates (such as antibody drug conjugates) in the pharmaceutical composition has two conjugate moieties attached to the Fc-containing polypeptide (such as antibody). In some embodiments, at least about 50% (such as at least about any of 60%, 70%, 80%, 90%, 95%, or 99%) of the Fc-containing polypeptide conjugates (such as antibody drug conjugate) in the pharmaceutical composition has either one or two conjugate moieties attached to the Fc-containing polypeptide (such as antibody).

The term "pharmaceutically acceptable carrier" is used herein to describe any ingredient other than the compound(s) of the invention. The choice of excipient(s) to a large extent depend on factors such as the particular mode of administration, the effect of the excipient on solubility and stability, and the nature of the dosage form. As used herein, "pharmaceutically acceptable carrier" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some embodiments, isotonic agents, including, but not limited to, sugars, polyalcohols (e.g., mannitol, sorbitol) or sodium chloride are included in the pharmaceutical composition. Additional examples of pharmaceutically acceptable substances include, but are not limited to, wetting agents or minor amounts of auxiliary substances such as wetting or emulsifying agents, preservatives or buffers, which enhance the shelf life or effectiveness of the antibody.

In some embodiments, the Fc-containing polypeptide conjugates (such as antibody drug conjugates) described herein can be deimmunized to reduce immunogenicity upon administration to a subject suing known techniques such as those described, e.g., in PCT Publication WO98/52976 and WO00/34317.

The pharmaceutical compositions described herein may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage. Any method for administering peptides, proteins or antibodies accepted in the art may suitably be employed for the Fc-containing polypeptide conjugates disclosed herein.

The pharmaceutical compositions described herein in some embodiments are suitable for parenteral administration. Parenteral administration of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. For example, parenteral administration includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intrasynovial injection or infusions; and kidney dialytic infusion techniques. In some embodiments, parenteral administration is the intravenous or the subcutaneous route.

Formulations of a pharmaceutical composition suitable for parenteral administration may be prepared, packaged, or sold in a form suitable for bolus administration or for continuous administration. Injectable formulations may be prepared, packaged, or sold in unit dosage form, such as in ampoules or in multi dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or engineered release. Engineered release formulations include controlled, delayed, sustained, pulsed, targeted and programmed release formulations. For example, in one aspect, sterile injectable solutions can be prepared by incorporating the Fc-containing polypeptide conjugate, e.g., antibody-drug conjugate or bispecific antibody-drug conjugate, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the exemplary methods of preparation are vacuum drying and freeze drying that yields a powder of the active ingredient plus any additional desired ingredient from a previously sterile filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

An exemplary, non-limiting pharmaceutical composition of the Fc-containing polypeptide conjugate (such as antibody drug conjugate) is a formulation as a sterile aqueous solution having a pH that ranges from about 5.0 to about 6.5 and comprising from about 1 mg/mL to about 200 mg/mL of an engineered polypeptide conjugate disclosed herein, from about 1 millimolar to about 100 millimolar of histidine buffer, from about 0.01 mg/mL to about 10 mg/mL of polysorbate 80, from about 100 millimolar to about 400 millimolar of trehalose, and from about 0.01 millimolar to about 1.0 millimolar of disodium EDTA dehydrate.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the invention are generally dictated by and directly dependent on (a) the unique characteristics of the agent moiety (e.g., small molecules such as cytotoxic agent) and the particular therapeutic or prophylactic effect to be achieved, and (b) the limitations inherent in the art of compounding such an active compound for the treatment of sensitivity in individuals.

The skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this invention may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens are well-known in the relevant art and would be understood to be encompassed by the skilled artisan once provided the teachings disclosed herein.

The invention also provides kits (or articles of manufacture) for use in the treatment of the disorders described above. Kits of the invention include one or more containers comprising an Fc-containing polypeptide conjugate (such as antibody drug conjugate) for treating a disease. For example, the instructions comprise a description of administration of the engineered Fc-containing polypeptide conjugate (such as antibody drug conjugate) to treat a disease, such as cancer (e.g., pancreatic, ovarian, colon, breast, prostate, or lung cancer). The kit may further comprise a description of selecting an individual suitable for treatment based on identifying whether that individual has the disease and the stage of the disease. The instructions relating to the use of the engineered Fc-containing polypeptide conjugate (such as antibody drug conjugate) generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable. The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an engineered polypeptide as described herein. The container may further comprise a second pharmaceutically active agent. The kits may optionally provide additional components such as buffers and interpretive information. Normally, the kit comprises a container and a label or package insert(s) on or associated with the container.

In some embodiments, there is provided a kit comprising a TGase (such as an engineered TGase, such as any one of the engineered TGase described herein). In some embodiments, the kit further comprises other reagents for carrying out the tranglutamination reaction. In some embodiments, the kit further comprises an instruction on carrying out any one of the conjugation methods described herein. In some embodiments, the kit further comprises a solid support for immobilizing the TGase (such as the engineered TGase) or the Fc-containing polypeptide (such as antibody). In some embodiments, the TGase (such as the engineered TGase) in the kit is immobilized on the solid support.

EXAMPLES

The invention can be further understood by reference to the following examples, which are provided by way of illustration and are not meant to be limiting.

Example 1. Generation of TGase Mutants

This example describes the generation of TGase mutants. With reference to FIG. 3, three regions which near active site entrance were deleted or mutated to enlarge the substrate binding pocket. Wild type TG_SL was cloned into pET39+ vector using NdeI and XhoI with an extra proline (SEQ ID NO:17). The following deletion mutants were made based on IgG1 and TG_SM docking: Mutant 1: Deletion from P1-E5 (SEQ ID NO:37); Mutant 2: Deletion from P245-P248 (SEQ ID NO:38); Mutant 3: Deletion from N283-L286 (SEQ ID NO:39); Mutant 4: Deletions of P1-E5 and N283-L286 (SEQ ID NO:40); Mutant 5: Deletion of all three regions specified by mutants 1, 2 and 3 (SEQ ID NO:41); Mutant 6: Deletion of P1-E5 and replace H280-A288 with G (SEQ ID NO:42); Mutant 7: Deletion of P1-E5 and replace A281-H290 with G (SEQ ID NO:43). Deletion area is greyed out, underlined or stricken-out as shown in FIG. 3. These mutants were more active toward IgG1.

Using DNA purified from *S. ladakanum* (ATCC27441) as PCR template, DNA sequences coding for wild type pro- or mature mTGase (wildtype TG_SL) and its mutants 1-3 (see above) were cloned into the pET39b vector at the NdeI and BamHI sites. Inclusion bodies of mature wildtype TG_SL and mutants 1-3 were obtained from *E. coli* BL21 (DE3) cells transformed with respective vectors. After solubilization in 8 M urea, wildtype TG_SL and mutants were refolded by dilution into renaturation buffer (1 mM DTT, 50 mM Tris, pH 8.0). The enzymes were further purified by Ni-NTA and cation exchange columns. Alternatively, Pro-mTgase was expressed as soluble inactive pro-enzyme in *E. coli*. Then, the active enzyme was obtained after cleavage of the pro domain by endokinase light chain (EKL).

Figure 7:
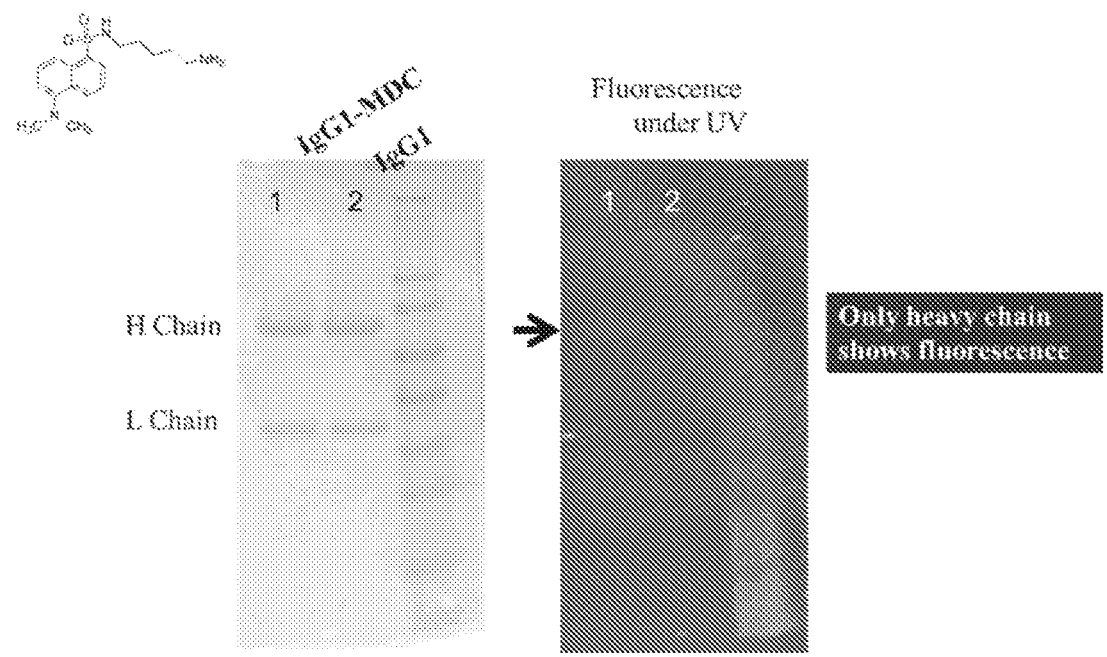
FIG. 7 provides SDS PAGE analysis of IgG1-MDC conjugates.

Example 2. Conjugation of IgG1 with Monodansylcadaverine (MDC) Catalyzed by mTgase MDC was chosen for this experiment because it has a primary amine and its fluorescence can be easily monitored. MDC is used here to demonstrate its conjugation to mAB. To purified IgG1 (1-10 mg/ml) in Tris-buffer (pH 6.5-8.5), add MDC (Sigma-Aldrich) in DMSO to final concentrations of 1-5 mM (final DMSO 2-10%). Add purified wildtype TG_SL or its mutant to a final concentration of 0.05-1.0 mg/ml. Incubate the reaction mixtures at 37° C. Reaction was followed by HPLC using phenyl hydrophobic interaction column (PHIC, Tosoh Bioscience LLC). At the beginning of the reaction, the product was dominated by DAR1, where only one heavy chain of IgG1 was coupled with MDC. As the reaction progressed, DAR 2, where both heavy chains of IgG1 are coupled with MDC, became the major product. Toward the end of reaction (8 hours at 0.2 mg/ml of mTgase at pH 7), conjugation yield reached 80% for DAR2 with 20% of DAR 1 left, or 90% for heavy chain (HC) when the sample was reduced by 10 mM TCEP and analyzed on C4-1000A column (Vydac) (see FIG. 6). The selective conjugation of MDC to HC was visualized on SDS PAGE (FIG. 7). Other mTgases, such as TG_SM from *S. mobaraensis* (purified from Ajinomoto's Activa TI), was also tested. Mutants were more active than the wild type toward IgG1, although wild type TGase could also catalyze ADC reaction at high concentration (>0.1 mg/ml). It was further found that TG_SM (sold by Ajinomoto and used by Pfizer and Innate Pharma) also works at high concentration, but only had about 30% activity comparing to TG_SL.

Example 3. Pegylation of IgG1 with 1 kDa mPEG-NH2 by mTgase Catalysis

This experiment was carried out essentially as described in Example 2. The acyl acceptor MDC was replaced with 1 kDa methoxy-PEG-amine (JenKem, USA) in pH 7.0 to a final concentration of 1 to 2 mM, PEGylated IgG1 was obtained. Sample analysis of an overnight reaction at 37° C. on a C4 column after reduction with TCEP showed 90% modification of the heavy chains.

Example 4. Conjugation of IgG1 with Monodansylcadaverine (MDC) Catalyzed by Immobilized mTgase To simplify mTgase removal and allow reuse of the enzyme, immobilized mTgase was used in catalysis. In preparing a column of immobilized mTgase, 1 ml of 15 mg/ml of mTgase in carbonate buffer (pH 8.3) was used for each NHS activated HITRAP® HP column of 1.0 ml (GE) following manufacturer's protocol. 0.5 ml of purified IgG1 at 1-10 mg/ml in Tris-buffer (pH 6-8.0) with 1-5 mM of MDC was injected into HITRAP®-mTgase column. The column was sealed at both ends and incubated at 37° C. overnight. The next day, reaction mixture was eluted with Tris buffer. The column was rejuvenated with 1-20 mM TCEP for the next conjugation reaction. There was no loss of activity of immobilized mTgase after each use. Yield of 90% HC was reached at each run, similar to the yield obtained with free mTgase.

Example 5. Conjugation of IgG1, 2 and 4 with Cytotoxins Catalyzed by mTgase

Toxins with an amine linker could be conjugated to IgG1 in a One-Step protocol just as MDC does (FIG. 4). Although a linker as simple as —(CH2)$_n$—NH2 (where n≥4 as in lysine side chain), use of ethylene glycol scaffold could increase the solubility of linker-drug and facilitate the conjugation reactions. This example demonstrates conjugation of MAY-PEG4 (non-cleavable linker, FIG. 8) and MAY-PVCL (cleavable linker, FIG. 9) to IgG1.

Figure 10:
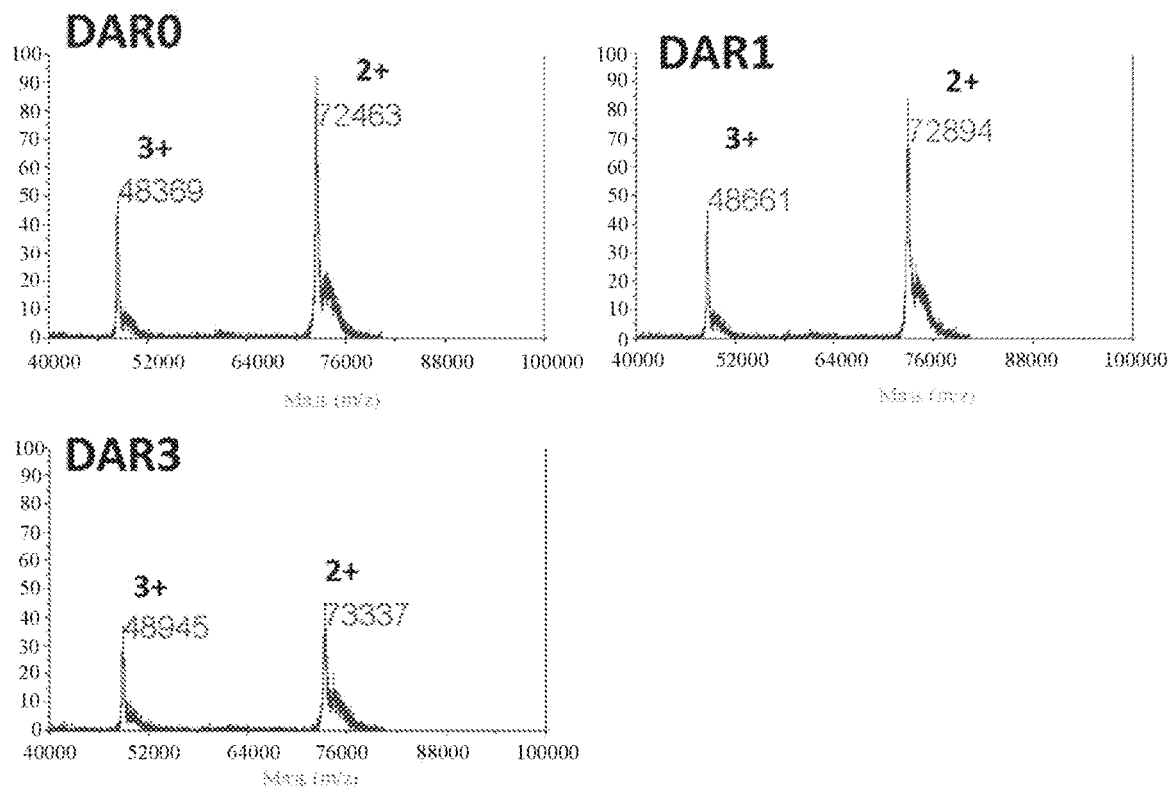
FIG. 10 provides MALDI-TOF spectra for DAR0 (i.e. naked IgG1, top panel), DAR 1 (middle panel) and DAR 2 (bottom panel) of IgG1-MAY-PEG4.

A maytansine derivative containing an extended, non-cleavable linear PEG linker with a primary amine group of MW: 896.42 Da is depicted in FIG. 8. MAY-PEG4 in DMSO was added to IgG1 (1-10 mg/ml in pH 8.0 Tris buffer) to a final concentration of 1-2 mM. mTgase was added to a final concentration of 0.2-1.0 mg/ml and the reactions were incubated at 37° C. The reaction was monitored by HPLC analysis as described in example 2. After overnight, a yield of 60% modified heavy chains was obtained. Both DAR 1 and DAR 2 products were seen (FIG. 10).

Figure 11:
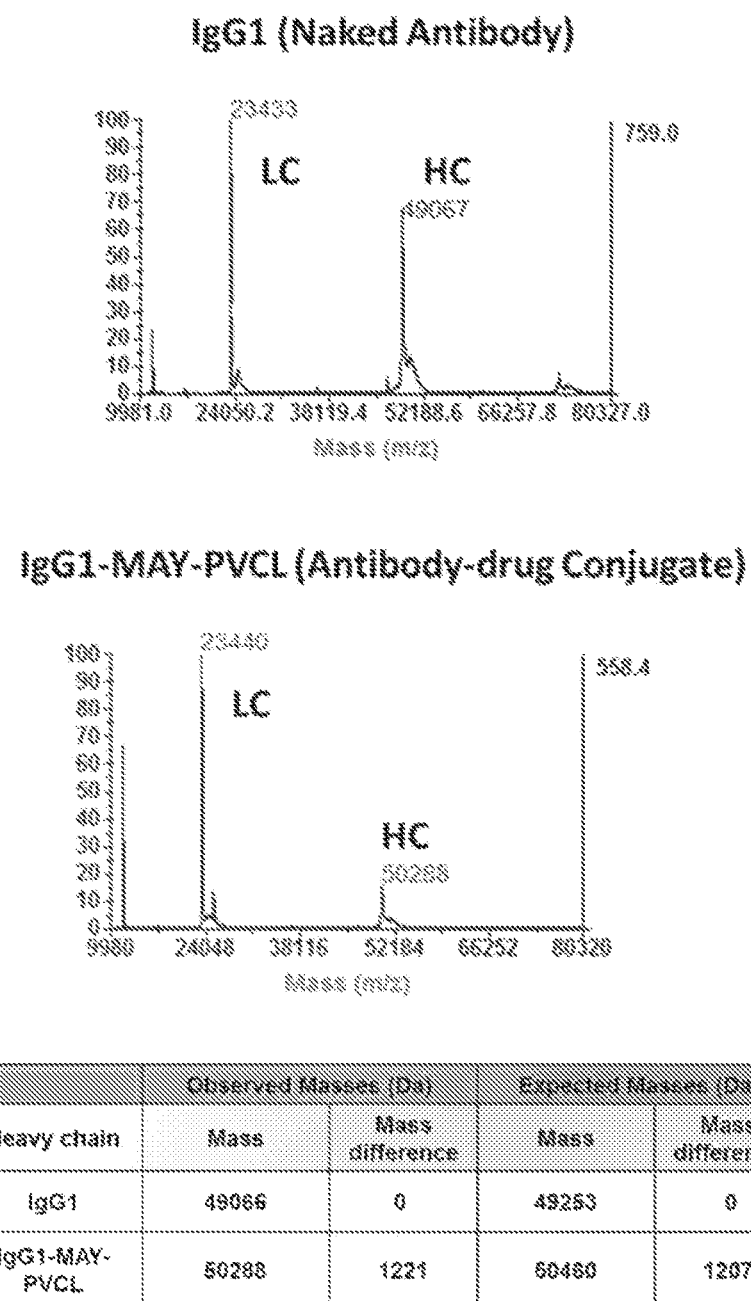
FIG. 11 provides MALDI-TOF spectra of naked IgG1 (left panel) and IgG1 conjugated to MAY-PVCL (right panel).

A maytansine derivative containing a cleavable linker with a self-immolative spacer and terminal lysine of molecular weight 1224.58 Da is shown in FIG. 9. Conjugation reaction was run the same way as above by replacing MAY-PEG4 with MAY-PVCL (1.0 mg/ml). After incubation at 37° C. for 8 hours, 40% of the heavy chain was modified (FIG. 11). Low yield is attributed to the low solubility of the drug.

Example 6. Drug to Antibody Ratio (DAR) Determination and Conjugation Site Mapping on IgG1

Due to the heterogeneity of glycan chains, IgG1 would display multiple peaks on its Mass Spectra. To simplify mass analysis, all mAB conjugates were deglycoslyated before mass spectrometer analysis using PNGaseF (Promega, Madison, Wis.), so a single peak would be observed for each species of the same charge. By doing so, the original glycan linked asparagine (N) is changed to aspartate (D).

Mass Confirmation of DAR1 and DAR2. Expected DAR 1 and DAR 2 of IgG1-MAY-PEG4 from Example 5 were purified on Phenyl HIC. After deglycosylation, samples were spotted on a 196 well steel plate and analyzed on MALDI-TOF (ABI 4700, Applied Biosystems, Redwood City, Calif.). As a control, naked IgG1 was used (DAR0). Mass spectra were acquired in positive High Mass linear mode and multiple charged species (double and triple) were used to calculate molecular weight. MAY-PEG4 drug has a molecular weight of 896 Da. Therefore conjugation of one molecules of MAY-PEG4 to IgG1 (DAR1) would result in expected mass difference of 879 Da (896−17 loss of NH3=879 Da), whereas conjugation of two molecules to IgG1 (DAR2) would result in mass difference of 1758 Da. MALDI-TOF spectra in FIG. 10 confirmed DAR1 and DAR2.

Confirmation of Conjugation on Heavy Chain Only. To confirm that drug molecule was conjugated to IgG1's heavy chain (HC) but not light chain (LC), purified DAR2 of IgG1-MAY-PVCL from Example 5 was deglycosylated and reduced with 20 mM DTT for 30 min at 37° C. Mass spectra were acquired in positive High Mass linear mode using ABI4700. MAY-PVCL drug has a molecular weight of 1224 Da. Therefore, conjugation of one MAY-PVCL to heavy chain would result in expected mass difference of 1207 Da (1224−17=1207 Da) and no difference in molecular weight of light chains (FIG. 11). On the other hand, DAR1 has both naked HC and HC-MAY-PVCL peaks on its mass spectrum, indicating DAR1 has only one HC conjugated.

Peptide Mapping to Verify Site-Specific Conjugation at Q295. Purified DAR2 from Example 2 (both heavy chains of IgG1 containing MDC) and naked IgG1 were deglycosylated, reduced, alkylated, digested into peptides using trypsin and/or chymotrypsin (Promega, Madison, Wis.) and separated by reversed phase chromatography (C18) prior to mass spectrometry analysis. Digested peptides were monitored on HPLC by UV absorbance at 328 nm (λmax of MDC). Only one peak at 328 nm was identified in DAR2 samples, whereas no peak was detected in control antibody. MALDI-TOF analysis identified that peak as a single charged peptide EEQYDSTYR (SEQ ID NO:27) from trypsin digestion or NAKTKPREEQY (SEQ ID NO:28) from chymotrypsin digestion containing Glutamine 298 (Sequential Q298 and is Q295 by Kabat numbering system) with exactly one MDC (1508.7 observed-1190.5 peptide+335 MDC-17 NH3=318 Da; 1681.9 observed-1363.6 peptide=318) (gray rows in Table 1). To exclude other Glutamines (other than Q298) as additional conjugation sites, full peptide mapping experiments were performed using unmodified IgG1 and IgG1-MDC conjugate. The digested samples were directly analyzed without purification to identify all glutamine-containing peptides on heavy chain. Out of all 16 glutamines, Q298 was the only conjugation site with MDC attached (Table 1) while all other glutamine containing peptides remain unchanged.

TABLE 1

Glutamine containing peptides identified after proteases digestion*

| Peptides from Trypsin or Chymotrypsin* Digestion | Peptide Position | Glutamine (Q) Sequential Numbering | Expected Mass | IgG1 Observed Mass | IgG1-MDC Observed Mass |
| --- | --- | --- | --- | --- | --- |
| EVQLVESGGGLVQPGGSLR (SEQ ID NO: 20) | 1-13 | Q3, Q13 | 1882.2 | 1882.1 | 1882.1 |
| VESGGGLQPGGSL* (SEQ ID NO: 21) | 5-18 | Q13 | 1256.6 | 1256.7 | 1256.7 |
| QAPGKGLEWVAR (SEQ ID NO: 22) | 39-50 | Q39 | 1311.7 | 1311.6 | 1311.7 |
| NTAYLQMNSLR (SEQ ID NO: 23) | 77-87 | Q82 | 1310.6 | 1310.6 | 1310.7 |
| WGGDGFYAMDYWGQGTLVTVSSASTK (SEQ ID NO: 24) | 99-124 | Q112 | 2784.2 | 2784.2 | 2784.2 |
| TSGVHTFPAVLQSSGL* (SEQ ID NO: 25) | 167-182 | Q178 | 1600.8 | 1600.9 | 1600.9 |

TABLE 1-continued

Glutamine containing peptides identified after proteases digestion*

| Peptides from Trypsin or Chymotrypsin* Digestion | Peptide Position | Glutamine (Q) Sequential Numbering | Expected Mass | IgG1 Observed Mass | IgG1-MDC Observed Mass |
|---|---|---|---|---|---|
| GTQTY* (SEQ ID NO: 26) | 197-201 | Q199 | 569.2 | 569.3 | 569.3 |
| EEQYDSTYR (SEQ ID NO: 27) | 296-304 | Q298 | 1190.5 | 1190.5 | 1508.7 (1190.5 + 318) |
| NAKTKPREEQY* (SEQ ID NO: 28) | 288-299 | Q298 | 1363.5 | 1363.6 | 1681.9 (1363.6 + 318) |
| EVQLVESGGGLVQPGGSLR (SEQ ID NO: 29) | 305-320 | Q314 | 1808.0 | 1808.0 | 1808.0 |
| GQPREPQVYTLPPSR (SEQ ID NO: 30) | 344-358 | Q345 | 1724.9 | 1724.8 | 1724.9 |
| EPQVYTLPPSR (SEQ ID NO: 31) | 348-358 | Q350 | 1286.6 | 1286.5 | 1286.6 |
| KNQVSLTCLVK (SEQ ID NO: 32) | 364-373 | Q365 | 1104.6 | 1105.6 | 1105.6 |
| GFYPSDIAVEWESNGQPENNYK (SEQ ID NO: 33) | 374-395 | Q389 | 2544.1 | 2544.5 | 2544.5 |
| TVDKSRWQQGNVF* (SEQ ID NO: 34) | 414-426 | Q421 | 1564.7 | 1564.7 | 1564.8 |
| WQQGNVFSCSVMHEALHNHYTQK (SEQ ID NO: 35) | 420-442 | Q421, Q422, Q441 | 2744.2 | 2744.7 | 2744.8 |

*Note:
Sequential Q298 and is Q295 by Kabat numbering system. N300 (or Kabat N297) became D300 when deglycosylated.

To confirm Q298 as the specific conjugation site on IgG1 when real cytotoxins were used, IgG1 conjugates of MAY-PEG4 and TAM1 (a tubulysin A derivative with an amine linker) were deglycosylated, reduced, alkylated, digested into peptides using trypsin and separated by reversed phase chromatography prior to mass spectrometry analysis. The same peptide EEQYDSTYR (SEQ ID NO:27) containing Q298 was identified in both IgG1-TAM1 and IgG1-MAY-PEG4 conjugates with mass corresponding to one drug molecule attached: 2134.0 (1190.5+960.5−17) and 2069.8 (1190.5+895.5−17), respectively (Table 2).

TABLE 2

Q298-containing peptide identified after tryptic digest

| Peptide | Peptide Position | Glutamine (Q) | Expected Mass | IgG1 Observed Mass | IgG1-TAM1 Observed Mass | IgG1-MAY-PEG4 Observed Mass |
|---|---|---|---|---|---|---|
| EEQYDSTYR (SEQ ID NO: 27) | 296-304 | Q298 | 1190.5 | 1190.5 | 2134.0 (1190.5 + 960.5 − 17) | 2069.8 (1190.5 + 895.5 − 17) |

Example 7. Conjugation of IgG Subclasses Catalyzed by mTGase

Purified human IgG 2 or IgG 4 at 1-10 mg/ml in Tris buffer (pH 7.0-8.0) was reacted with 2-5 mM of MDC following the addition of 0.1 to 1 mg/mL of purified mTGase. The mixture was incubated at 37° C. for 8-16 hours and then analyzed on phenyl hydrophobic interaction column or reduced by 10 mM TCEP on C4 column. Similar to IgG1, IgG2 and IgG4 were conjugated with MDC to show DAR1 and DAR2 accumulating with time (FIG. 6).

Figure 5:
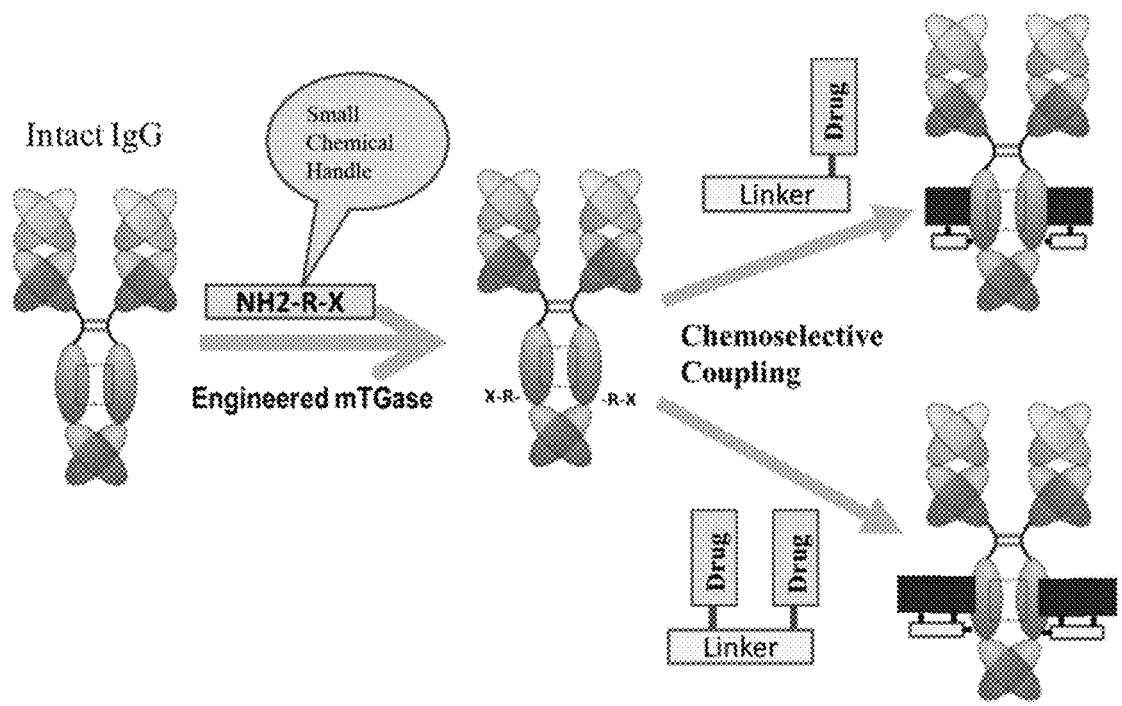
FIG. 5 provides a diagram showing a two-step antibody-drug conjugation method.

Example 8. Two-Step Protocol to Prepare Antibody Drug Conjugates Using mTGase While the one step conjugation reaction is simple and straightforward, the yield is affected by the solubility of the drug. When drug concentration is low, the by-product from deamidation may be significant. To suppress deamidation, a highly soluble amine containing chemical handle was used in excess (molar ratio of chemical:mAB>10) in the first step conjugation catalyzed by mTgase. Then, drug molecules were cross-linked to mAB in the second step via chemoselective ligation reactions (FIG. 5). Many chemoselective pairs can be used:
Amino-oxy-/Aldehyde or Ketone
Sulfhydryl/Maleimide
Azide/alkyne IgG1 conjugation of PEG by mTgase via amino propyl acetal. To 1-10 mg/ml of IgG1 in pH 7.0-8.0 Tris buffer, add 3-aminopropionaldehyde diethyl acetal (CAS#41365-75-7) to a final concentration of 2-50 mM and mTgase to 0.05 to 0.5 mg/ml. The reaction mixture was incubated at 37° C. for 2-16 hours until reaction reached completion. After diafiltration to remove excess acetal, adjust the pH to 2-4 for 2-10 hours at room temperature with formic acid or HCl to regenerate aldehyde group. Adjust pH of IgG1-aldehyde with sodium carbonate back to 5-8. Add amino-oxy-PEG (20 kDa) to 3 to 4 times of IgG1 (molar ratio) plus a catalyst of 50 to 100 mM aniline or 10 mM of 5-methoxyanthranilic acid. After overnight incubation at room temperature, IgG1-(PEG20k)$_2$ reached yield of 95%.

IgG1 conjugation of drug by mTgase via amine-azide. To 1-10 mg/ml of IgG1 in pH 7.0-8.0 Tris buffer, add 3-azido-1-propanamine (CAS#88192-19-2) to a final concentration of 2-50 mM and mTgase to 0.05 to 0.5 mg/ml. The reaction mixture was incubated at 37° C. for 2-16 hours. Yield reached 100%. After diafiltration to remove excess azido propyl amine, DBCO-Maytansine was added to 3 times of IgG (by molar). IgG1-(Maytansine)$_2$ yield reached over 95%.

Example 9. In Vitro Cell Assay to Assess ADC Potency Prepared by mTgase

SK-BR-3 cells were seeded in 96 well black clear-bottom plates at 10K cells/well and cultured for 24 hours. Cells were treated for 96 hours with 2 fold serially diluted antibody-drug conjugates in triplicates. Cells viability was determined by CELLTITER™ Blue Cell Viability Assay (Promega, Madison, Wis.). Relative cell viability was determined as a percentage of untreated control. IC50 was calculated using a four parameter logistic model from XLfit. Table 3 shows the drug to antibody ratio and IC50 in SK-BR-3 cells using various trastuzumab-drug conjugates.

TABLE 3

IC50 of antibody-drug conjugates in SK-BR-3 cells

| Drug | DAR | IC$_{50}$ (µg/ml ADC) | IC$_{50}$ (nM drug equivalent) |
|---|---|---|---|
| ADC-TAM1 | DAR1 | 0.033 | 0.22 |
| ADC-TAM1 | DAR2 | 0.017 | 0.22 |
| ADC-MAY-PEG4 | DAR1 | 0.046 | 0.31 |
| ADC-MAY-PEG4 | DAR2 | 0.028 | 0.38 |
| ADC MAY-PVCL | DAR1 | 0.081 | 0.54 |
| ADC MAY-PVCL | DAR2 | 0.055 | 0.72 |

Example 10. Site-Specific ADCs Prepared by mTgase with Stable Non-Cleavable Linkers are Highly Stable and Potent in Xenograft Mice Trastuzumab (10 mg/ml) and Monomethyl auristatin E (MMAE) with each of 9 non-cleavable PEG linkers (CH$_2$CH$_2$O)$_x$ (x=2, 4, 6, 8, 10, 12, 16, 20, and 24, FIG. 12) were conjugated respectively as described in Example 5. ADCs were purified by Protein A column to remove mTgase and excess MMAE. The average DARs are ~1.9 when the reduced ADC samples were analyzed on HPLC using C4 column. In SK-BR-3 cell based assay, these ADCs are all potent with IC50 from 38 to 148 pM (Table 4).

TABLE 4

IC50 (pM) of Trastuzumab-MMAE conjugates in SK-BR-3 or BT474cells

| Linker | IC$_{50}$ SK-BR-3 | IC$_{50}$ BT474 |
|---|---|---|
| PEG2 | 148 | 1095 |
| PEG4 | 61 | 273 |
| PEG6 | 50 | 234 |
| PEG8 | 42 | 230 |
| PEG10 | 40 | 271 |
| PEG12 | 38 | 267 |
| PEG16 | 40 | 281 |
| PEG20 | 72 | 495 |
| PEG24 | 114 | 807 |
| PEG3c | 60 | 283 |

Figure 13:
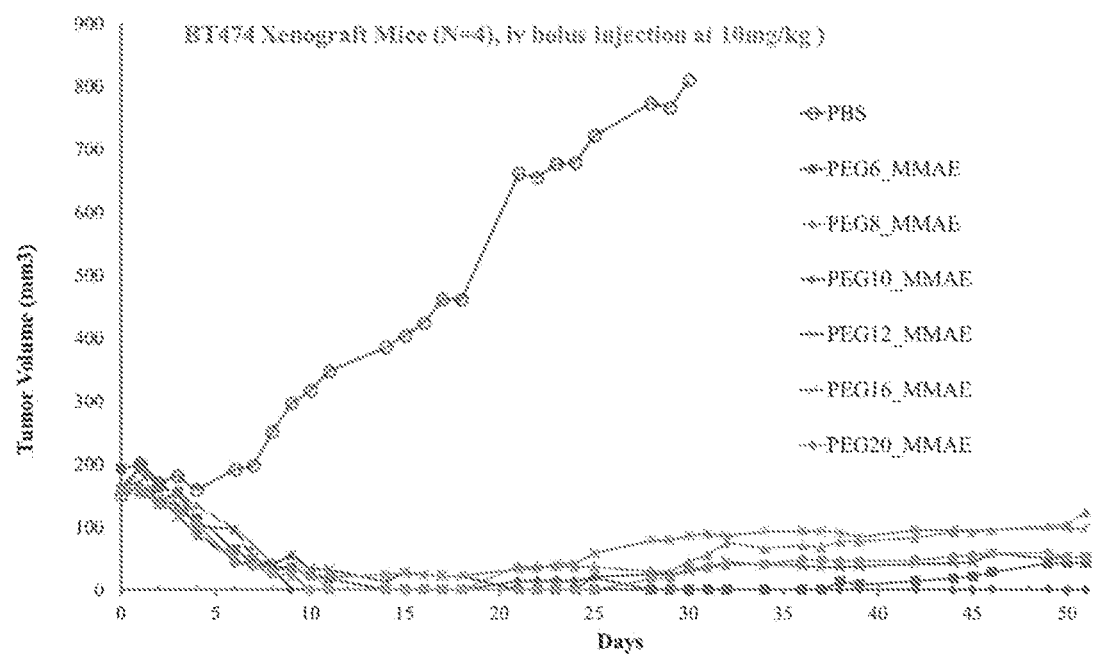
FIG. 13 provides in vivo efficacy of trastuzumab-PEGx-MMAE conjugates prepared by Tgase in BT474 xenograft mice.

Six of the trastuzumab-MMAE conjugates were selected for in vivo test using BT474 xenograft mice. Each female athymic nude mouse (4 week old, 18-22 g; Harlan) was implanted with one estrogen 3 mm (60 day slow release, Innovative Research of America) tablet 2-3 days prior to cell injection. BT474 cells were resuspended to a final 50-60 million cells/ml, and mixed 1:1 with matrigel, then 200 µl was injected subcutaneously into the flank of each mouse. Treatment starts when the tumor volume (½×L×W×H) reaches around 200 mm$^3$ after 3 weeks. ADCs were diluted into PBS buffer to a final concentration 1 mg/ml and were administered intravenously into mice tails at about 200 µl to reach 10 mg/kg dose. Tumor size was measured daily using a digital caliper. Even though Linker PEG6 and 8 seemed to be optimal in the BT474 cell-based assay (Table 4), the difference in in vivo efficacy is very small (FIG. 13).

Figure 14:
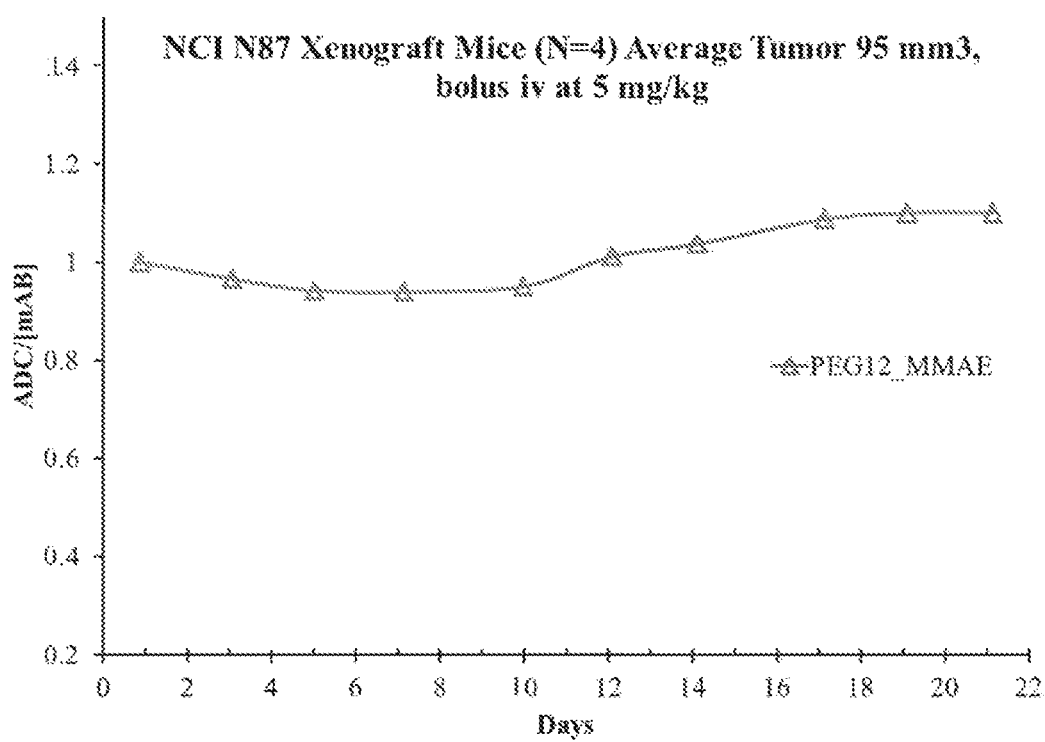
FIG. 14 provides in vivo stability of a trastuzumab-PEG12-MMAE conjugate prepared by Tgase in NCI N87 xenograft mice.

Since all 6 ADCs were potent, we only tested one ADC with PEG12 linker for its stability in blood. NCI N87 xenograft mice were generated in a similar way as the BT474 xenograft mice with ~5 million cells per mouse except no estrogen tablet was used. After ADC administration, blood samples of 20 µl were taken every 1-2 days up to 21 days by poking mouse tails and mixed with 120 µl of storage buffer (PBS with 10 mM EDTA and 0.1 M NH4Cl). Then total trastuzumab and ADC were analyzed by sandwich ELISA. Black NUNC® Maxisorp 96 plates were coated with Her2 protein at 100 ng/well. Samples were further diluted with PBS as needed to suit the linear detection range of 10 pg to 2 ng (for either Trastuzumab or ADC). After applying samples (fresh ADC dilutions were used as both total mAb and ADC standards) and washing, rabbit polyclonal anti-trastuzumab (for total mAb) or anti-MMAE (for total ADC) were applied as secondary antibodies while Goat anti-Rabbit IgG-HRP (Life-technologies) was used as the detection antibody. AMPLEX® Red (Cayman Chemical)/4-Iodophenol (Sigma)/H$_2$O$_2$ mixture was used as fluorescence substrate. Plates were read on SpectraMax GEMINI™ with 555 nm Ex and 585 nm Em. The ratio of ADC/mAb vs time was plotted in FIG. 14. It is clear that site-specific ADC with a stable non-cleavable linker is completely stable in blood.

Figure 15:
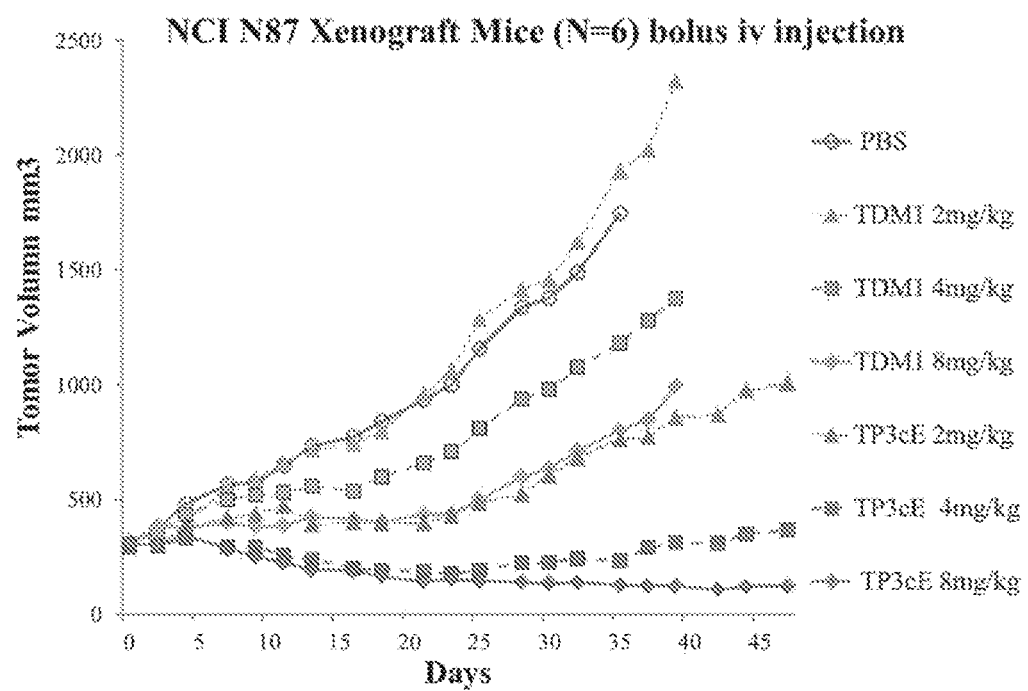
FIG. 15 provides comparison of in vivo efficacy of a trastuzumab-PEG3c-MMAE conjugate (DAR2, referred herein as TP3cE) and TDM-1 (Genentech) conjugate in NCI N87 xenograft mice.
Figure 16:
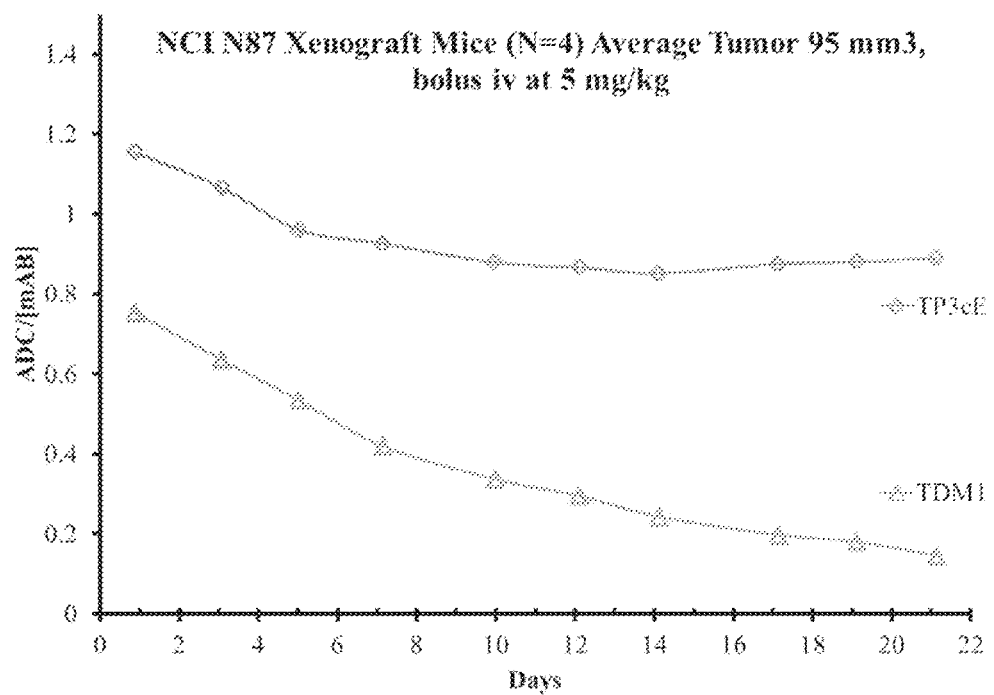
FIG. 16 provides comparison of in vivo stability of a trastuzumab-PEG3c-MMAE conjugate (DAR2, referred herein as TP3cE) and TDM-1 (Genentech) conjugate in NCI N87 xenograft mice.
Figure 17:
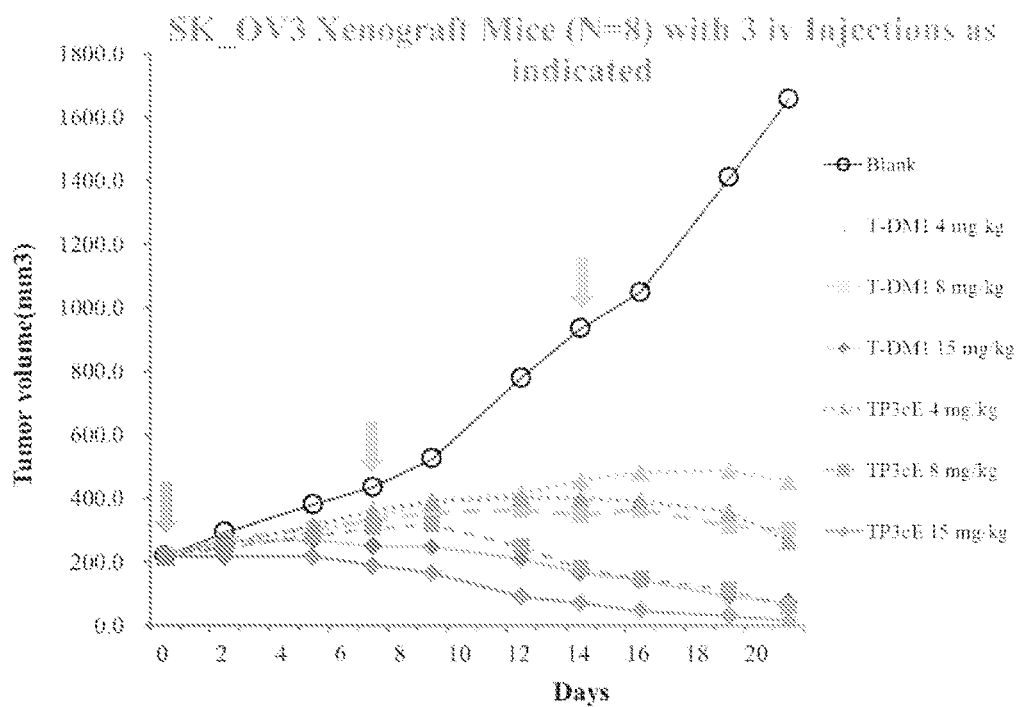
FIG. 17 provides a comparison of in vivo efficacy of a trastuzumab-PEG3c-MMAE conjugate (DAR2, referred herein as TP3cE) and TDM-1 (Genentech) conjugate in SK_Ov3 xenograft mice. Arrows in the plot indicate time points for administration of the doses of antibody drug conjugates.

Example 11. DAR 2 Site-Specific ADC Prepared by mTgase with a Cleavable Linker is More Stable and Potent than Commercial TDM-1 in Xenograft Models Trastuzumab (10 mg/ml) and MMAE with cleavable PEG3c linker (FIG. 12) was conjugated and purified as described in Example 10. This ADC, named as TP3cE, has DAR of 1.9, and high potency in vitro (Table 4). In vivo studies were conducted in comparison to TDM-1 (Genentech) in both NCI N87 and SK_Ov3 xenograft models. In NCI N87 model, TP3cE is 4 times more efficacious than TDM-1 with a single intravenous injection (FIG. 15). Blood sample analysis show that TP3cE is completely stable in blood for up to 21 days while TDM-1 lost 50% of its toxin in 5 days (FIG. 16). In SK_Ov3 xenografts, TP3cE at 3 weekly doses of either 15 or 8 mg/kg resulted in complete tumor remission while TDM-1 showed efficacy only at 15 mg/kg (FIG. 17).

Example 12. DAR 4 Site-Specific ADC Prepared by mTgase with Two-Step Process

Trastuzumab (10 mg/ml) and each of a group of 3-arm PEG linkers (1-5 kDa) with one amine group and two azide groups (FIG. 18, top; Conju-probe and Jenkem) (4-8 mg/ml) were conjugated and purified respectively as described in Example 10. The antibody-linker conjugation reactions reached >90% conversion when analyzed reduced by HPLC using a C4 column.

Five-fold molar excess of Alkyne-PEG4c-MMAE (FIG. 18, bottom panel) was then coupled to one of the products above, trastuzumab-3-arm-PEG (1 kDa) (1-10 mg/ml), in the presence of 0.1-1 mM $CuSO_4$ and 1-5 mM Sodium ascorbate for 10-300 minutes. The final DAR 4 ADC product, denoted TP6TP4cE, was then purified by protein A as described in Example 10 and the actual DAR was 3.8 as determined by HPLC using a C4 column. TP6TP4cE in vitro activity is higher than TP3cE of DAR 2 as shown in Table 5.

TABLE 5

| IC50 (pM) of Trastuzumab-MMAE conjugates in BT474cells | | |
|---|---|---|
| Linker | DAR | $IC_{50}$ BT474 |
| TP3cE | 2 | 280 |
| TP6TP4cE | 3.8 | 80 |

The invention claimed is:

1. A method of making an antibody drug conjugate comprising an antibody specifically conjugated to a conjugate moiety comprising: contacting an antibody composition comprising the antibody with the conjugate moiety in the presence of a transglutaminase under a condition sufficient to generate the antibody drug conjugate, wherein at least about 50% of the antibody in the antibody composition is glycosylated in the Fc-region, wherein the conjugate moiety is conjugated to an endogenous acceptor glutamine residue on the antibody, and wherein the transglutaminase is a wildtype transglutaminase and the concentration of the transglutaminase in the reaction mixture is about 0.1 mg/ml to about 1 mg/ml.

2. The method of claim 1, wherein the transglutaminase is derived from *Streptomyces ladakanum* or *Streptomyces mobaraensis*.

3. The method of claim 1, wherein the transglutaminase consists of the amino acid sequence of SEQ ID NO: 16, or SEQ ID NO: 18.

4. The method of claim 1, wherein the transglutaminase has a purity of at least about 90%.

5. The method of claim 1, wherein the molar ratio of the transglutaminase and the antibody composition is about 10:1 to about 1:10.

6. The method of claim 1, wherein the transglutaminase is immobilized on a solid support.

7. The method of claim 1, wherein the antibody is immobilized on a solid support.

8. The method of claim 1, where the antibody is a human or humanized antibody.

9. The method of claim 1, wherein both heavy chains of the antibody are conjugated to the conjugate moiety.

10. The method of claim 1, wherein the conjugate moiety comprises an active moiety selected from the group consisting of a moiety that improves the pharmacokinetic property of the antibody composition, a therapeutic moiety, and a diagnostic moiety.

11. The method of claim 1, wherein the conjugate moiety comprises a toxin.

12. The method of claim 1, wherein the antibody is N-glycosylated in the Fc-region.

13. The method of claim 1, wherein the concentration ratio between the conjugate moiety and the antibody is from about 2:1 to about 800:1.

14. A method of making an antibody drug conjugate comprising an antibody specifically conjugated to a conjugate moiety comprising a small molecule handle and an active moiety comprising:
   a) contacting an antibody composition comprising the antibody with the small molecule handle in the presence of a transglutaminase under a condition sufficient to generate an intermediate conjugate comprising the antibody specifically conjugated to the small molecule handle, wherein the transglutaminase is a wildtype transglutaminase and the concentration of the transglutaminase in the reaction mixture is about 0.1 mg/ml to about 1 mg/ml, and
   b) contacting the intermediate conjugate with the active moiety thereby obtaining the antibody drug conjugate, wherein at least about 50% of the antibody in the antibody composition is glycosylated in the Fc-region, wherein the conjugate moiety is conjugated to an endogenous acceptor glutamine residue on the antibody, and wherein the active moiety is selected from the group consisting of a moiety that improves the pharmacokinetic property of the antibody composition, a therapeutic moiety, and a diagnostic moiety.

15. The method of claim 14, wherein the small molecule handle has the structure of $NH_2$—R, wherein R is a moiety that allows the attachment of the active moiety.

16. A method of making an antibody drug conjugate comprising an antibody specifically conjugated to a conjugate moiety comprising: contacting an antibody composition comprising the antibody with the conjugate moiety in the presence of a transglutaminase under a condition sufficient to generate the antibody drug conjugate, wherein at least about 50% of the antibody in the antibody composition is glycosylated in the Fc-region, wherein the conjugate moiety is conjugated to an endogenous acceptor glutamine residue on the antibody, and wherein the transglutaminase is a wildtype transglutaminase with an added proline residue at the N-terminus, and optionally a purification tag, and the concentration of the transglutaminase in the reaction mixture is about 0.1 mg/ml to about 1 mg/ml.

\* \* \* \* \*